US011174291B2

(12) United States Patent
Pettit et al.

(10) Patent No.: US 11,174,291 B2
(45) Date of Patent: Nov. 16, 2021

(54) SILSTATIN COMPOUNDS

(71) Applicants: George Robert Pettit, Paradise Valley, AZ (US); Pablo Arce, Tempe, AZ (US); Robin K. Pettit, Fort McDowell, AZ (US)

(72) Inventors: George Robert Pettit, Paradise Valley, AZ (US); Pablo Arce, Tempe, AZ (US); Robin K. Pettit, Fort McDowell, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/536,039

(22) Filed: Aug. 8, 2019

(65) Prior Publication Data

US 2019/0375794 A1    Dec. 12, 2019

Related U.S. Application Data

(63) Continuation of application No. 15/550,727, filed as application No. PCT/US2016/017834 on Feb. 12, 2016, now abandoned.

(60) Provisional application No. 62/116,344, filed on Feb. 13, 2015.

(51) Int. Cl.
| C07K 11/02 | (2006.01) |
| A61K 38/15 | (2006.01) |
| G01N 33/50 | (2006.01) |
| A61K 38/00 | (2006.01) |

(52) U.S. Cl.
CPC .............. *C07K 11/02* (2013.01); *A61K 38/15* (2013.01); *G01N 33/5011* (2013.01); *A61K 38/00* (2013.01)

(58) Field of Classification Search
None
See application file for complete search history.

(56) References Cited

U.S. PATENT DOCUMENTS

| 4,306,071 A | 12/1981 | Pettit et al. |
| 4,388,457 A | 6/1983 | Pettit |
| 4,414,205 A | 11/1983 | Pettit |
| 4,486,414 A | 12/1984 | Pettit |
| 4,560,774 A | 12/1985 | Pettit et al. |
| 4,611,066 A | 9/1986 | Pettit et al. |
| 4,816,444 A | 3/1989 | Pettit et al. |
| 4,833,257 A | 5/1989 | Pettit et al. |
| 4,866,071 A | 9/1989 | Pettit |
| 4,873,245 A | 10/1989 | Pettit et al. |
| 4,879,278 A | 11/1989 | Pettit et al. |
| 4,940,726 A | 7/1990 | Pettit et al. |
| 4,973,394 A | 11/1990 | Ross et al. |
| 4,978,744 A | 12/1990 | Pettit et al. |
| 4,985,436 A | 1/1991 | Pettit |
| 4,986,988 A | 1/1991 | Pettit et al. |
| 4,996,237 A | 2/1991 | Pettit et al. |
| 4,997,817 A | 3/1991 | Pettit |
| 5,047,532 A | 9/1991 | Pettit et al. |
| 5,072,004 A | 12/1991 | Pettit et al. |
| 5,076,973 A | 12/1991 | Pettit et al. |
| 5,130,414 A | 7/1992 | Pettit |
| 5,138,036 A | 8/1992 | Pettit et al. |
| 5,196,447 A | 3/1993 | Pettit et al. |
| 5,328,929 A | 7/1994 | Pettit et al. |
| 5,352,804 A | 10/1994 | Pettit et al. |
| 5,393,897 A | 2/1995 | Pettit et al. |
| 5,409,953 A | 4/1995 | Pettit et al. |
| 5,410,024 A | 4/1995 | Pettit et al. |
| 5,426,194 A | 6/1995 | Pettit et al. |
| 5,430,053 A | 7/1995 | Pettit et al. |
| 5,436,400 A | 7/1995 | Pettit et al. |
| 5,494,893 A | 2/1996 | Pettit et al. |
| 5,504,191 A | 4/1996 | Pettit et al. |
| 5,514,689 A | 5/1996 | Collins et al. |
| 5,519,050 A | 5/1996 | Pettit et al. |
| 5,521,284 A | 5/1996 | Pettit et al. |
| 5,529,989 A | 6/1996 | Pettit et al. |
| 5,530,097 A | 6/1996 | Pettit et al. |
| 5,554,725 A | 9/1996 | Pettit |
| 5,561,122 A | 10/1996 | Pettit |
| 5,569,786 A | 10/1996 | Pettit et al. |
| 5,583,224 A | 12/1996 | Pettit et al. |
| 5,599,902 A | 2/1997 | Pettit et al. |
| 5,635,483 A | 6/1997 | Pettit et al. |
| 5,646,246 A | 7/1997 | Pettit et al. |

(Continued)

FOREIGN PATENT DOCUMENTS

| EP | 0324574 B1 | 11/1993 |
| GB | 2206883 A | 1/1989 |

(Continued)

OTHER PUBLICATIONS

Jaitzig, Jennifer et al, "Reconstituted biosynthesis of the nonribosomal macrolactone antibiotic valinomycin in *Escherichia coli*." ACS Synth. Biol. (2014) 3 p. 432-438.*
Lu, Yan et al; "An overview of tubulin inhibitors that interact with the colchicine binding site." Pharm. Res. (2012) 29(11) p. 2943-2971.*
Wang, Dongyu et al, "TOtal synthesis of the marine cyclic depsipeptide viequeamide a." J. Nat. Prod. (2013) 76 p. 974-978.*

(Continued)

*Primary Examiner* — Fred H Reynolds

(74) *Attorney, Agent, or Firm* — Byrne Poh LLP; Nina R. Horan

(57) ABSTRACT

The present disclosure relates to Silstatin compounds, pharmaceutical compositions comprising such compounds, kits, and methods for using such compounds or pharmaceutical compositions.

11 Claims, 1 Drawing Sheet

(56) References Cited

U.S. PATENT DOCUMENTS

| | | | |
|---|---|---|---|
| 5,663,149 A | 9/1997 | Pettit et al. | |
| 5,665,860 A | 9/1997 | Pettit et al. | |
| 5,780,588 A | 7/1998 | Pettit et al. | |
| 5,801,222 A | 9/1998 | Pettit et al. | |
| 5,883,120 A | 3/1999 | Pettit | |
| 6,034,065 A | 3/2000 | Pettit et al. | |
| 6,060,505 A | 5/2000 | Blumberg et al. | |
| 6,239,104 B1 | 5/2001 | Pettit et al. | |
| 6,281,196 B1 | 8/2001 | Pettit et al. | |
| 6,323,315 B1 | 11/2001 | Pettit et al. | |
| 6,437,128 B1 | 8/2002 | Pettit et al. | |
| 6,569,834 B1 | 5/2003 | Pettit et al. | |
| 6,620,911 B1 | 9/2003 | Pettit et al. | |
| 6,686,445 B1 | 2/2004 | Pettit et al. | |
| 6,777,578 B2 | 8/2004 | Pettit et al. | |
| 6,943,194 B1 | 9/2005 | Pettit et al. | |
| 6,949,647 B2 | 9/2005 | Pettit et al. | |
| 7,018,987 B1 | 3/2006 | Pettit et al. | |
| 7,078,552 B2 | 7/2006 | Pettit et al. | |
| 7,098,204 B2 | 8/2006 | Meijer | |
| 7,105,695 B2 | 9/2006 | Pettit et al. | |
| 7,223,747 B2 | 5/2007 | Pettit et al. | |
| 7,279,466 B2 | 10/2007 | Pettit et al. | |
| 7,317,020 B2 | 1/2008 | Pettit et al. | |
| 7,351,830 B2 | 4/2008 | Pettit et al. | |
| 7,439,265 B2 | 10/2008 | Pettit et al. | |
| 7,462,609 B2 | 12/2008 | Pettit et al. | |
| 7,507,851 B2 | 3/2009 | Pettit et al. | |
| 7,541,346 B2 | 6/2009 | Pettit et al. | |
| 7,547,686 B2 | 6/2009 | Pettit et al. | |
| 7,557,096 B2 | 7/2009 | Pettit et al. | |
| 7,705,188 B2 | 4/2010 | Pettit et al. | |
| 7,709,643 B2 | 5/2010 | Pettit et al. | |
| 7,994,320 B2 | 8/2011 | Pettit et al. | |
| 8,053,416 B2 | 11/2011 | Pettit et al. | |
| 8,415,294 B2 | 4/2013 | Pettit et al. | |
| 8,633,154 B2 | 1/2014 | Pettit et al. | |
| 9,044,518 B2 | 6/2015 | Pettit et al. | |
| 9,175,041 B2 | 11/2015 | Pettit et al. | |
| 9,539,342 B2 | 1/2017 | Pettit et al. | |
| 10,435,435 B2 | 10/2019 | Pettit et al. | |
| 2003/0216361 A1 | 11/2003 | Pettit et al. | |
| 2004/0122083 A1 | 6/2004 | Pettit et al. | |
| 2004/0127467 A1 | 7/2004 | Pettit et al. | |
| 2005/0014849 A1 | 1/2005 | Pettit et al. | |
| 2005/0187240 A1 | 8/2005 | Pettit et al. | |
| 2005/0261246 A1 | 11/2005 | Chang et al. | |
| 2006/0100179 A1 | 5/2006 | Pero et al. | |
| 2007/0167412 A1 | 7/2007 | Pettit et al. | |
| 2009/0221666 A1 | 9/2009 | Pettit et al. | |
| 2010/0179108 A1 | 7/2010 | Pettit et al. | |
| 2017/0100491 A1 | 4/2017 | Pettit et al. | |
| 2018/0030095 A1 | 2/2018 | Pettit et al. | |
| 2019/0077808 A1 | 3/2019 | Pettit et al. | |
| 2019/0375794 A1 | 12/2019 | Pettit et al. | |

FOREIGN PATENT DOCUMENTS

| | | | |
|---|---|---|---|
| WO | 1985003708 A1 | 8/1985 | |
| WO | 1989008655 A1 | 9/1989 | |
| WO | 1996014856 A1 | 5/1996 | |
| WO | 1996018408 A1 | 6/1996 | |
| WO | 1997034598 A1 | 9/1997 | |
| WO | 1997048278 A1 | 12/1997 | |
| WO | 1998036765 A1 | 8/1998 | |
| WO | 1999015130 A1 | 4/1999 | |
| WO | 1999034788 A1 | 7/1999 | |
| WO | 1999035150 A1 | 7/1999 | |
| WO | 1999035164 A1 | 7/1999 | |
| WO | 2001018032 A2 | 3/2001 | |
| WO | 2001081288 A1 | 11/2001 | |
| WO | 2001081355 A1 | 11/2001 | |
| WO | 2001084929 A1 | 11/2001 | |
| WO | 2002050023 A2 | 6/2002 | |
| WO | 2002085848 A2 | 10/2002 | |
| WO | 2002102766 A2 | 12/2002 | |
| WO | 2003055446 A2 | 7/2003 | |
| WO | 2003059855 A1 | 7/2003 | |
| WO | 2003086414 A1 | 10/2003 | |
| WO | 2004052298 A2 | 6/2004 | |
| WO | 2004052875 A1 | 6/2004 | |
| WO | 2004052915 A2 | 6/2004 | |
| WO | WO 2004052915 | 6/2004 | |
| WO | 2004074248 A2 | 9/2004 | |
| WO | 2005007084 A2 | 1/2005 | |
| WO | 2005054809 A2 | 6/2005 | |
| WO | 2005089736 A2 | 9/2005 | |
| WO | 2006036743 A2 | 4/2006 | |
| WO | 2006076726 A1 | 7/2006 | |
| WO | 2006122296 A1 | 11/2006 | |
| WO | 2006124511 A2 | 11/2006 | |
| WO | 2008151306 A1 | 12/2008 | |
| WO | 2009011988 A2 | 1/2009 | |
| WO | 2012135440 A1 | 10/2012 | |
| WO | 2012148943 A1 | 11/2012 | |
| WO | 2016130969 A1 | 8/2016 | |
| WO | 2017019489 A1 | 2/2017 | |
| WO | 2017151947 A1 | 9/2017 | |
| WO | 2019094709 A1 | 5/2019 | |

OTHER PUBLICATIONS

Kaur, Harveen et al, "Total synthesis of the cyclic depsipeptide ym-280193, a platelet aggregation inhibitor." Org. Lett. (Jan. 2015) 17 p. 492-495.*

Pettit, George R. et al, "Antineoplastic agents 571. Total synthesis of bacillistatin 2." J. Nat. Prod. (2009) 72 p. 372-379.*

Koeller, Kathryn M. and Wong, Chi-Huey; "Complex carbohydrate synthesis tools for glycobiologists: enzyme based approach and programmable one pot strategies." Glycobiol. (2000) 10(11) p. 1157-1169.*

Duimstra et al., "A Gadolinium Chelate for Detection of beta-Glucuronidase: A Self-Immolvative Approach", Journal of the American Chemical Society, Aug. 2005, pp. 12847-12855.

International Preliminary Report on Patentability dated Aug. 24, 2017 in International Patent Application No. PCT/US2016/017834.

International Search Report and Written Opinion dated May 2, 2016 in International Patent Application No. PCT/US2016/017834.

Kuisle et al., "A General Methodology for Automated Solid-Phase Synthesis of Depsides and Depsipeptides: Preparation of a Valinomycin Analogue", Journal of Organic Chemistry, Oct. 1999, pp. 8063-8075.

Pettit, G.R. et al., "Antineoplastic Agents. Part 409: Isolation and Structure of Montanastatin from a Terrestrial Actinomycete", Bioorganic & Medicinal Chemistry, vol. 7, 1999, pp. 895-899.

Seattle Genetics, Inc., "Highlights of Precribing Information", FDA, Aug. 2011, pp. 10.

Alaoui, A. et al., "Protecting Groups for Glucuronic Acid: Application to the Synthesis of New Paclitaxel (Taxol) Derivatives", The Journal of Organic Chemistry, Dec. 2006, vol. 71, No. 26, pp. 9628-9636 <DOI:10.1021/io0612675>.

Bao, J. et al., "Antifouling and antibacterial polyketides from marine gorgonian coral-associated fungus *Penicillium* sp. SCSGAF 0023", The Journal of Antibiotics, 2013 (available online Dec. 2012), vol. 66, pp. 219-223 <DOI:10.1038/ja.2012.110>.

Bollenback, G. et al., "The Synthesis of Aryl-D-glucopyranosiduronic Acids", Journal of the American Chemical Society, Jun. 1955 (available online May 2002), vol. 77, No. 12, pp. 3310-3315 <DOI:10.1021/ja01617a047>.

Bosslet, K. et al., "Elucidation of the Mechanism Enabling Tumor Selective Prodrug Monotherapy", Cancer Research, Mar. 1998, vol. 58, No. 6, pp. 1195-1201.

Bouhired, S. et al., "Biosynthesis of Phenylnannolone A, a Multidrug Resistance Reversal Agent from the Halotolerant Myxobacterium *Nannocystis pusilia* B150", ChemBioChem, Feb. 2014, vol. 15, No. 5, pp. 757-765 <DOI:10.1002/cbic.201300676>.

Bouvier, E. et al., "A new paclitaxel prodrug for use in ADEPT strategy", Organic & Biomolecular Chemistry, Aug. 2003, vol. 1, No. 19, pp. 3343-3352 <DOI:10.1039/B306236H>.

(56) References Cited

OTHER PUBLICATIONS

De Bont, D. et al., "Synthesis and biological activity of β-glucuronyl carbamate-based prodrugs of paclitaxel as potential candidates for ADEPT", Bioorganic & Medicinal Chemistry, Feb. 1997 (available online Mar. 1998), vol. 5, No. 2, pp. 405-414 <DOI:10.1016/S0968-0896(96)00249-0>.
Dewit, M. et al., "Design, synthesis, and cyclization of 4 aminobutyric acid derivatives: potential candidates as self-immolative spacers", Organic & Biomolecular Chemistry, Jan. 2011, vol. 9, No. 6, pp. 1846-1854 <DOI:10.1039/C0OB00890G>.
Du, F-Y. et al., "Cyclohexadepsipeptides of the Isaridin Class from the Marine-Derived Fungus *Beauveria felina* EN-135", Journal of Natural Products, May 2014 (available online Apr. 2014), vol. 77, No. 5, pp. 1164-1169 <DOI:10.1021/np4011037>.
Dudley, T., "Ethanol, Fruit Ripening, and the Historical Origins of Human Alcoholism in Primate Frugivory", Integrative and Comparative Biology, 2004, vol. 44, pp. 315-323.
Duimstra, J. et al., "A Gadolinium Chelate for Detection of β3-Glucuronidase: A Self-Immolative Approach", Journal of the American Chemical Society, Sep. 2005 (available online Aug. 2005), vol. 127, No. 37, pp. 12847-12855 <DOI:10.1021/ja042162r>.
Felder, S. et al., "Salimyxins and Enhygrolides: Antibiotic, Sponge-Related Metabolites from the Obligate Marine Myxobacterium *Enhygromyxa salina*", ChemBioChem, Jul. 2013 (available online Jun. 2013), vol. 14, No. 11, pp. 1363-1371 <DOI:10.1002/cbic.201300268>.
Fu, P. et al., "Carpatamides A-C, Cytotoxic Arylamine Derivatives from a Marine-Derived *Streptomyces* sp.", Journal of Natural Products, May 2014 (available online Apr. 2014), vol. 77, No. 5, pp. 1245-1248 <DOI:10.1021/np500207p>.
Glueck, S. et al., "Biocatalytic Racemization of Aliphatic, Arylaliphatic, and Aromatic α-Hydroxycarboxylic Acids", The Journal of Organic Chemistry, May 2005 (available online Apr. 2005), vol. 70, No. 10, pp. 4028-4032 <DOI:10.1021/io050156n>.
Grinda, M. et al., "A Heterodimeric Glucuronide Prodrug for Cancer Tritherapy: the Double Role of the Chemical Amplifier", ChemMedChem, Dec. 2011 (available online Aug. 2011), vol. 6, No. 12, pp. 2137-2141 <DOI:10.1002/cmdc.201100355>.
Guo, W. et al., "Sorbicillamines A-E, Nitrogen-Containing Sorbicillinoidsfrom the Deep-Sea-Derived Fungus *Penicillium* sp. F23-2", Journal of Natural Products, Nov. 2013, vol. 76, No. 11, pp. 2106-2112 <DOI:10.1021/np4006647>.
Haga, A. et al., "Pyridone Alkaloids from a Marine-Derived Fungus, *Stagonosporopsis cucurbitacearum*, and Their Activities against Azole-Resistant Candida albicans", Journal of Natural Products, Apr. 2013 (available online Mar. 2013), vol. 76, No. 4, pp. 750-754 <DOI:10.1021/np300876t>.
Halsey, C. et al., "Influence of the lipid environment on valinomycin structure and cation complex formation", Spectrochimica Acta Part A: Molecular and Biomolecular Spectroscopy, Oct. 2012 (available online May 2012), vol. 96, pp. 200-206 <DOI:10.1016/j.saa.2012.05.022>.
He, F. et al., "Asperterrestide A, a Cytotoxic Cyclic Tetrapeptide from the Marine-Derived Fungus *Aspergillus terreus* SCSGAF0162", Journal of Natural Products, Jun. 2013, vol. 76, No. 6, pp. 1182-1186 <DOI:10.1021/np300897v>.
Houba, P. et al., "A novel doxorubicin-glucuronide prodrug DOX-GA3 for tumour-selective chemotherapy: distribution and efficacy in experimental human ovarian cancer", British Journal of Cancer, Feb. 2001, vol. 84, No. 4, pp. 550-557 <DOI:10.1054/bjoc.2000.1640>.
Jacobazzi, R. et al., "Antitumor Potential of Conjugable Valinomycins Bearing Hydroxyl Sites: In Vitro Studies", ACS Medicinal Chemistry Letters, Dec. 2013 (available online Oct. 2013), vol. 4, No. 12, pp. 1189-1192 <DOI:10.1021 /ml400300q>.
Jaitzig, J. et al., "Reconstituted Biosynthesis of the Nonribosomal Macrolactone Antibiotic Valinomycin in *Escherichia coli*", ACS Synthetic Biology, 2014 (available online Dec. 2013), vol. 3, No. 7, pp. 432-438 <DOI:10.1021/sb400082j>.

Jang, K. et al., "Anthracimycin, a Potent Anthrax Antibiotic from a Marine-Derived Actinomycete", Angewandte Chemie International Edition, Jul. 2013 (available online Jun. 2013), vol. 52, No. 30, pp. 7822-7824 <DOI:10.1002/anie.201302749>.
Kong, F. et al., "Thiodiketopiperazines from the Marine-Derived Fungus *Phoma* sp. OUCMDZ-1847", Journal of Natural Products, Jan. 2014 (available online Dec. 2013), vol. 77, No. 1, pp. 132-137 <DOI:10.1021/np400802d>.
Kuisle, O. et al., "A General Methodology for Automated Solid-Phase Synthesis of Depsides and Depsipeptides. Preparation of a Valinomycin Analogue", The Journal of Organic Chemistry, Oct. 1999, vol. 64, No. 22, pp. 3063-8075 <DOI:10.1021 /jo981580+>.
Kuramochi, K. et al., "Synthesis, Structure, and Cytotoxicity Studies of Some Fungal Isochromanes", Journal of Natural Products, Sep. 2013, vol. 76, No. 9, pp. 1737-1745 <DOI:10.1021/np400460m>.
Leeson, P. et al., "The influence of drug-like concepts on decision-making in medicinal chemistry", Nature Reviews Drug Discovery, Nov. 2007, vol. 6, pp. 881-890 <DOI:10.1038/nrd2445>.
Legigan, T. et al., "Synthesis and Antitumor Efficacy of a β-Glucuronidase-Responsive Albumin-Binding Prodrug of Doxorubicin", Journal of Medicinal Chemistry, May 2012 (available online Apr. 2012), vol. 55, No. 9, pp. 4516-4520 <DOI:10.1021/jm300348r>.
Legigan, T. et al., "Synthesis and biological evaluations of a monomethylauristatin E glucuronide prodrug for selective cancer chemotherapy", European Journal of Medicinal Chemistry, Sep. 2013 (available online Jun. 2013), vol. 67, pp. 75-80 <DOI:10.1016/j.ejmech.2013.06.037>.
Lin, Z. et al., "Structure and activity of lobophorins from a turrid mollusk-associated *Streptomyces* sp", The Journal of Antibiotics, 2014 (available online Nov. 2013), vol. 67, pp. 121-126 <DOI:10.1038/ja.2013.115>.
Lu, Z. et al., "Plakinamine M, a Steroidal Alkaloid from the Marine Sponge *Corticium* sp.", Journal of Natural Products, Nov. 2013, vol. 76, No. 11, pp. 2150-2152 <DOI:10.1021/np400649e>.
Meng, L-H. et al., "Sulfur-Containing Cytotoxic Curvularin Macrolides from *Penicillium sumatrense* MA-92, a Fungus Obtained from the Rhizosphere of the Mangrove *Lumnitzera racemosa*", Journal of Natural Products, Nov. 2013, vol. 76, No. 11, pp. 2145-2149 <DOI:10.1021/np400614f>.
Monks, A. et al., "Feasibility of a High-Flux Anticancer Drug Screen Using a Diverse Panel of Cultured Human Tumor Cell Lines", Journal of the National Cancer Institute, Jun. 1991, vol. 83, No. 11, pp. 757-766 <DOI:10.1093/inci/83.11.757>.
Myyobatake, Y. et al., "Cytotoxic Alkylated Hydroquinone, Phenol, and Cyclohexenone Derivatives from Aspergillus violaceofuscus Gasperini", Journal of Natural Products, May 2014, vol. 77, No. 5, pp. 1236-1240 <DOI:10.1021/np401017g>.
NCCLS., "Methods for Dilution Antimicrobial Susceptibility Tests for Bacteria That Grow Aerobically; Approved Standard—Seventh Edition", Clinical and Laboratory Standards Institute, 2006, NCCLS document M7-A7, 64 pages.
"NCCLS., ""Reference Method for Broth Dilution Antifungal Susceptibility Testingof Yeasts; Approved Standard—Second Edition"", Clinical and Laboratory Standards Institute, 2002, NCCLS document M27-A2, 51 pages."
Patent Cooperation Treaty, International Searching Authority, International Preliminary Report on Patentability and Written Opinion for PCT/US2016/017834, 9 pages, report dated Aug. 15, 2017, opinion dated May 2, 2016.
Patent Cooperation Treaty, International Searching Authority, International Search Report for PCT/US2016/017834, 3 pages, dated May 2, 2016.
Pavlik, C. et al., "Santacruzamate A, a Potent and Selective Histone Deacetylase Inhibitor from the Panamanian Marine Cyanobacterium cf. *Symploca* sp.", Journal of Natural Products, Nov. 2013 (available online Oct. 2013), vol. 76, No. 11, pp. 2026-2033 <DOI:10.1021/np400198r>.
Peng, J. et al., "Alkaloids from the Deep-Sea-Derived Fungus *Aspergillus westerdijkiae* DFFSCS013", Journal of Natural Products, May 2013 (available online Apr. 2013), vol. 76, No. 5, pp. 983-987 <DOI:10.1021/np400132m>.

(56) References Cited

OTHER PUBLICATIONS

Pettit, G. et al., "Antineoplastic Agents. 570. Isolation and Structure Elucidation of Bacillistatins 1 and 2 from a Marine Bacillus Silvestris", Journal of Natural Products, Mar. 2009 (available online Feb. 2009), vol. 72, No. 3, pp. 366-371 <DOI:10.1021/np800603u>.

Pettit, G. et al., "Antineoplastic Agents. 571. Total Synthesis of Bacillistatin 2", Journal of Natural Products, Mar. 2009 (available online Feb. 2009), vol. 72, No. 3, pp. 372-379 <DOI:10.1021/np800607x>.

Pettit, G. et al., "Antineoplastic Agents. 600. From the South Pacific Ocean to the Silstatins", Journal of Natural Products, Mar. 2015 (available online Feb. 2015), vol. 78, No. 3, pp. 510-523 <DOI:10.1021/np501004h>.

Pettit, G. et al., "Antineoplastic agents. Part 409: Isolation and structure of montanastatin from a terrestrial actinomycete", Bioorganic & Medicinal Chemistry, May 1999, vol. 7, No. 5, pp. 895-899 <DOI:10.1016/S0968-0896(99)00024-3>.

Pettit, R., "Culturability and Secondary Metabolite Diversity of Extreme Microbes: Expanding Contribution of Deep Sea and Deep-Sea Vent Microbes to Natural Product Discovery", Marine Biotechnology, Feb. 2011 (available online May 2010), vol. 13, No. 1, pp. 1-11 <DOI:10.1007/s10126-010-9294-y>.

Seattle Genetics Inc., "Highlights of Prescribing Information", Federal Drug Administration, Aug. 2011, 15 pages.

Skellam, E. et al., "Identification of micromonolactam, a new polyene macrocyclic lactam from two marine Micromonospora strains using chemical and molecular methods: clarification of the biosynthetic pathway from a glutamate starter unit", The Journal of Antibiotics, May 2013, vol. 66, pp. 431-441 <DOI:10.1038/ja.2013.34>.

Sun, Y-L. et al., "Cytotoxic Dihydrothiophene-Condensed Chromones from the Marine-Derived Fungus *Penicillium oxalicum*". Planta Medica, 2013, vol. 79, No. 15, pp. 1474-1479 <DOI:10.1055/s-0033-1350805>.

Suwan, S. et al., "Structure of cereulide, a cyclic dodecadepsipeptide toxin from Bacillus cereus and studies on NMR characteristics of its alkali metal complexes including a conformational structure of the K+ complex", Journal of the Chemical Society Perking Transactions 1, 1995, No. 7, pp. 765-775 <DOI:10.1039/P19950000765>.

Tan, L., "Pharmaceutical agents from filamentous marine cyanobacteria", Drug Discovery Today, Sep. 2013 (available online May 2013), vol. 18, No. 17-18, pp. 863-871 <DOI:10.1016/j.drudis.2013.05.010>.

Thornburg, C. et al., "Aprataxin H and Aprataxin A Sulfoxide from the Red Sea Cyanobacterium *Moorea producens*", Journal of Natural Products, Sep. 2013, vol. 76, No. 9, pp. 1781-1788 <DOI:10.1021/np4004992>.

Um, S. et al., "Ohmyungsamycins A and B: Cytotoxic and Antimicrobial Cyclic Peptides Produced by *Streptomyces* sp. from a Volcanic Island", The Journal of Organic Chemistry, Dec. 2013 (available online Nov. 2013), vol. 78, No. 24, p. 12321-12329 <DOI:10.1021/jo401974g>.

Um, S. et al., "Sungsanpin, a Lasso Peptide from a Deep-Sea Streptomycete", Journal of Natural Products, May 2013, vol. 76, No. 5, pp. 873-879 <DOI:10.1021/np300902g>.

Woessner, R. et al., "Comparison of three approaches to doxorubicin therapy: free doxorubicin, liposomal doxorubicin, and beta-glucuronidase-activated prodrug (HMR 1826)", Anticancer Research, Jul.-Aug. 2000, vol. 20, No. 4, pp. 2289-2296.

Wu, C. et al., "Identification of Elaiophylin Derivatives from the Marine-Derived Actinomycete *Streptomyces* sp. 7-145 Using PCR-Based Screening", Journal of Natural Products, Nov. 2013 (available online Oct. 2013), vol. 76, No. 11, pp. 2153-2157 <DOI:10.1021/np4006794>.

Wu, G. et al., "Cladosins A-E, Hybrid Polyketides from a Deep-Sea-Derived Fungus, *Cladosporium sphaerospermum*", Journal of Natural Products, Feb. 2014, vol. 77, No. 2, pp. 270-275 <DOI:10.1021/np400833x>.

Xu, D-X. et al., "Polyhydroxy Cyclohexanols from a *Dendrodochium* sp. Fungus Associated with the Sea Cucumber *Holothuria nobilis* Selenka", Journal of Natural Products, May 2014 (available online Apr. 2014), vol. 77, No. 5, pp. 1179-1184 <DOI:10.1021/np500024r>.

Office Action dated Feb. 8, 2019 in U.S. Appl. No. 15/550,727.
Office Action dated Apr. 20, 2018 in U.S. Appl. No. 15/550,727.
Office Action dated Jul. 27, 2018 in U.S. Appl. No. 15/550,727.

Keepers, Y.P., et al., "Comparison of the Sulforhodamine B Protein and Tetrazolium (MTT) Assays for In Vitro Chemosensitivity Testing", In the European Journal of Cancer and Clinical Oncology, vol. 27, No. 7, Jul. 1991, pp. 897-900.

Rubinstein, L.V., et al., "Comparison of In Vitro Anticancer-Drug-Screening Data Generated with a Tetrazolium Assay Versus a Protein Assay against a Diverse Panel of Human Tumor Cell Lines", in the Journal of the National Cancer Institute, vol. 82, No. 13, Jul. 1990, pp. 1113-1118.

Vajrabhaya, L. and Korsuwannawong, S., "Cytotoxicity Evaluation of a Thai Herb using Tetrazolium (MTT) and Sulforhodamine B (SRB) Assays", In the Journal of Analytical Science and Technology, Jul. 2018, pp. 1-6.

* cited by examiner

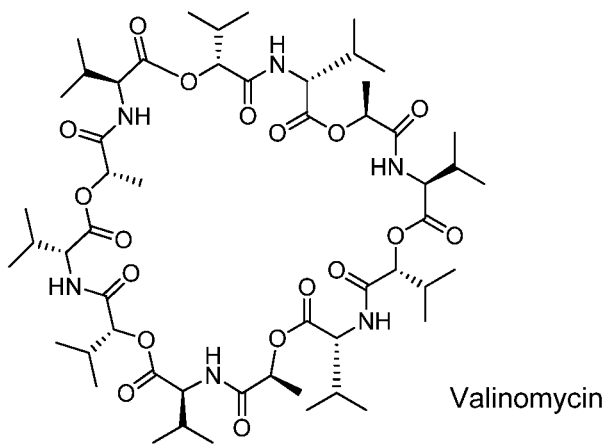
Valinomycin
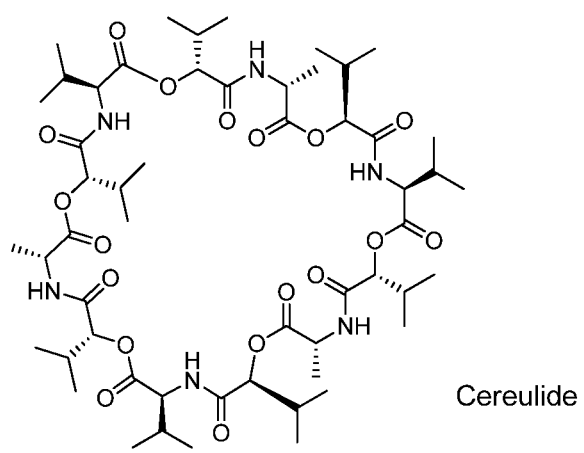
Cereulide
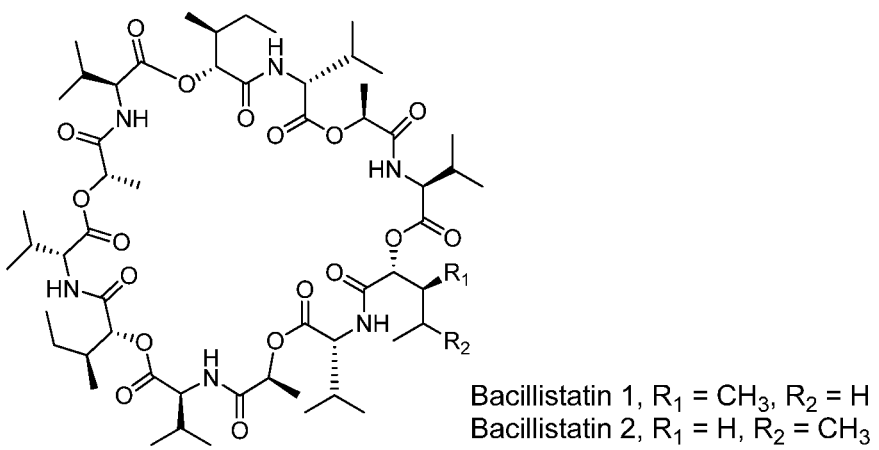
Bacillistatin 1, R₁ = CH₃, R₂ = H
Bacillistatin 2, R₁ = H, R₂ = CH₃

SILSTATIN COMPOUNDS

FEDERALLY SPONSORED RESEARCH OR DEVELOPMENT

This invention was made with government support under R01 CA090441 awarded by the National Institutes of Health. The government has certain rights in the invention.

BACKGROUND OF THE INVENTION

In 2009 Pettit et al. reported the isolation and structures of two very potent cancer cell growth inhibitors, cyclodepsipeptides designated bacillistatins 1 and 2[1,2] from *Bacillus silvestris* carried by a South Pacific (Chile) crab. Subsequently, Pettit et al. completed the total synthesis of bacillistatin 2.[2] Meanwhile, the promise of marine derived microorganisms as productive sources of new anticancer and antiproliferative drugs continues to expand. Recent examples includes discoveries of marine microorganisms containing small molecule cancer cell growth inhibitors,[3a-h] antibiotics from bacteria,[4a-f] antibiotics from fungi,[5a-f] various inhibitors from cyanobacteria[6a-c] and the increasing potential of deep-sea microorganisms.[7a-d] Structurally, the bacillistatins are similar to valinomycin, a well-known antibiotic and cytotoxic cyclodepsipeptide that acts as a carrier-type potassium ionophore (FIG. 1). Another cyclic depsipeptide that resembles the structures of valinomycin and bacillistatins is cereulide, a toxin isolated in 1995 from *Bacillus cereus*.[8]

The cancer cell growth inhibition values for these molecules are in the order of $10^{-4}$-$10^{-5}$ μg/mL which makes them good candidates as therapeutic agents for cancer treatment and specially when linked to monoclonal antibodies. That is a powerful technique to reduce side effects and increase selectivity as well as other targeting systems that allow the release of the drug, from a non-toxic precursor (prodrug), in the solid tumors microenvironment or inside the cancer cells. One of the major obstacles for this approach with the bacillistatins is the lack of easily derivatizable groups (e. g. —$NH_2$, —SH, —OH, —COOH, etc) necessary for conjugation of these $K^+$ ionophores.

Accordingly, there is a need to provide new bacillistatin compounds (designated Silstatin compounds) that have suitable cancer cell growth inhibition values and antibacterial activities and that contain an easily derivatizable group for conjugation to monoclonal antibodies.

Citation of any reference in this section is not to be construed as an admission that such reference is prior art to the present disclosure.

BRIEF SUMMARY OF THE INVENTION

The present disclosure relates to Silstatin compounds, pharmaceutical compositions comprising such compounds, kits, and methods for using such compounds or pharmaceutical compositions. The compounds of the present disclosure contain an easily derivatizable group for conjugation to monoclonal antibodies. The compounds have, or are believed to have, suitable cancer cell growth inhibition values and antibacterial activities.

In a first embodiment, the present disclosure provides a compound of formula (I):

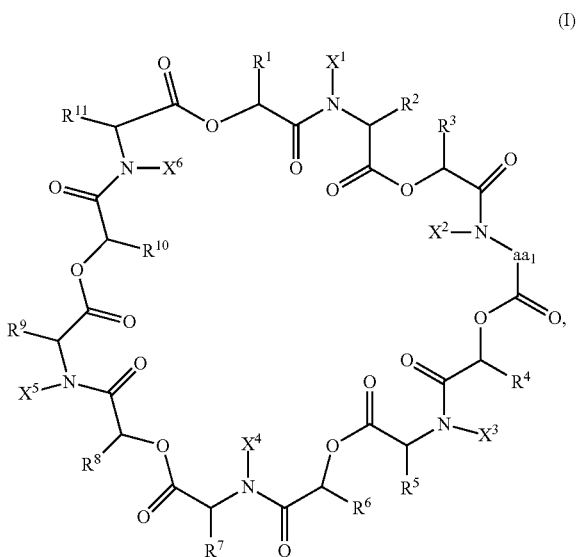

or a pharmaceutically acceptable salt thereof, wherein
$R^1$, $R^2$, $R^3$, $R^4$, $R^5$, $R^6$, $R^7$, $R^8$, $R^9$, $R^{10}$ and $R^{11}$ are independently selected from —($C_1$-$C_6$)alkyl, —($C_2$-$C_6$)alkenyl and —($C_2$-$C_6$)alkynyl, wherein the alkyl, alkenyl or alkynyl are unsubstituted or substituted with a substituent selected from —OH, —$NH_2$, —NHR', —NHR'R", —SH, —SR', —C(O)OH, —C(O)$NH_2$, —C(O)NHR', —C(O)NR'R", —NHC(=NH)$NH_2$, —($C_6$-$C_{14}$)aryl, —($C_6$-$C_{14}$)aryl substituted with OH, -(5- or 6-membered monocyclic heteroaryl), -(9- or 10-membered bicyclic heteroaryl) and —($C_3$-$C_7$)cycloalkyl, wherein R' and R" are independently selected from —($C_1$-$C_6$)alkyl, —($C_2$-$C_6$)alkenyl and ($C_2$-$C_6$)alkynyl; or wherein the alkyl, taken together with an adjacent N, forms a (5- or 6-membered)heterocyclyl;

$X^1$, $X^2$, $X^3$, $X^4$, $X^5$ and $X^6$ are independently selected from —H, ($C_1$-$C_6$)alkyl, —($C_2$-$C_6$)alkenyl and —($C_2$-$C_6$)alkynyl;

and $aa_1$ is an amino acid, wherein the amino acid is unsubstituted or substituted with a protecting group or a Linking Unit.

In a second embodiment, the present disclosure provides a compound of formula (II), (II)

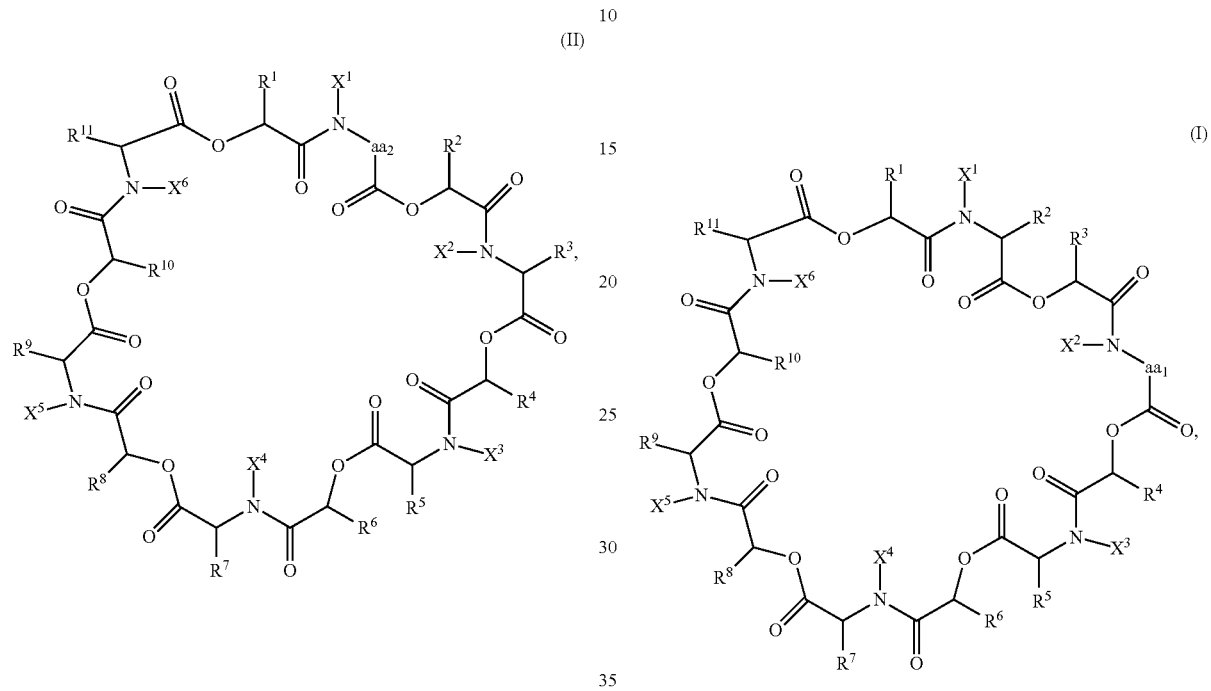

or a pharmaceutically acceptable salt thereof, wherein
$R^1$, $R^2$, $R^3$, $R^4$, $R^5$, $R^6$, $R^7$, $R^8$, $R^9$, $R^{10}$ and $R^{11}$ are independently selected from —($C_1$-$C_6$)alkyl, —($C_2$-$C_6$)alkenyl and —($C_2$-$C_6$)alkynyl, wherein the alkyl, alkenyl or alkynyl are unsubstituted or substituted with a substituent selected from —OH, —$NH_2$, —NHR', —NHR'R", —SH, —SR', —C(O)OH, —C(O)$NH_2$, —C(O)NHR', —C(O)NR'R", —NHC(=NH)$NH_2$, —($C_6$-$C_{14}$)aryl, —($C_6$-$C_{14}$)aryl substituted with OH, -(5- or 6-membered monocyclic heteroaryl), -(9- or 10-membered bicyclic heteroaryl) and —($C_3$-$C_7$)cycloalkyl, wherein R' and R" are independently selected from —($C_1$-$C_6$)alkyl, —($C_2$-$C_6$)alkenyl and ($C_2$-$C_6$)alkynyl; or wherein the alkyl, taken together with an adjacent N, forms a (5- or 6-membered)heterocyclyl;

$X^1$, $X^2$, $X^3$, $X^4$, $X^5$ and $X^6$ are independently selected from —H, ($C_1$-$C_6$)alkyl, —($C_2$-$C_6$)alkenyl and —($C_2$-$C_6$)alkynyl;

$aa_2$ is an amino acid, wherein the amino acid is unsubstituted or substituted with a protecting group or a Linking Unit.

BRIEF DESCRIPTION OF FIGURES

FIG. 1 shows the structures of valinomycin, cereulide, bacillistatin 1 and bacillistatin 2.

DETAILED DESCRIPTION OF THE INVENTION

The invention includes the following:
(1.) A compound of formula (I), (I)

or a pharmaceutically acceptable salt thereof, wherein
$R^1$, $R^2$, $R^3$, $R^4$, $R^5$, $R^6$, $R^7$, $R^8$, $R^9$, $R^{10}$ and $R^{11}$ are independently selected from —($C_1$-$C_6$)alkyl, —($C_2$-$C_6$)alkenyl and —($C_2$-$C_6$)alkynyl, wherein the alkyl, alkenyl or alkynyl are unsubstituted or substituted with a substituent selected from —OH, —$NH_2$, —NHR', —NHR'R", —SH, —SR', —C(O)OH, —C(O)$NH_2$, —C(O)NHR', —C(O)NR'R", —NHC(=NH)$NH_2$, —($C_6$-$C_{14}$)aryl, —($C_6$-$C_{14}$)aryl substituted with OH, -(5- or 6-membered monocyclic heteroaryl), -(9- or 10-membered bicyclic heteroaryl) and —($C_3$-$C_7$)cycloalkyl, wherein R' and R" are independently selected from —($C_1$-$C_6$)alkyl, —($C_2$-$C_6$)alkenyl and ($C_2$-$C_6$)alkynyl; or wherein the alkyl, taken together with an adjacent N, forms a (5- or 6-membered)heterocyclyl;

$X^1$, $X^2$, $X^3$, $X^4$, $X^5$ and $X^6$ are independently selected from —H, ($C_1$-$C_6$)alkyl, —($C_2$-$C_6$)alkenyl and —($C_2$-$C_6$)alkynyl;

and $aa_1$ is an amino acid, wherein the amino acid is unsubstituted or substituted with a protecting group or a Linking Unit.

(2.) A compound of formula (II),

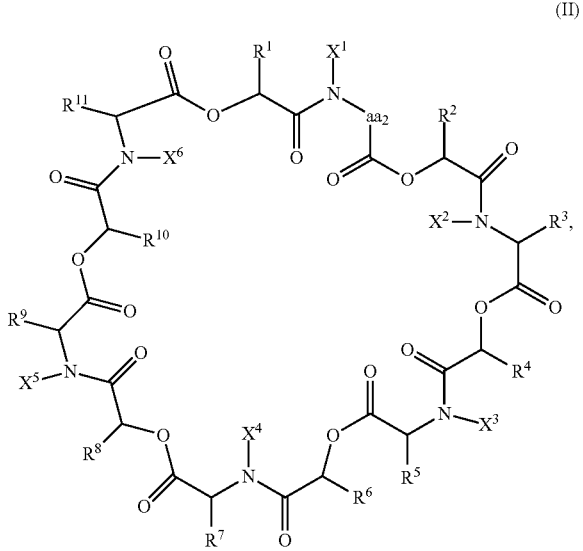

(II)

or a pharmaceutically acceptable salt thereof, wherein
$R^1$, $R^2$, $R^3$, $R^4$, $R^5$, $R^6$, $R^7$, $R^8$, $R^9$, $R^{10}$ and $R^{11}$ are independently selected from —$(C_1$-$C_6)$alkyl, —$(C_2$-$C_6)$alkenyl and —$(C_2$-$C_6)$alkynyl,
  wherein the alkyl, alkenyl or alkynyl are unsubstituted or substituted with a substituent selected from —OH, —$NH_2$, —NHR', —NHR'R", —SH, —SR', —C(O)OH, —C(O)$NH_2$, —C(O)NHR', —C(O)NR'R", —NHC(=NH)$NH_2$, —$(C_6$-$C_{14})$aryl, —$(C_6$-$C_{14})$aryl substituted with OH, -(5- or 6-membered monocyclic heteroaryl), -(9- or 10-membered bicyclic heteroaryl) and —$(C_3$-$C_7)$cycloalkyl, wherein R' and R" are independently selected from —$(C_1$-$C_6)$alkyl, —$(C_2$-$C_6)$alkenyl and $(C_2$-$C_6)$alkynyl; or
  wherein the alkyl, taken together with an adjacent N, forms a (5- or 6-membered)heterocyclyl;
$X^1$, $X^2$, $X^3$, $X^4$, $X^5$ and $X^6$ are independently selected from —H, $(C_1$-$C_6)$alkyl, —$(C_2$-$C_6)$alkenyl and —$(C_2$-$C_6)$alkynyl;
$aa_2$ is an amino acid, wherein the amino acid is unsubstituted or substituted with a protecting group or a Linking Unit.

(3.) The compound of the above (1.) or (2.), wherein at least one of $R^1$, $R^4$, and $R^8$ is $(C_1$-$C_6)$alkyl.

(4.) The compound of the above (1.) or (2.), wherein at least two of $R^1$, $R^4$, and $R^8$ are $(C_1$-$C_6)$alkyl.

(5.) The compound of the above (1.) or (2.), wherein each of $R^1$, $R^4$, and $R^8$ is $(C_1$-$C_6)$alkyl.

(6.) The compound of the above (1.) or (2.), wherein at least one of $R^1$, $R^4$, and $R^8$ is $(C_1$-$C_4)$alkyl.

(7.) The compound of the above (1.) or (2.), wherein at least two of $R^1$, $R^4$, and $R^8$ are $(C_1$-$C_4)$alkyl.

(8.) The compound of the above (1.) or (2.), wherein each of $R^1$, $R^4$, and $R^8$ is $(C_1$-$C_4)$alkyl.

(9.) The compound of the above (1.) or (2.), wherein at least one of $R^1$, $R^4$, and $R^8$ is $(C_4)$alkyl.

(10.) The compound of the above (1.) or (2.), wherein at least two of $R^1$, $R^4$, and $R^8$ are $(C_4)$alkyl.

(11.) The compound of the above (1.) or (2.), wherein each of $R^1$, $R^4$, and $R^8$ is $(C_4)$alkyl.

(12.) The compound of the above (1.) or (2.), wherein at least one of $R^1$, $R^4$, and $R^8$ is $(C_1$-$C_6)$alkyl substituted with $(C_3$-$C_7)$cycloalkyl.

(13.) The compound of the above (1.) or (2.), wherein at least two of $R^1$, $R^4$, and $R^8$ are $(C_1$-$C_6)$alkyl substituted with $(C_3$-$C_7)$cycloalkyl.

(14.) The compound of the above (1.) or (2.), wherein each of $R^1$, $R^4$, and $R^8$ is $(C_1$-$C_6)$alkyl substituted with $(C_3$-$C_7)$cycloalkyl.

(15.) The compound of the above (1.) or (2.), wherein at least one of $R^1$, $R^4$, and $R^8$ is $(C_1$-$C_3)$alkyl substituted with $(C_3$-$C_7)$cycloalkyl.

(16.) The compound of the above (1.) or (2.), wherein at least two of $R^1$, $R^4$, and $R^8$ are $(C_1$-$C_3)$alkyl substituted with $(C_3$-$C_7)$cycloalkyl.

(17.) The compound of the above (1.) or (2.), wherein each of $R^1$, $R^4$, and $R^8$ is $(C_1$-$C_3)$alkyl substituted with $(C_3$-$C_7)$cycloalkyl.

(18.) The compound of the above (1.) or (2.), wherein at least one of $R^1$, $R^4$, and $R^8$ is $(C_1)$alkyl substituted with $(C_3$-$C_7)$cycloalkyl.

(19.) The compound of the above (1.) or (2.), wherein at least two of $R^1$, $R^4$, and $R^8$ are $(C_1)$alkyl substituted with $(C_3$-$C_7)$cycloalkyl.

(20.) The compound of the above (1.) or (2.), wherein each of $R^1$, $R^4$, and $R^8$ is $(C_1)$alkyl substituted with $(C_3$-$C_7)$cycloalkyl.

(21.) The compound of the above (1.) or (2.), wherein at least one of $R^1$, $R^4$, and $R^8$ is $(C_1$-$C_6)$alkyl substituted with $(C_6)$cycloalkyl.

(22.) The compound of the above (1.) or (2.), wherein at least two of $R^1$, $R^4$, and $R^8$ are $(C_1$-$C_6)$alkyl substituted with $(C_6)$cycloalkyl.

(23.) The compound of the above (1.) or (2.), wherein each of $R^1$, $R^4$, and $R^8$ is $(C_1$-$C_6)$alkyl substituted with $(C_6)$cycloalkyl.

(24.) The compound of the above (1.) or (2.), wherein at least one of $R^1$, $R^4$, and $R^8$ is $(C_1$-$C_3)$alkyl substituted with $(C_6)$cycloalkyl.

(25.) The compound of the above (1.) or (2.), wherein at least two of $R^1$, $R^4$, and $R^8$ are $(C_1$-$C_3)$alkyl substituted with $(C_6)$cycloalkyl.

(26.) The compound of the above (1.) or (2.), wherein each of $R^1$, $R^4$, and $R^8$ is $(C_1$-$C_3)$alkyl substituted with $(C_6)$cycloalkyl.

(27.) The compound of the above (1.) or (2.), wherein at least one of $R^1$, $R^4$, and $R^8$ is $(C_1)$alkyl substituted with $(C_6)$cycloalkyl.

(28.) The compound of the above (1.) or (2.), wherein at least two of $R^1$, $R^4$, and $R^8$ are $(C_1)$alkyl substituted with $(C_6)$cycloalkyl.

(29.) The compound of the above (1.) or (2.), wherein each of $R^1$, $R^4$, and $R^8$ is $(C_1)$alkyl substituted with $(C_6)$cycloalkyl.

(30.) The compound of any one of the above (1.) to (29.), wherein each of $R^2$, $R^3$, $R^5$, $R^6$, $R^7$, $R^9$, $R^{10}$ and $R^{11}$ is independently $(C_1$-$C_3)$alkyl.

(31.) The compound of any one of the above (1.) to (30.), wherein each of $X^1$, $X^2$, $X^3$, $X^4$, $X^5$ and $X^6$ is independently H or $(C_1$-$C_6)$alkyl.

(32.) The compound of the above (31.), wherein each of $X^1$, $X^2$, $X^3$, $X^4$, $X^5$ and $X^6$ is H.

(33.) The compound of any one of the above (1.) to (32.), wherein one of $aa_1$ or $aa_2$ is valine.

(34.) The compound of any one of the above (1.) to (32.), wherein one of $aa_1$ or $aa_2$ is threonine optionally substituted with a protecting group or a Linking Unit.

(35.) The compound of any one of the above (1.) to (32.), wherein one of $aa_1$ or $aa_2$ is tyrosine optionally substituted with a protecting group or a Linking Unit.

(36.) The compound of the above (34.) or (35.), wherein the Linking Unit comprises a cleavable linker.

(37.) The compound of the above (36.), wherein the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage.

(38.) The compound of the above (37.), wherein the cleavable linker comprises a glycosidic bond, a hydrazone, a cathepsin-B-cleavable peptide, a disulfide or an ester bond.

(39.) The compound of the above (35.), wherein the cleavable linker comprises glucuronide.

(40.) The compound of the above (36.), wherein the Linking Unit is represented by formula (III):

$A_a\text{-}W_w\text{-}Y_y$ (III), wherein:
A is a Stretcher Unit;
a is 0 or 1,
each —W— is independently an Amino Acid Unit,
w is an integer ranging from 0 to 12,
Y is a Spacer Unit, and
y is 0, 1 or 2.

(41.) The compound of the above (40.), wherein $A_a$ is maleimidocaproyl.

(42.) The compound of the above (40.) or (41.), wherein $W_w$ is Valine-Citrulline.

(43.) The compound of any one of the above (40.) to (42.), wherein $Y_y$ is p-aminobenzyloxycarbonyl.

(44.) The compound of any one of the above (34.) to (36.) and (40.) to (43.), wherein the Linking Unit comprises a monoclonal antibody.

(45.) The compound of the above (1.), wherein the compound has formula (Ia):

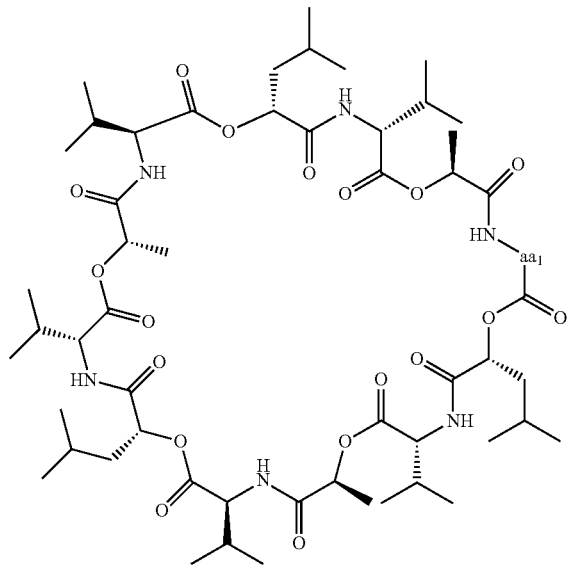

(Ia)

or a pharmaceutically acceptable salt thereof, wherein
aa$_1$ is valine, threonine optionally substituted with a protecting group or a Linking Unit, and tyrosine optionally substituted with a protecting group or a Linking Unit.

(46.) The compound of the above (45.), wherein aa$_1$ is valine.

(47.) The compound of the above (45.), wherein aa$_1$ is threonine optionally substituted with a protecting group or a Linking Unit.

(48.) The compound of the above (45.), wherein aa$_1$ is tyrosine optionally substituted with a protecting group or a Linking Unit.

(49.) The compound of the above (47.) or (48.), wherein the Linking Unit comprises a cleavable linker.

(50.) The compound of the above (49.), wherein the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage.

(51.) The compound of the above (49.), wherein the cleavable linker comprises a glycosidic bond, a hydrazone, a cathepsin-B-cleavable peptide, a disulfide or an ester bond.

(52.) The compound of the above (49.), wherein the cleavable linker comprises glucuronide.

(53.) The compound of the above (43.), wherein the Linking Unit is represented by formula (III):

$A_a\text{-}W_w\text{-}Y_y$ (III), wherein:
A is a Stretcher Unit;
a is 0 or 1,
each —W— is independently an Amino Acid Unit,
w is an integer ranging from 0 to 12,
Y is a Spacer Unit, and
y is 0, 1 or 2.

(54.) The compound of the above (53.), wherein $A_a$ is maleimidocaproyl.

(55.) The compound of the above (53.) or (54.), wherein $W_w$ is Valine-Citrulline.

(56.) The compound of any one of the above (53.) to (55.), wherein $Y_y$ is para-aminobenzyloxycarbonyl.

(57.) The compound of any one of the above (45.), (47.) to (49.) and (53.) to (56.), wherein the Linking Unit comprises a monoclonal antibody.

(58.) The compound of the above (1.), wherein the compound has formula (Ib):

(Ib)

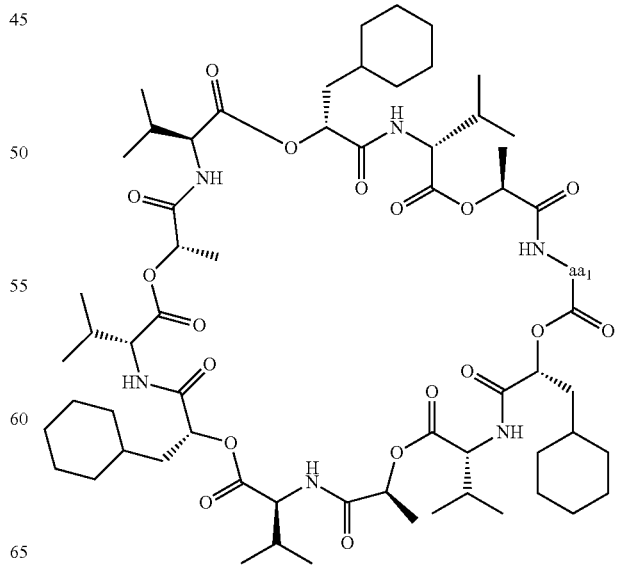

or a pharmaceutically acceptable salt thereof, wherein
aa$_1$ is valine, threonine optionally substituted with a protecting group or a Linking Unit, and tyrosine optionally substituted with a protecting group or a Linking Unit.

(59.) The compound of the above (58.), wherein aa$_1$ is valine.

(60.) The compound of the above (58.), wherein aa$_1$ is threonine optionally substituted with a protecting group or a Linking Unit.

(61.) The compound of the above (58.), wherein aa$_1$ is tyrosine optionally substituted with a protecting group or a Linking Unit.

(62.) The compound of the above (60.) or (61.), wherein the Linking Unit comprises a cleavable linker.

(63.) The compound of the above (62.), wherein the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage.

(64.) The compound of the above (62.), wherein the cleavable linker comprises a glycosidic bond, a hydrazone, a cathepsin-B-cleavable peptide, a disulfide or an ester bond.

(65.) The compound of the above (62.), wherein the cleavable linker comprises glucuronide.

(66.) The compound of the above (58.), wherein the Linking Unit is represented by formula (III):

$$A_a\text{-}W_w\text{-}Y_y \quad (III),$$

wherein:
A is a Stretcher Unit;
a is 0 or 1,
each —W— is independently an Amino Acid Unit,
w is an integer ranging from 0 to 12,
Y is a Spacer Unit, and
y is 0, 1 or 2.

(67.) The compound of the above (66.), wherein A$_a$ is maleimidocaproyl.

(68.) The compound of the above (66.) or (67.), wherein W$_w$ is Valine-Citrulline.

(69.) The compound of any one of the above (66.) to (68.), wherein Y$_y$ is para-aminobenzyloxycarbonyl.

(70.) The compound of any one of the above (58.), (60.) to (62.) and (66.) to (69.), wherein the Linking Unit comprises a monoclonal antibody.

(71.) The compound of the above (1.), wherein the compound has formula (Ic):

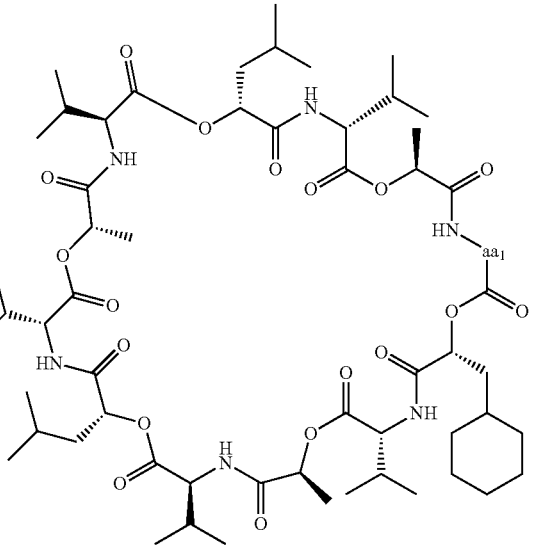

(Ic)

or a pharmaceutically acceptable salt thereof, wherein
aa$_1$ is valine, threonine optionally substituted with a protecting group or a Linking Unit, and tyrosine optionally substituted with a protecting group or a Linking Unit.

(72.) The compound of the above (71.), wherein aa$_1$ is valine.

(73.) The compound of the above (71.), wherein aa$_1$ is threonine optionally substituted with a protecting group or a Linking Unit.

(74.) The compound of the above (71.), wherein aa$_1$ is tyrosine optionally substituted with a protecting group or a Linking Unit.

(75.) The compound of the above (73.) or (74.), wherein the Linking Unit comprises a cleavable linker.

(76.) The compound of the above (75.), wherein the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage.

(77.) The compound of the above (75.), wherein the cleavable linker comprises a glycosidic bond, a hydrazone, a cathepsin-B-cleavable peptide, a disulfide or an ester bond.

(78.) The compound of the above (75.), wherein the cleavable linker comprises glucuronide.

(79.) The compound of the above (71.), wherein the Linking Unit is represented by formula (III):

$$A_a\text{-}W_w\text{-}Y_y \quad (III),$$

wherein:
A is a Stretcher Unit;
a is 0 or 1,
each —W— is independently an Amino Acid Unit,
w is an integer ranging from 0 to 12,
Y is a Spacer Unit, and
y is 0, 1 or 2.

(80.) The compound of the above (79.), wherein A$_a$ is maleimidocaproyl.

(81.) The compound of the above (79.) or (80.), wherein W$_w$ is Valine-Citrulline.

(82.) The compound of any one of the above (79.) to (81.), wherein Y$_y$ is para-aminobenzyloxycarbonyl.

(83.) The compound of any one of the above (71.), (73.) to (75.) and (79.) to (82.), wherein the Linking Unit comprises a monoclonal antibody.

(84.) The compound of the above (2.), wherein the compound has formula (IIa):

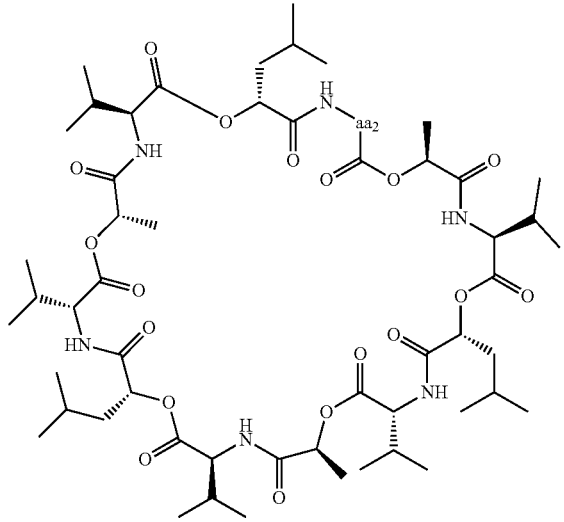

(IIa)

or a pharmaceutically acceptable salt thereof, wherein
aa$_2$ is valine, threonine optionally substituted with a protecting group or a Linking Unit, and tyrosine optionally substituted with a protecting group or a Linking Unit.

(85.) The compound of the above (84), wherein aa$_2$ is valine.

(86.) The compound of the above (84.), wherein aa$_2$ is threonine optionally substituted with a protecting group or a Linking Unit.

(87.) The compound of the above (84.), wherein aa$_2$ is tyrosine optionally substituted with a protecting group or a Linking Unit.

(88.) The compound of the above (86.) or (87.), wherein the Linking Unit comprises a cleavable linker.

(89.) The compound of the above (88.), wherein the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage.

(90.) The compound of the above (88.), wherein the cleavable linker comprises a glycosidic bond, a hydrazone, a cathepsin-B-cleavable peptide, a disulfide or an ester bond.

(91.) The compound of the above (88.), wherein the cleavable linker comprises glucuronide.

(92.) The compound of the above (84.), wherein the Linking Unit is represented by formula (III):

(III), wherein:
A is a Stretcher Unit;
a is 0 or 1,
each —W— is independently an Amino Acid Unit,
w is an integer ranging from 0 to 12,
Y is a Spacer Unit, and
y is 0, 1 or 2.

(93.) The compound of the above (92.), wherein A$_a$ is maleimidocaproyl.

(94.) The compound of the above (92.) or (93.), wherein W$_w$ is Valine-Citrulline.

(95.) The compound of any one of the above (92.) to (94.), wherein Y$_y$ is para-aminobenzyloxycarbonyl.

(96.) The compound of any one of the above (83.), (86.) to (88.) and (92.) to (95.), wherein the Linking Unit comprises a monoclonal antibody.

(97.) The compound of the above (1.), wherein the compound has formula (IIb):

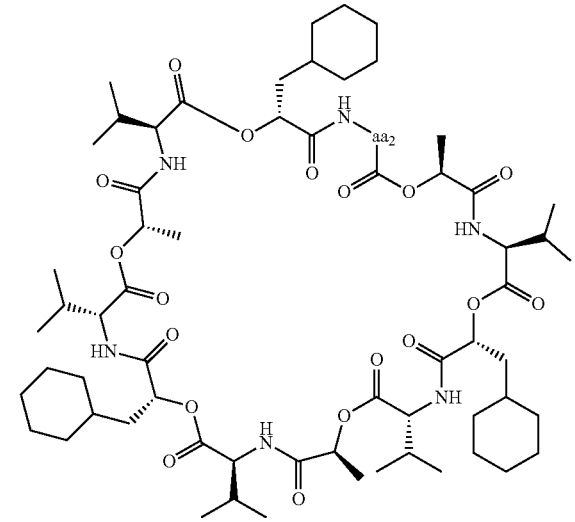

(IIb)

or a pharmaceutically acceptable salt thereof, wherein
aa$_2$ is valine, threonine optionally substituted with a protecting group or a Linking Unit, and tyrosine optionally substituted with a protecting group or a Linking Unit.

(98.) The compound of the above (97.), wherein aa$_2$ is valine.

(99.) The compound of the above (97.), wherein aa$_2$ is threonine optionally substituted with a protecting group or a Linking Unit.

(100.) The compound of the above (97.), wherein aa$_2$ is tyrosine optionally substituted with a protecting group or a Linking Unit.

(101.) The compound of the above (99.) or (100.), wherein the Linking Unit comprises a cleavable linker.

(102.) The compound of the above (101.), wherein the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage.

(103.) The compound of the above (101.), wherein the cleavable linker comprises a glycosidic bond, a hydrazone, a cathepsin-B-cleavable peptide, a disulfide or an ester bond.

(104.) The compound of the above (101.), wherein the cleavable linker comprises glucuronide.

(105.) The compound of the above (97.), wherein the Linking Unit is represented by formula (III):

(III), wherein:
A is a Stretcher Unit;
a is 0 or 1,
each —W— is independently an Amino Acid Unit,
w is an integer ranging from 0 to 12,
Y is a Spacer Unit, and
y is 0, 1 or 2.

(106.) The compound of the above (105.), wherein A$_a$ is maleimidocaproyl.

(107.) The compound of the above (105.) or (106.), wherein W$_w$ is Valine-Citrulline.

(108.) The compound of any one of the above (105.) to (107.), wherein Y$_y$ is para-aminobenzyloxycarbonyl.

(109.) The compound of any one of the above (97.), (99.) to (101.) and (105.) to (108.), wherein the Linking Unit comprises a monoclonal antibody.

(110.) The compound of the above (2.), wherein the compound has formula (IIc):

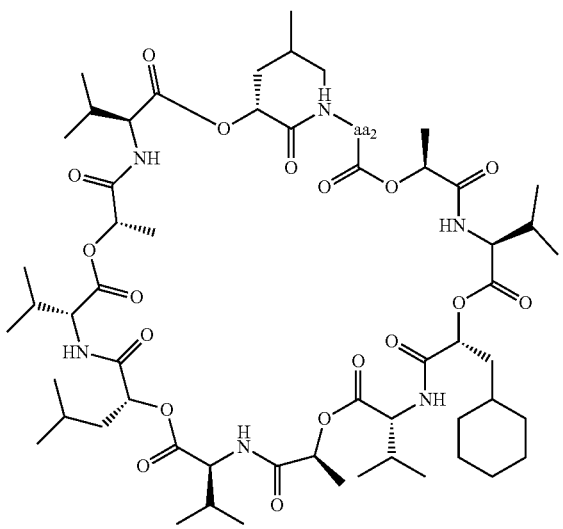

(IIc)

or a pharmaceutically acceptable salt thereof, wherein
aa$_2$ is valine, threonine optionally substituted with a protecting group or a Linking Unit, and tyrosine optionally substituted with a protecting group or a Linking Unit.

(111.) The compound of the above (110.), wherein aa$_2$ is valine.

(112.) The compound of the above (110.), wherein aa$_2$ is threonine optionally substituted with a protecting group or a Linking Unit.

(113.) The compound of the above (110.), wherein aa$_2$ is tyrosine optionally substituted with a protecting group or a Linking Unit.

(114.) The compound of the above (112.) or (113.), wherein the Linking Unit comprises a cleavable linker.

(115.) The compound of the above (114.), wherein the cleavable linker is cleavable by a method selected from the group consisting of: glycosidase-induced cleavage, acid-induced cleavage, light-induced cleavage, peptidase-induced cleavage, esterase-induced cleavage, and disulfide bond cleavage.

(116.) The compound of the above (114.), wherein the cleavable linker comprises a glycosidic bond, a hydrazone, a cathepsin-B-cleavable peptide, a disulfide or an ester bond.

(117.) The compound of the above (114.), wherein the cleavable linker comprises glucuronide.

(118.) The compound of the above (110.), wherein the Linking Unit is represented by formula (III):

$$A_a\text{-}W_w\text{-}Y_y \qquad (III),$$

wherein:
A is a Stretcher Unit;
a is 0 or 1,
each —W— is independently an Amino Acid Unit,
w is an integer ranging from 0 to 12,
Y is a Spacer Unit, and
y is 0, 1 or 2.

(119.) The compound of the above (118.), wherein A$_a$ is maleimidocaproyl.

(120.) The compound of the above (118.) or (119.), wherein W$_w$ is Valine-Citrulline.

(121.) The compound of any one of the above (118.) to (120.), wherein Y$_y$ is para-aminobenzyloxycarbonyl.

(122.) The compound of any one of the above (110.), (112.) to (114.) and (118.) to (121.), wherein the Linking Unit comprises a monoclonal antibody.

(123.) A compound selected from the group consisting of:
Cyclo-[Val-D-Hica-D-Val-Lac]$_3$;
Cyclo-{Thr-D-Hica-D-Val-Lac-[Val-D-Hica-D-Val-Lac]$_2$};
Cyclo-{Tyr-D-Hica-D-Val-Lac-[Val-D-Hica-D-Val-Lac]$_2$};
Cyclo-[Val-D-Hcha-D-Val-Lac]$_3$;
Cyclo-{Thr-D-Hcha-D-Val-Lac-[Val-D-Hcha-D-Val-Lac]$_2$};
Cyclo-{Tyr-D-Hcha-D-Val-Lac-[Val-D-Hcha-D-Val-Lac]$_2$};
Cyclo-{Thr-D-Hcha-D-Val-Lac-[Val-D-Hica-D-Val-Lac]$_2$};
Cyclo-{Tyr-D-Hcha-D-Val-Lac-[Val-D-Hica-D-Val-Lac]$_2$}; and
pharmaceutically acceptable salts thereof.

(124.) A compound, which is:

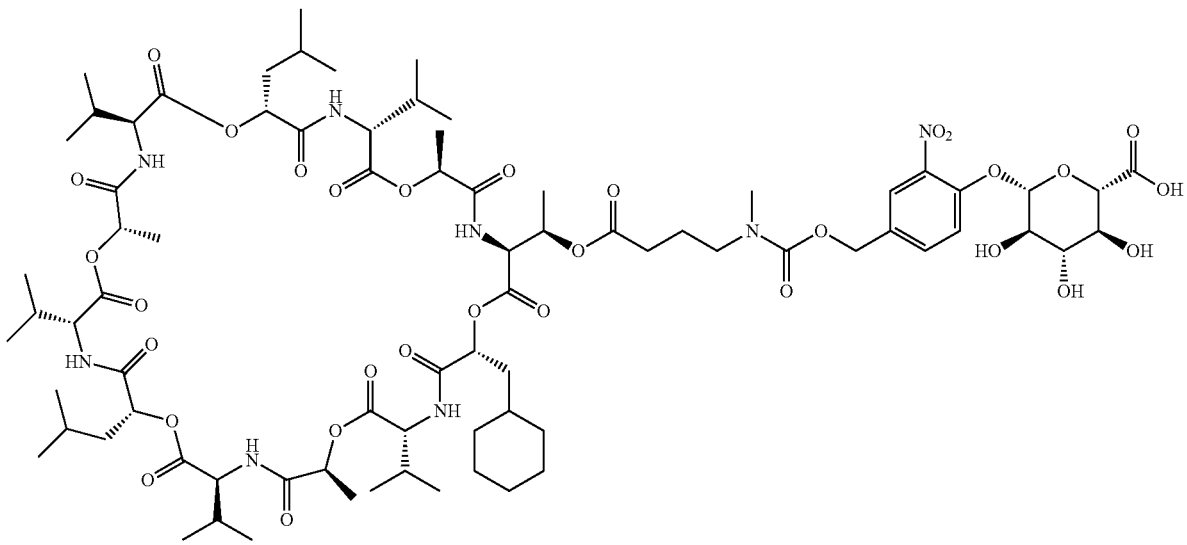 [SMILES: CC(C)C[C@H]1OC(=O)[C@H](C(C)C)NC(=O)[C@H](C)OC(=O)[C@@H](C(C)C)NC(=O)[C@@H](CC2CCCCC2)OC(=O)[C@H]([C@@H](C)OC(=O)CCCN(C)C(=O)OCc2ccc(O[C@@H]3O[C@H](C(=O)O)[C@@H](O)[C@H](O)[C@H]3O)c([N+](=O)[O-])c2)NC(=O)[C@H](C)OC(=O)[C@@H](C(C)C)NC(=O)[C@@H](CC(C)C)OC(=O)[C@H](C(C)C)NC(=O)[C@H](C)OC(=O)[C@@H](C(C)C)NC1=O]

and a pharmaceutically acceptable salt thereof.

(125.) A pharmaceutical composition comprising a compound of any one of the above (1.) to (124.) or a pharmaceutically acceptable salt thereof and a pharmaceutically acceptable carrier.

(126.) A pharmaceutical composition comprising a combination of compounds of any one of the above (1.) to (124.) or pharmaceutically acceptable salts thereof and a pharmaceutically acceptable carrier.

(127.) The pharmaceutical composition of the above (125.) or (126.), further comprising a therapeutically effective amount of chemotherapeutic agent selected from the group consisting of a tubulin-forming inhibitor, a topoisomerase inhibitor, and a DNA binder.

(128.) A method for killing or inhibiting the proliferation of tumor cells or cancer cells comprising treating tumor cells or cancer cells with a compound of any of the above (1.) to (124.), or a pharmaceutical composition of any one of the above (125.) to (127.), in an amount effective to kill or inhibit the proliferation of the tumor cells or cancer cells.

(129.) A method for treating cancer in a patient in need thereof comprising administering to the patient a compound of any of the above (1.) to (124.), or a pharmaceutical composition of any one of the above (125.) to (127.), wherein the compound or pharmaceutical composition is administered in an amount effective to treat cancer.

(130.) The method of the above (129.), further comprising administering an effective amount of a second therapeutic agent.

(131.) A method of determining inhibition of cellular proliferation by a compound, comprising contacting cells in a cell culture medium with the compound of any of the above (1.) to (124.) and measuring the cytotoxic activity of the compound, whereby proliferation of the cells is inhibited.

(132.) A method of inhibiting the growth of tumor cells that overexpress a tumor-associated antigen comprising administering to a patient the compound of any of the above (1.) to (124.) conjugated to an antibody that is specific for said tumor-associated antigen, and optionally a second therapeutic agent wherein the compound and said second therapeutic agent are each administered in amounts effective to inhibit growth of tumor cells in the patient.

(133.) The method of the above (132.), wherein the compound sensitizes the tumor cells to said second therapeutic agent.

(134.) The method of the above (132.), wherein the compound induces cell death.

(135.) The method of the above (132.), wherein the compound induces apoptosis.

(136.) The method of the above (132.), wherein the cancer is selected from the group consisting of breast, ovarian, stomach, endometrial, salivary gland, lung, kidney, colon, colorectal, thyroid, pancreatic, prostate and bladder cancer.

(137.) A use of the compound of any of the above (1.) to (124.) in the manufacture of a medicament for treating cancer.

(138.) An article of manufacture comprising the compound of any of the above (1.) to (124.), a container, and a package insert or label indicating that the compound can be used to treat cancer characterized by the overexpression of at least one tumor-associated antigen.

(139.) An antibacterial or antifungal composition comprising a compound of any one of the above (1.) to (124.) or a pharmaceutically acceptable salt thereof in an amount effective to inhibit bacterial or fungal growth and a pharmaceutically acceptable carrier.

(140.) A method of inhibiting bacterial or fungal growth in a sample, comprising exposing the sample to a compound of any one of the above (1.) to (124.) or a pharmaceutically acceptable salt thereof, or a pharmaceutical composition of any one of the above (125.) to (127.).

(141.) A method for treating a bacterial or fungal infection in a patient in need thereof comprising administering to the patient a compound of any of the above (1.) to (124.), or a pharmaceutical composition of any one of the above (125.) to (127.), wherein the compound or pharmaceutical composition is administered in an amount effective to treat the infection.

(142.) The method of the above (141.), wherein the infection is caused by vancomycin-resistant *Enterococcus faecalis*, *Staphylococcus aureus*, methicillin-resistant *Staphylococcus aureus*, *Streptococcus pneumoniae*, penicillin-resistant *Streptococcus pneumoniae*, multi-drug-resistant *Streptococcus pneumoniae*, *Streptococcus pyogenes*, *Pseudomonas aeruginosa*, *Neisseria gonorrhoeae*, *Cryptococcus neoformans* or *Candida albicans*.

(143.) The method of the above (141.), wherein the infection is caused by *Streptococcus pneumoniae*, penicillin-resistant *Streptococcus pneumoniae*, multi-drug-resistant *Streptococcus pneumoniae*, or *Streptococcus pyogenes*.

(144.) A use of the compound of any of the above (1.) to (124.) in the manufacture of a medicament for treating a bacterial or fungal infection.

(145.) An article of manufacture comprising the compound of any of the above (1.) to (124.), a container, and a package insert or label indicating that the compound can be used to treat a bacterial or fungal infection.

Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The phrase "pharmaceutically acceptable salt," as used herein, refers to pharmaceutically acceptable organic or inorganic salts of a compound of the disclosure. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The term "pharmaceutically acceptable carrier" refers to a diluent, adjuvant or excipient, with which a compound of the disclosure may be administered. Pharmaceutically acceptable carriers include any and all solvents, diluents, or other liquid vehicles, dispersions or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the disclosure such as by producing any undesirable biological effect or otherwise interacting in a deleterious manner with any other component(s) of the pharmaceutically acceptable composition, its use is contemplated to be within the scope of this disclosure. Examples of pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols, such a propylene glycol or polyethylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "therapeutically effective amount" refers to an amount of a compound of the disclosure effective to treat a disease or disorder in a patient. In the case of cancer, the therapeutically effective amount of the compound may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the compound may inhibit the growth of and/or kill existing cancer cells, it may be cytostatic and/or cytotoxic. For cancer therapy, efficacy can, for example, be measured by assessing the time to disease progression (TTP) and/or determining the response rate (RR). In the case of bacterial or fungal infections, the therapeutically effect amount of the compound may reduce or inhibit the growth of bacteria or fungus.

The terms "treat" or "treatment" refer to therapeutic treatment and prophylactic measures to obtain a beneficial or desired result. For purposes of this disclosure, beneficial or desired results include, but are not limited to, alleviation of symptoms, diminishment of extent of disease, stabilized (i.e., not worsening) state of disease, delay or slowing of disease progression, amelioration or palliation of the disease state, remission (whether partial or total), whether detectable or undetectable and prevention of relapse. "Treatment" can also include prolonging survival as compared to expected survival if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of infections, the term "treating" includes inhibiting the growth of bacteria or fungus, preventing the growth of bacteria or fungus and ameliorating one or more symptoms associated with the infection.

The term "patient," as used herein, includes, but is not limited to, a human, rat, mouse, guinea pig, monkey, pig, goat, cow, horse, dog, cat, bird and fowl. In some embodiments, the patient is a human.

The terms "cancer" and "cancerous" refer to or describe the physiological condition or disorder in mammals that is typically characterized by unregulated cell growth. A "tumor" comprises one or more cancerous cells.

Exemplary cancers include, but not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, central nervous system cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute non-lymphocyctic leukemia, acute undifferentiated leukemia, chronic myelocytic leukemia (CML), chronic lymphocytic leukemia (CLL), hairy cell leukemia, multiple myeloma, Hodgkin's disease, non-Hodgkin's lymphoma, Waldenstrom's macroglobulinemia, heavy chain disease and polycythemia vera.

The term "cytotoxic activity" refers to a cell-killing, a cytostatic or an anti-proliferative effect of a compound of the disclosure. Methods for measuring cytotoxic activity are well-known in the art. Cytotoxic activity may be expressed as the $IC_{50}$ value, which is the concentration (molar or mass) per unit volume at which half the cells survive.

The term "$(C_1-C_6)$alkyl" refers to saturated linear and branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_6)$alkyl groups include methyl, ethyl, n-propyl, iso-propyl, n-butyl, tert-butyl, n-pentyl, n-hexyl, and the like.

The term "$(C_1-C_4)$alkyl" refers to saturated linear and branched hydrocarbon structures having 1, 2, 3 or 4 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_4)$alkyl groups include methyl, ethyl, n-propyl, iso-propyl, n-butyl, tert-butyl and the like.

The term "$(C_1-C_3)$alkyl" refers to saturated linear and branched hydrocarbon structures having 1, 2 or 3 carbon atoms. When an alkyl residue having a specific number of carbons is named, all geometric isomers having that number of carbons are intended to be encompassed; thus, for example, "propyl" includes n-propyl and iso-propyl. Examples of $(C_1-C_3)$alkyl groups include methyl, ethyl, n-propyl and iso-propyl.

The term "$(C_2-C_6)$alkenyl" refers to a straight-chain or branched unsaturated hydrocarbon radical having 2, 3, 4, 5 or 6 carbon atoms and a double bond in any position, e.g., ethenyl, 1 propenyl, 2 propenyl (allyl), 1-butenyl, 2-butenyl, 3-butenyl, 1-methylethenyl, 1-methyl-1 propenyl, 2-methyl-2-propenyl, 2-methyl-1-propenyl, 1-methyl-2-propenyl, 1-hexenyl, 2-hexenyl, 3-hexenyl, 2-methyl-2-pentenyl, 4-methyl-2-pentenyl, 4-methyl-1-pentenyl, 3-methyl-1-pentenyl, and the like.

The term "$(C_2-C_6)$alkynyl" refers to a straight chain or branched hydrocarbon having 2, 3, 4, 5 or 6 carbon atoms and including at least one carbon-carbon triple bond. Examples of $(C_2-C_6)$alkynyls include ethynyl, propynyl, 1-butynyl, 2-butynyl, 1-pentynyl, 2-pentynyl, 1-hexynyl, 2-hexynyl, 3-hexynyl, 4-methyl-2-pentynyl and the like.

The term "$(C_6-C_{14})$aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of $(C_6-C_{14})$aryl groups include without limitation phenyl, naphthyl, indanyl, indenyl, tetralinyl, anthryl and phenanthryl.

The term "(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. A (5- or 6-membered)heteroaryl group can be attached to the parent structure through a carbon or heteroatom. Examples of (5- or 6-membered)heteroaryls include pyridyl, pyrrolyl, pyrazolyl, furyl, imidazolyl, oxazolyl, imidazolyl, thiazolyl, isoxazolyl, 1,2,3 oxadiazolyl, 1,3,4-oxadiazolyl, 1,2,5 oxadiazolyl, 1,2,3-triazolyl, pyrazolyl, isothiazolyl, pyridazinyl, pyrimidyl, pyrazinyl, 1,2,3 thiadiazolyl, 1,3,4-thiadiazolyl, 1,2,5-thiadiazolyl, 1,3,5 triazinyl, and thiophenyl.

The term "(5-membered)heteroaryl" refers to a monocyclic aromatic heterocycle ring of 5 members, i.e., a monocyclic aromatic ring comprising at least one ring heteroatom, e.g., 1, 2, 3, or 4 ring heteroatoms, each independently selected from nitrogen, oxygen, and sulfur. A (5-membered) heteroaryl group can be attached to the parent structure through a carbon or heteroatom. Examples of (5-membered) heteroaryls include pyrrolyl, pyrazolyl, furyl, imidazolyl, oxazolyl, imidazolyl, thiazolyl, isoxazolyl, 1,2,3 oxadiazolyl, 1,3,4-oxadiazolyl, 1,2,5 oxadiazolyl, 1,2,3-triazolyl, pyrazolyl, isothiazolyl, 1,2,3 thiadiazolyl, 1,3,4-thiadiazolyl and 1,2,5-thiadiazolyl.

The term "(6-membered)heteroaryl" refers to a monocyclic aromatic heterocycle ring of 6 members, i.e., a monocyclic aromatic ring comprising at least one ring heteroatom, e.g., 1, 2, 3, or 4 ring heteroatoms, each independently selected from nitrogen, oxygen, and sulfur. A (6-membered) heteroaryl group can be attached to the parent structure through a carbon or heteroatom. Examples of (6-membered) heteroaryls include pyridyl, pyridazinyl, pyrimidyl, pyrazinyl, 1,3,5 triazinyl, and thiophenyl.

The term "9- or 10-membered bicyclic heteroaryl" refers to a bicyclic aromatic heterocycle ring of 9 or 10 members, i.e., a bicyclic aromatic ring comprising at least one ring heteroatom, e.g., 1, 2, 3, or 4 ring heteroatoms, each independently selected from nitrogen, oxygen, and sulfur. A (9- or 10-membered)heteroaryl group can be attached to the parent structure through a carbon or heteroatom. Examples of (9- or 10-membered)heteroaryl include benzofuran, benzothiophene, benzoxazole, benzothiazzole, indole, indazole, benzotriazole, benzoimidazole, quinolone, cinnoline, benzotriazine, quinazoline, quinoxaline and the like.

The term "$(C_3-C_7)$cycloalkyl" refers to a saturated cyclic hydrocarbon containing 3, 4, 5, 6 or 7 ring carbon atoms. Examples of $(C_3-C_7)$cycloalkyl groups include cyclopropyl, cyclobutyl, cyclopentyl, cyclohexyl, cycloheptyl and the like.

The term "(5- or 6-membered)heterocyclyl" refers to a 5- or 6-membered, saturated or partially unsaturated, monocyclic-heterocycle containing 1, 2, or 3 ring heteroatoms, each independently selected from nitrogen, oxygen, and sulfur, wherein said nitrogen and sulfur heteroatoms may optionally be oxidized and the nitrogen heteroatom may optionally be quaternized. Examples of "(5- or 6-membered)heterocyclyl groups include pyrrolidinyl, piperidinyl, piperazinyl, tetrahydro-oxazinyl, tetrahydrofuran, thiolane, dithiolane, pyrroline, pyrrolidine, pyrazoline, pyrazolidine, imidazoline, imidazolidine, tetrahydrofuranone, γ-butyrolactone, 2H-pyran, 4H-pyran, dioxolane, tetrahydropyran, dioxane, dihydrothiophene, piperazine, morpholine, thiomorpholine, oxazine, tetrahydro-oxazinyl, and the like.

The term "$(C_6)$heterocycloalkyl" refers to a 6-membered, saturated or partially unsaturated, bridged, mono- or bicyclic-heterocycle containing 1, 2, or 3 ring heteroatoms each independently selected from nitrogen, oxygen, and sulfur, wherein said nitrogen and sulfur heteroatoms may optionally be oxidized and the nitrogen heteroatom may optionally be quaternized. A heterocycloalkyl group can be attached to the parent structure through a carbon or heteroatom. Examples of (C6)heterocycloalkyl groups include piperidinyl, piperazinyl, tetrahydro-oxazinyl, tetrahydropyran, dioxane, morpholine, thiomorpholine, and the like.

The term "amino acid" refers to both natural and unnatural amino acids. Examples of amino acids include alanine, β-alanine, N-methyl alanine, N-ethyl alanine, N-methyl-β-alanine, N-ethyl-β-alanine, arginine, asparagine, aspartic acid, cysteine, homocysteine, cystine, glutamic acid, glutamine, glycine, N-ethyl glycine, N-propyl glycine, N-isopropyl glycine, phenylalanine, 4-aminophenylalanine, 3-aminophenylalanine, 2-aminophenylalanine, histidine, isoleucine, alloisoleucine, lysine, ornithine, citrulline, leucine, norleucine, t-leucine, methionine, proline, pipecolic acid, serine, homoserine, isoserine, threonine, allothreonine, valine, norvaline, isovaline, α-methylnorvaline, tryptophan, tyrosine, γ-aminobutyric acid, δ-aminolevulinic acid, 4-aminobenzoic acid, α-aminoisobuyric acid, dehydroalanine, cystathionine, lanthionine, djenkolic acid, diaminopimelic acid, α-amino-n-heptanoic acid, α,β-diaminopropionic acid, α,γ-diaminopropionic acid, β-amino-n-butyric acid, β-aminoisobutyric acid, sarcosine, α-hydroxy-γ-aminobutyric acid and the like.

The term "Protecting Group" refers to any group that is capable of reversibly protecting another functional group from undergoing an undesired reaction. Suitable protecting groups, as well as suitable conditions for protection and deprotection are well-known in the art and are described e.g., in T. W. Greene and P. G. M. Wuts, "Protective Groups in Organic Synthesis", Third edition, Wiley, New York 1999, and references cited therein.

The term "antibody" as used herein includes whole antibodies, monoclonal antibodies, polyclonal antibodies, monospecific antibodies, multispecific antibodies (e.g., bispecific antibodies), and antibody fragments that exhibit the desired biological activity. An antibody may be of any type or class (e.g., IgG, IgE, IgM, IgD, and IgA) or subclass (e.g., IgG1, IgG2, IgG3, IgG4, IgA1 and IgA2). The antibody may be derived from any suitable species. In some embodiments, the antibody is of human or murine origin. An antibody may be, for example, human, humanized or chimeric.

The term "monoclonal antibodies" as used herein refers to antibodies produced by a single clone of cells or cell line and comprising identical antibody molecules. The term "polyclonal antibodies" refers to antibodies produced by more than one type of cell or cell line and comprising different antibody molecules.

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

Compounds of Formula (I)

In one embodiment, the present disclosure provides a compound of formula (I),

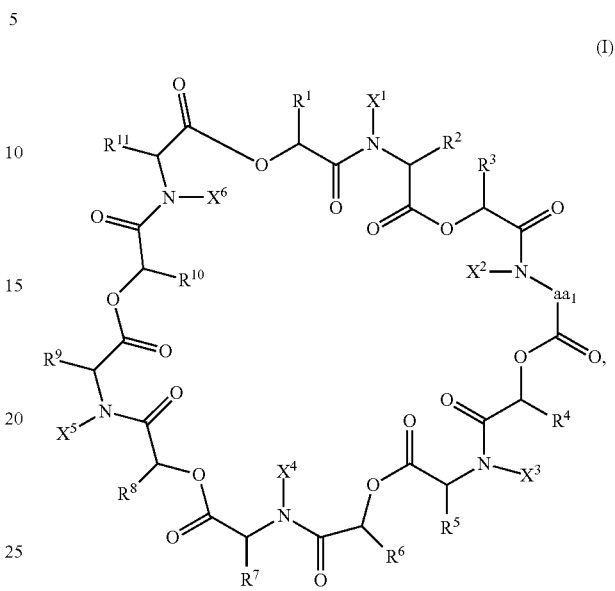

(I)

or a pharmaceutically acceptable salt thereof, wherein
$R^1$, $R^2$, $R^3$, $R^4$, $R^5$, $R^6$, $R^7$, $R^8$, $R^9$, $R^{10}$ and $R^{11}$ are independently selected from —($C_1$-$C_6$)alkyl, —($C_2$-$C_6$)alkenyl and —($C_2$-$C_6$)alkynyl,
wherein the alkyl, alkenyl or alkynyl are unsubstituted or substituted with a substituent selected from —OH, —$NH_2$, —NHR', —NHR'R", —SH, —SR', —C(O)OH, —C(O)$NH_2$, —C(O)NHR', —C(O)NR'R", —NHC(=NH)$NH_2$, —($C_6$-$C_{14}$)aryl, —($C_6$-$C_{14}$)aryl substituted with OH, -(5- or 6-membered monocyclic heteroaryl), -(9- or 10-membered bicyclic heteroaryl) and —($C_4$-$C_7$)cycloalkyl, wherein R' and R" are independently selected from —($C_1$-$C_6$)alkyl, —($C_2$-$C_6$)alkenyl and ($C_2$-$C_6$)alkynyl; or
wherein the alkyl, taken together with an adjacent N, forms a (5- or 6-membered)heterocyclyl;
$X^1$, $X^2$, $X^3$, $X^4$, $X^5$ and $X^6$ are independently selected from —H, ($C_1$-$C_6$)alkyl, —($C_2$-$C_6$)alkenyl and —($C_2$-$C_6$)alkynyl;
and
$aa_1$ is an amino acid, wherein the amino acid is unsubstituted or substituted with a protecting group or a Linking Unit.

In some embodiments, the compound of formula (I) is conjugated directly or indirectly to an antibody. In one embodiment, the compound of formula (I) is conjugated directly to an antibody. In another embodiment, the compound of formula (I) is conjugated to an antibody through a Linker Unit. The compound may be conjugated to an antibody through a Linker Unit at $aa_1$. The Linker Unit can operate to provide a suitable release of the compound of formula (I). The preparation of antibody drug conjugates is known to those of skill in the art.

In embodiments in which the compound of formula (I) is conjugated to an antibody through a Linker Unit, the Linker Unit may comprise a cleavable linker in one embodiment and a non-cleavable linker in another embodiment.

In embodiments in which the Linker Unit comprises a cleavable linker, the cleavable linker may be cleaved by methods known in the art. In one embodiment, the cleavable linker may be cleaved by a method selected from the group consisting of glycosidase-induced cleavage, acid-induced cleavage, light-induced cleavage, peptidase-induced cleavage, esterase-induced cleavage, and disulfide bond cleavage. In one embodiment, the cleavage method is selected from the group consisting of glycosidase-induced cleavage, acid-induced cleavage, peptidase-induced cleavage, esterase-induced cleavage, and disulfide bond cleavage. In another embodiment, the cleavage method is selected from the group consisting of glycosidase-induced cleavage, peptidase-induced cleavage, and esterase-induced cleavage. In another embodiment, the cleavage method is selected from glycosidase-induced cleavage or peptidase-induced cleavage. In another embodiment, the cleavage method is selected from glycosidase-induced cleavage or esterase-induced cleavage. In another embodiment, the cleavage method is selected from peptidase-induced cleavage or esterase-induced cleavage.

In embodiments in which the Linker Unit comprises a cleavable linker, the cleavable linker may comprise a glycosidic bond, a hydrazone, a cathepsin-B-cleavable peptide, a disulfide or an ester bond. In one embodiment, the cleavable linker comprises a glycosidic bond, a hydrazone, a cathepsin-B-cleavable peptide, or an ester bond. In one embodiment, the cleavable linker comprises a glycosidic bond, a hydrazone, or a cathepsin-B-cleavable peptide. In one embodiment, the cleavable linker comprises a glycosidic bond, a hydrazone, or an ester bond. In one embodiment, the cleavable linker comprises a glycosidic bond, a cathepsin-B-cleavable peptide, or an ester bond. In one embodiment, the cleavable linker comprises a hydrazone, a cathepsin-B-cleavable peptide, or an ester bond.

In one embodiment, the cleavable linker comprises a glycosidic bond. In one embodiment, the cleavable linker comprises glucuronide.

The compounds of formula (I) may be conjugated to any antibody, e.g., an antibody that binds to a tumor associated antigen. In one embodiment, the antibody used in the antibody drug conjugate of the disclosure is a monoclonal antibody. In another embodiment, the antibody used in the antibody drug conjugate of the disclosure binds at least one of CD19, CD20, CD30, CD33, CD70, BCMA, Glypican-3, Liv-1 and Lewis Y antigen.

When present, the Linker Unit is a bifunctional moiety that can be used to conjugate a compound of formula (I) to an antibody. Such bifunctional moieties are known in the art and include, but are not limited to, alkyldiyl, an aryldiyl, a heteroaryldiyl, moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide. See, e.g., U.S. Pat. Nos. 6,214,345 and 7,745,394, the contents of both of which are incorporated by reference in their entireties.

In some embodiments, the Linker Unit is as described in U.S. Pat. Nos. 6,214,345 and 7,745,394 and has formula:

wherein A is a Stretcher Unit,
a is 0 or 1,
each —W— is independently an Amino Acid Unit,
w is an integer ranging from 0 to 12,
Y is a Spacer Unit, and
y is 0, 1 or 2.

The Stretcher Unit (-A-), when present, is capable of linking an antibody to an Amino Acid Unit (—W—). The antibody has a functional group that can form a bond with a functional group of a Stretcher. Useful functional groups that can be present on an antibody, either naturally or via chemical manipulation include, but are not limited to, sulfhydryl, amino, hydroxyl, carboxy, the anomeric hydroxyl group of a carbohydrate, and carboxyl. In one aspect, the antibody functional groups are sulfhydryl and amino. Sulfhydryl groups can be generated by reduction of an intramolecular disulfide bond of an antibody. Alternatively, sulfhydryl groups can be generated by reaction of an amino group of a lysine moiety of an antibody using 2-iminothiolane (Traut's reagent) or another sulfhydryl generating reagent.

The Amino Acid Unit (—W—), when present, links the Stretcher Unit to the Spacer Unit if the Spacer Unit is present, links the Stretcher Unit to the compound of formula (I) if the Spacer Unit is absent, and links the antibody to the compound of formula (I) if the Stretcher Unit and Spacer Unit are absent.

$W_w$— is a dipeptide, tripeptide, tetrapeptide, pentapeptide, hexapeptide, heptapeptide, octapeptide, nonapeptide, decapeptide, undecapeptide or dodecapeptide unit. The Amino Acid may be any amino acid. In some embodiments, the Amino Acid Unit comprises natural amino acids. In other embodiments, the Amino Acid Unit comprises non-natural amino acids.

The Spacer Unit (—Y—), when present, links an Amino Acid Unit to the compound of formula (I) when an Amino Acid Unit is present. Alternately, the Spacer Unit links the Stretcher Unit to the compound of formula (I) when the Amino Acid Unit is absent. The Spacer Unit also links the compound of formula (I) to the antibody when both the Amino Acid Unit and Stretcher Unit are absent.

Suitable Spacer Units include, but are not limited to a glycine-glycine unit; a glycine unit; p-aminobenzyl alcohol (PAB) unit or aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals; spacers that undergo cyclization upon amide bond hydrolysis, such as substituted and unsubstituted 4-aminobutyric acid amides (Rodrigues et al., Chemistry Biology, 1995, 2, 223), appropriately substituted bicyclo[2.2.1] and bicyclo[2.2.2] ring systems (Storm, et al., J. Amer. Chem. Soc., 1972, 94, 5815) and 2-aminophenylpropionic acid amides (Amsberry, et al., J. Org. Chem., 1990, 55, 5867); and a branched bis(hydroxymethyl)styrene (BHMS) unit.

In some embodiments, at least one of $R_1$, $R_4$, and $R_8$ is $(C_1-C_6)$alkyl. In some embodiments, at least two of $R^1$, $R^4$, and $R^8$ are $(C_1-C_6)$alkyl. In some embodiments, each of $R^1$, $R^4$, and $R^8$ is $(C_1-C_6)$alkyl. In some embodiments, at least one of $R^1$, $R^4$, and $R^8$ is $(C_1-C_4)$alkyl. In some embodiments, at least two of $R^1$, $R^4$, and $R^8$ are $(C_1-C_4)$alkyl. In some embodiments, each of $R^1$, $R^4$, and $R^8$ is $(C_1-C_4)$alkyl. In some embodiments, at least one of $R^1$, $R^4$, and $R^8$ is $(C_4)$alkyl. In some embodiments, at least two of $R^1$, $R^4$, and $R^8$ are $(C_4)$alkyl. In some embodiments, each of $R^1$, $R^4$, and $R^8$ is $(C_4)$alkyl.

In some embodiments, at least one of $R^1$, $R^4$, and $R^8$ is $(C_1-C_6)$alkyl substituted with $(C_4-C_7)$cycloalkyl. In some embodiments, at least two of $R^1$, $R^4$, and $R^8$ are $(C_1-C_6)$alkyl substituted with $(C_4-C_7)$cycloalkyl. In some embodiments, each of $R^1$, $R^4$, and $R^8$ is $(C_1-C_6)$alkyl substituted with $(C_4-C_7)$cycloalkyl. In some embodiments, at least one of $R^1$, $R^4$, and $R^8$ is $(C_1-C_3)$alkyl substituted with $(C_4-C_7)$cycloalkyl. In some embodiments, at least two of $R^1$, $R^4$, and $R^8$ are $(C_1-C_3)$alkyl substituted with $(C_4-C_7)$cycloalkyl. In some embodiments, each of $R^1$, $R^4$, and $R^8$ is $(C_1-C_3)$alkyl substituted with $(C_4-C_7)$cycloalkyl. In some embodiments, at least one of $R^1$, $R^4$, and $R^8$ is $(C_1)$alkyl substituted with $(C_4\text{-}C_7)$cycloalkyl. In some embodiments, at least two of $R^1$, $R^4$, and $R^8$ are $(C_1)$alkyl substituted with $(C_4\text{-}C_7)$cycloalkyl. In some embodiments, each of $R^1$, $R^4$, and $R^8$ is $(C_1)$alkyl substituted with $(C_4\text{-}C_7)$cycloalkyl. In some embodiments, at least one of $R^1$, $R^4$, and $R^8$ is $(C_1\text{-}C_6)$alkyl substituted with $(C_6)$cycloalkyl. In some embodiments, at least two of $R^1$, $R^4$, and $R^8$ are $(C_1\text{-}C_6)$alkyl substituted with $(C_6)$cycloalkyl. In some embodiments, each of $R^1$, $R^4$, and $R^8$ is $(C_1\text{-}C_6)$alkyl substituted with $(C_6)$cycloalkyl. In some embodiments, at least one of $R^1$, $R^4$, and $R^8$ is $(C_1\text{-}C_3)$alkyl substituted with $(C_6)$cycloalkyl. In some embodiments, at least two of $R^1$, $R^4$, and $R^8$ are $(C_1\text{-}C_3)$alkyl substituted with $(C_6)$cycloalkyl. In some embodiments, each of $R^1$, $R^4$, and $R^8$ is $(C_1\text{-}C_3)$alkyl substituted with $(C_6)$cycloalkyl. In some embodiments, at least one of $R^1$, $R^4$, and $R^8$ is $(C_1)$alkyl substituted with $(C_6)$cycloalkyl. In some embodiments, at least two of $R^1$, $R^4$, and $R^8$ are $(C_1)$alkyl substituted with $(C_6)$cycloalkyl. In some embodiments, each of $R^1$, $R^4$, and $R^8$ is $(C_1)$alkyl substituted with $(C_6)$cycloalkyl.

In some embodiments, at least one of $R_1$, $R_4$, and $R_8$ is $(C_1\text{-}C_6)$alkyl or $(C_1\text{-}C_6)$alkyl substituted with $(C_4\text{-}C_7)$cycloalkyl. In another embodiment, one of $R^1$, $R^4$, and $R^8$ is $(C_1\text{-}C_4)$alkyl and the others are $(C_1\text{-}C_3)$alkyl substituted with $(C_4\text{-}C_7)$cycloalkyl. In another embodiment, two of $R^1$, $R^4$, and $R^8$ are $(C_1\text{-}C_4)$alkyl and the other is $(C_1\text{-}C_3)$alkyl substituted with $(C_4\text{-}C_7)$cycloalkyl. In another embodiment, each of $R^1$, $R^4$, and $R^8$ is $(C_1\text{-}C_4)$alkyl. In another embodiment, each of $R^1$, $R^4$, and $R^8$ is $(C_1\text{-}C_3)$alkyl substituted with $(C_4\text{-}C_7)$cycloalkyl.

In some embodiments, each of $R^2$, $R^3$, $R^5$, $R^6$, $R^7$, $R^9$, $R^{10}$ and $R^{11}$ is independently $(C_1\text{-}C_3)$alkyl. In some embodiments, each of $R^2$, $R^5$, $R^7$, $R^9$, and $R^{11}$ is $(C_3)$alkyl. In some embodiments, each of $R^3$, $R^6$, and $R^{10}$ is $(C_1)$alkyl.

In some embodiments, each of $X^1$, $X^2$, $X^3$, $X^4$, $X^5$ and $X^6$ is independently H or $(C_1\text{-}C_6)$alkyl. In some embodiments, each of $X^1$, $X^2$, $X^3$, $X^4$, $X^5$ and $X^6$ is H. In some embodiments, at least one of $X^1$, $X^2$, $X^3$, $X^4$, $X^5$ and $X^6$ is $(C_1\text{-}C_6)$alkyl and the other are H. In some embodiments, at least one of $X^1$, $X^2$, $X^3$, $X^4$, $X^5$ and $X^6$ is $(C_1\text{-}C_3)$alkyl and the other are H. In some embodiments, at least one of $X^1$, $X^2$, $X^3$, $X^4$, $X^5$ and $X^6$ is $(C_1)$alkyl and the other are H.

In some embodiments, $aa_1$ is a natural amino acid. In other embodiments, $aa_1$ is an unnatural amino acid. In some embodiments, $aa_1$ comprises a functional group selected from —$NH_2$, —SH, —OH or —COOH. In some embodiments, $aa_1$ comprises —$NH_2$. In some embodiments, $aa_1$ comprises —SH. In some embodiments, $aa_1$ comprises —OH. In some embodiments, $aa_1$ comprises —COOH. In some embodiments, $aa_1$ is valine. In other embodiments, $aa_1$ is threonine optionally substituted with a Protecting Group or a Linking Unit. In some embodiments, $aa_1$ is threonine. In other embodiments, $aa_1$ is threonine substituted with a Protecting Group. In other embodiments, $aa_1$ is threonine substituted with a Linking Unit. In other embodiments, $aa_1$ is tyrosine optionally substituted with a Protecting Group or a Linking Unit. In some embodiments, $aa_1$ is tyrosine. In other embodiments, $aa_1$ is tyrosine substituted with a Protecting Group. In other embodiments, $aa_1$ is tyrosine substituted with a Linking Unit. In some embodiments, $aa_1$ is 4-aminophenylalanine optionally substituted with a Protecting Group or a Linking Unit. In some embodiments, $aa_1$ is 4-aminophenylalanine. In other embodiments, $aa_1$ is 4-aminophenylalanine substituted with a Protecting Group. In other embodiments, $aa_1$ is 4-aminophenylalanine substituted with a Linking Unit. In some embodiments, $aa_1$ is 3-aminophenylalanine optionally substituted with a Protecting Group or a Linking Unit. In some embodiments, $aa_1$ is 3-aminophenylalanine. In other embodiments, $aa_1$ is 3-aminophenylalanine substituted with a Protecting Group. In other embodiments, $aa_1$ is 3-aminophenylalanine substituted with a Linking Unit. In some embodiments, $aa_1$ is 2-aminophenylalanine optionally substituted with a Protecting Group or a Linking Unit. In some embodiments, $aa_1$ is 2-aminophenylalanine. In other embodiments, $aa_1$ is 2-aminophenylalanine substituted with a Protecting Group. In other embodiments, $aa_1$ is 2-aminophenylalanine substituted with a Linking Unit.

In some embodiments, the Linking Unit comprises a cleavable linker. In some embodiments, the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage. In some embodiments, the cleavable linker comprises a glycosidic bond, a hydrazone, a cathepsin-B-cleavable peptide, a disulfide or an ester bond. In some embodiments, the cleavable linker comprises glucuronide.

In some embodiments, $A_a$ is maleimidocaproyl.

In some embodiments, $W_w$ is Valine-Citrulline.

In some embodiments, $Y_y$ is p-aminobenzyloxycarbonyl.

In some embodiments, $A_a$ is maleimidocaproyl, $W_w$ is Valine-Citrulline and $Y_y$ is p-aminobenzyloxycarbonyl.

In some embodiments, the Linking Unit comprises a monoclonal antibody.

In one embodiment, at least one of $R^1$, $R^4$, and $R^8$ is $(C_1\text{-}C_4)$alkyl and each of $R^2$, $R^3$, $R^5$, $R^6$, $R^7$, $R^9$, $R^{10}$ and $R^{11}$ is independently $(C_1\text{-}C_3)$alkyl. In one embodiment, at least two of $R^1$, $R^4$, and $R^8$ are $(C_1\text{-}C_4)$alkyl and each of $R_2$, $R^3$, $R^5$, $R^6$, $R^7$, $R^9$, $R^{10}$ and $R^{11}$ is independently $(C_1\text{-}C_3)$alkyl. In another embodiment, each of $R^1$, $R^4$, and $R^8$ is $(C_1\text{-}C_4)$alkyl and each of $R^2$, $R^3$, $R^5$, $R^6$, $R^7$, $R^9$, $R^{10}$ and $R^{11}$ is independently $(C_1\text{-}C_3)$alkyl. In another embodiment, at least one of $R^1$, $R^4$, and $R^8$ is $(C_4)$alkyl and each of $R^2$, $R^3$, $R^5$, $R^6$, $R^7$, $R^9$, $R^{10}$ and $R^{11}$ is independently $(C_1\text{-}C_3)$alkyl. In another embodiment, at least two of $R^1$, $R^4$, and $R^8$ are $(C_4)$alkyl and each of $R^2$, $R^3$, $R^5$, $R^6$, $R^7$, $R^9$, $R^{10}$ and $R^{11}$ is independently $(C_1\text{-}C_3)$alkyl. In another embodiment, each of $R^1$, $R^4$, and $R^8$ is $(C_4)$alkyl and each of $R^2$, $R^3$, $R^5$, $R^6$, $R^7$, $R^9$, $R^{10}$ and $R^{11}$ is independently $(C_1\text{-}C_3)$alkyl.

In one embodiment, at least one of $R^1$, $R^4$, and $R^8$ is $(C_1\text{-}C_4)$alkyl and each of $R^2$, $R^5$, $R^7$, $R^9$, and $R^{11}$ is $(C_3)$alkyl. In another embodiment, at least two of $R^1$, $R^4$, and $R^8$ are $(C_1\text{-}C_4)$alkyl and each of $R^2$, $R^5$, $R^7$, $R^9$, and $R^{11}$ is $(C_3)$alkyl. In another embodiment, each of $R^1$, $R^4$, and $R^8$ is $(C_1\text{-}C_4)$alkyl and each of $R^2$, $R^5$, $R^7$, $R^9$, and $R^{11}$ is $(C_3)$alkyl. In another embodiment, at least one of $R^1$, $R^4$, and $R^8$ is $(C_4)$alkyl and each of $R^2$, $R^5$, $R^7$, $R^9$, and $R^{11}$ is $(C_3)$alkyl. In another embodiment, at least two of $R^1$, $R^4$, and $R^8$ are $(C_4)$alkyl and each of $R^2$, $R^5$, $R^7$, $R^9$, and $R^{11}$ is $(C_3)$alkyl. In another embodiment, each of $R^1$, $R^4$, and $R^8$ is $(C_4)$alkyl and each of $R^2$, $R^5$, $R^7$, $R^9$, and $R^{11}$ is $(C_3)$alkyl.

In one embodiment, at least one of $R^1$, $R^4$, and $R^8$ is $(C_1\text{-}C_4)$alkyl and each of $R^3$, $R^6$, and $R^{10}$ is $(C_1)$alkyl. In another embodiment, at least two of $R^1$, $R^4$, and $R^8$ are $(C_1\text{-}C_4)$alkyl and each of $R^3$, $R^6$, and $R^{10}$ is $(C_1)$alkyl. In another embodiment, each of $R^1$, $R^4$, and $R^8$ is $(C_1\text{-}C_4)$alkyl and each of $R^3$, $R^6$, and $R^{10}$ is $(C_1)$alkyl. In another embodiment, at least one of $R^1$, $R^4$, and $R^8$ is $(C_4)$alkyl and each of $R^3$, $R^6$, and $R^{10}$ is $(C_1)$alkyl. In another embodiment, at least two of $R^1$, $R^4$, and $R^8$ are $(C_4)$alkyl and each of $R^3$, $R^6$, and $R^{10}$ is $(C_1)$alkyl. In another embodiment, each of $R^1$, $R^4$, and $R^8$ is $(C_4)$alkyl and each of $R^3$, $R^6$, and $R^{10}$ is $(C_1)$alkyl.

In one embodiment, at least one of $R^1$, $R^4$, and $R^8$ is $(C_1-C_3)$alkyl substituted with $(C_4-C_7)$cycloalkyl and each of $R^2$, $R^5$, $R^7$, $R^9$, and $R^{11}$ is $(C_3)$alkyl. In another embodiment, at least two of $R^1$, $R^4$, and $R^8$ are $(C_1-C_3)$alkyl substituted with $(C_4-C_7)$cycloalkyl and each of $R^2$, $R^5$, $R^7$, $R^9$, and $R^{11}$ is $(C_3)$alkyl. In another embodiment, each of $R^1$, $R^4$, and $R^8$ is $(C_1-C_3)$alkyl substituted with $(C_4-C_7)$cycloalkyl and each of $R^2$, $R^5$, $R^7$, $R^9$, and $R^{11}$ is $(C_3)$alkyl.

In one embodiment, at least one of $R^1$, $R^4$, and $R^8$ is $(C_1-C_3)$alkyl substituted with $(C_4-C_7)$cycloalkyl and each of $R^2$, $R^5$, $R^7$, $R^9$, and $R^{11}$ is $(C_3)$alkyl. In another embodiment, at least two of $R^1$, $R^4$, and $R^8$ are $(C_1-C_3)$alkyl substituted with $(C_4-C_7)$cycloalkyl and each of $R^2$, $R^5$, $R^7$, $R^9$, and $R^{11}$ is $(C_3)$alkyl. In another embodiment, each of $R^1$, $R^4$, and $R^8$ is $(C_1-C_3)$alkyl substituted with $(C_4-C_7)$cycloalkyl and each of $R^2$, $R^5$, $R^7$, $R^9$, and $R^{11}$ is $(C_3)$alkyl.

In one embodiment, at least one of $R^1$, $R^4$, and $R^8$ is $(C_1-C_3)$alkyl substituted with $(C_4-C_7)$cycloalkyl and each of $R^3$, $R^6$, and $R^{10}$ is $(C_1)$alkyl. In another embodiment, at least two of $R^1$, $R^4$, and $R^8$ are $(C_1-C_3)$alkyl substituted with $(C_4-C_7)$cycloalkyl and each of $R^3$, $R^6$, and $R^{10}$ is $(C_1)$alkyl. In another embodiment, each of $R^1$, $R^4$, and $R^8$ is $(C_1-C_3)$alkyl substituted with $(C_4-C_7)$cycloalkyl and each of $R^3$, $R^6$, and $R^{10}$ is $(C_1)$alkyl.

In one embodiment, at least one of $R^1$, $R^4$, and $R^8$ is $(C_1-C_4)$alkyl or $(C_1-C_3)$alkyl substituted with $(C_4-C_7)$cycloalkyl and each of $R^2$, $R^3$, $R^5$, $R^6$, $R^7$, $R^9$, $R^{10}$ and $R^{11}$ is independently $(C_1-C_3)$alkyl. In another embodiment, one of $R^1$, $R^4$, and $R^8$ is $(C_1-C_4)$alkyl and the other two are $(C_1-C_3)$alkyl substituted with $(C_4-C_7)$cycloalkyl and each of $R^2$, $R^3$, $R^5$, $R^6$, $R^7$, $R^9$, $R^{10}$ and $R^{11}$ is independently $(C_1-C_3)$alkyl. In another embodiment, two of $R^1$, $R^4$, and $R^8$ are $(C_1-C_4)$alkyl and the other is $(C_1-C_3)$alkyl substituted with $(C_4-C_7)$cycloalkyl and each of $R^2$, $R^3$, $R^5$, $R^6$, $R^7$, $R^9$, $R^{10}$ and $R^{11}$ is independently $(C_1-C_3)$alkyl. In another embodiment, each of $R^1$, $R^4$, and $R^8$ is $(C_1-C_4)$alkyl and each of $R^2$, $R^3$, $R^5$, $R^6$, $R^7$, $R^9$, $R^{10}$ and $R^{11}$ is independently $(C_1-C_3)$alkyl. In another embodiment, each of $R^1$, $R^4$, and $R^8$ is $(C_1-C_3)$alkyl substituted with $(C_4-C_7)$cycloalkyl and each of $R^2$, $R^3$, $R^5$, $R^6$, $R^7$, $R^9$, $R^{10}$ and $R^{11}$ is independently $(C_1-C_3)$alkyl.

In one embodiment, at least one of $R^1$, $R^4$, and $R^8$ is $(C_1-C_4)$alkyl or $(C_1-C_3)$alkyl substituted with $(C_4-C_7)$cycloalkyl and each of $R^2$, $R^5$, $R^7$, $R^9$, and $R^{11}$ is $(C_3)$alkyl. In another embodiment, one of $R^1$, $R^4$, and $R^8$ is $(C_1-C_4)$alkyl and the other two are $(C_1-C_3)$alkyl substituted with $(C_4-C_7)$cycloalkyl and each of $R^2$, $R^5$, $R^7$, $R^9$, and $R^{11}$ is $(C_3)$alkyl. In another embodiment, two of $R^1$, $R^4$, and $R^8$ are $(C_1-C_4)$alkyl and the other is $(C_1-C_3)$alkyl substituted with $(C_4-C_7)$cycloalkyl and each of $R^2$, $R^5$, $R^7$, $R^9$, and $R^{11}$ is $(C_3)$alkyl. In another embodiment, each of $R^1$, $R^4$, and $R^8$ is $(C_1-C_4)$alkyl and each of $R^2$, $R^5$, $R^7$, $R^9$, and $R^{11}$ is $(C_3)$alkyl. In another embodiment, each of $R^1$, $R^4$, and $R^8$ is $(C_1-C_3)$alkyl substituted with $(C_4-C_7)$cycloalkyl and each of $R^2$, $R^5$, $R^7$, $R^9$, and $R^{11}$ is $(C_3)$alkyl.

In one embodiment, at least one of $R^1$, $R^4$, and $R^8$ is $(C_1-C_4)$alkyl or $(C_1-C_3)$alkyl substituted with $(C_4-C_7)$cycloalkyl and each of $R^3$, $R^6$, and $R^{10}$ is $(C_1)$alkyl. In another embodiment, one of $R^1$, $R^4$, and $R^8$ is $(C_1-C_4)$alkyl and the other two are $(C_1-C_3)$alkyl substituted with $(C_4-C_7)$cycloalkyl and each of $R^3$, $R^6$, and $R^{10}$ is $(C_1)$alkyl. In another embodiment, two of $R^1$, $R^4$, and $R^8$ are $(C_1-C_4)$alkyl and the other is $(C_1-C_3)$alkyl substituted with $(C_4-C_7)$cycloalkyl and each of $R^3$, $R^6$, and $R_{10}$ is $(C_1)$alkyl. In another embodiment, each of $R^1$, $R^4$, and $R^8$ is $(C_1-C_4)$alkyl and each of $R^3$, $R^6$, and $R^{10}$ is $(C_1)$alkyl. In another embodiment, each of $R^1$, $R^4$, and $R^8$ is $(C_1-C_3)$alkyl substituted with $(C_4-C_7)$cycloalkyl and each of $R^3$, $R^6$, and $R^{10}$ is $(C_1)$alkyl.

In one embodiment, at least two of $R^1$, $R^4$, and $R^8$ are $(C_1-C_4)$alkyl and each of $X^1$, $X^2$, $X^3$, $X^4$, $X^5$ and $X^6$ is independently H or $(C_1-C_6)$alkyl. In another embodiment, each of $R^1$, $R^4$, and $R^8$ is $(C_1-C_4)$alkyl and each of $X^1$, $X^2$, $X^3$, $X^4$, $X^5$ and $X^6$ is independently H or $(C_1-C_6)$alkyl. In another embodiment, at least one of $R^1$, $R^4$, and $R^8$ is $(C_4)$alkyl and each of $X^1$, $X^2$, $X^3$, $X^4$, $X^5$ and $X^6$ is independently H or $(C_1-C_6)$alkyl. In another embodiment, at least two of $R^1$, $R^4$, and $R^8$ are $(C_4)$alkyl and each of $X^1$, $X^2$, $X^3$, $X^4$, $X^5$ and $X^6$ is independently H or $(C_1-C_6)$alkyl. In another embodiment, each of $R^1$, $R^4$, and $R^8$ is $(C_4)$alkyl and each of $X^1$, $X^2$, $X^3$, $X^4$, $X^5$ and $X^6$ is independently H or $(C_1-C_6)$alkyl.

In one embodiment, at least two of $R^1$, $R^4$, and $R^8$ are $(C_1-C_4)$alkyl and each of $X^1$, $X^2$, $X^3$, $X^4$, $X^5$ and $X^6$ is H. In another embodiment, each of $R^1$, $R^4$, and $R^8$ is $(C_1-C_4)$alkyl and each of $X^1$, $X^2$, $X^3$, $X^4$, $X^5$ and $X^6$ is H. In another embodiment, at least one of $R^1$, $R^4$, and $R^8$ is $(C_4)$alkyl and each of $X^1$, $X^2$, $X^3$, $X^4$, $X^5$ and $X^6$ is H. In another embodiment, at least two of $R^1$, $R^4$, and $R^8$ are $(C_4)$alkyl and each of $X^1$, $X^2$, $X^3$, $X^4$, $X^5$ and $X^6$ is H. In another embodiment, each of $R^1$, $R^4$, and $R^8$ is $(C_4)$alkyl and each of $X^1$, $X^2$, $X^3$, $X^4$, $X^5$ and $X^6$ is H.

In one embodiment, at least two of $R^1$, $R^4$, and $R^8$ are $(C_1-C_4)$alkyl and at least one of $X^1$, $X^2$, $X^3$, $X^4$, $X^5$ and $X^6$ is $(C_1)$alkyl and the other are H. In another embodiment, each of $R^1$, $R^4$, and $R^8$ is $(C_1-C_4)$alkyl and at least one of $X^1$, $X^2$, $X^3$, $X^4$, $X^5$ and $X^6$ is $(C_1)$alkyl and the other are H. In another embodiment, at least one of $R^1$, $R^4$, and $R^8$ is $(C_4)$alkyl and at least one of $X^1$, $X^2$, $X^3$, $X^4$, $X^5$ and $X^6$ is $(C_1)$alkyl and the other are H. In another embodiment, at least two of $R^1$, $R^4$, and $R^8$ are $(C_4)$alkyl and at least one of $X^1$, $X^2$, $X^3$, $X^4$, $X^5$ and $X^6$ is $(C_1)$alkyl and the other are H. In another embodiment, each of $R^1$, $R^4$, and $R^8$ is $(C_4)$alkyl and at least one of $X^1$, $X^2$, $X^3$, $X^4$, $X^5$ and $X^6$ is $(C_1)$alkyl and the other are H.

In one embodiment, at least one of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl. In another embodiment, at least two of $R^1$, $R^4$, and $R^8$ are $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl. In another embodiment, each of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl.

In one embodiment, at least one of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is H. In another embodiment, at least two of $R^1$, $R^4$, and $R^8$ are $(C_1-C_3)$alkyl substituted with $(C_4-C_7)$cycloalkyl and each of $X^1$, $X^2$, $X^3$, $X^4$, $X^5$ and $X^6$ is H. In another embodiment, each of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is H.

In one embodiment, at least one of $R^1$, $R^4$, and $R^8$ is $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H. In another embodiment, at least two of $R^1$, $R^4$, and $R^8$ are $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H. In another embodiment, each of $R^1$, $R^4$, and $R^8$ is $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H.

In one embodiment, at least one of $R^1$, $R^4$, and $R^8$ is $(C_1-C_4)$alkyl or $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl. In another embodiment, one of $R^1$, $R^4$, and $R^8$ is $(C_1-C_4)$alkyl and the other two are $(C_1-C_3)$ alkyl substituted with $(C_4-C_7)$cycloalkyl and each of $X^1$, $X^2$, $X^3$, $X^4$, $X^5$ and $X^6$ is independently H or $(C_1-C_6)$alkyl. In another embodiment, two of $R^1$, $R^4$, and $R^8$ are $(C_1-C_4)$alkyl and the other is $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl. In another embodiment, each of $R^1$, $R^4$, and $R^8$ is $(C_1-C_4)$alkyl and each of $X^1$, $X^2$, $X^3$, $X^4$, $X^5$ and $X^6$ is independently H or $(C_1-C_6)$alkyl. In another embodiment, each of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl.

In one embodiment, at least one of $R^1$, $R^4$, and $R^8$ is $(C_1-C_4)$alkyl or $(C_1-C_3)$alkyl substituted with $(C_4-C_7)$cycloalkyl 1 and each of $X^1$, $X^2$, $X^3$, $X^4$, $X^5$ and $X^6$ is H. In another embodiment, one of $R^1$, $R^4$, and $R^8$ is $(C_1-C_4)$alkyl and the other two are $(C_1-C_3)$alkyl substituted with $(C_4-C_7)$ cycloalkyl and each of $X^1$, $X^2$, $X^3$, $X^4$, $X^5$ and $X^6$ is H. In another embodiment, two of $R^1$, $R^4$, and $R^8$ are $(C_1-C_4)$alkyl and the other is $(C_1-C_3)$alkyl substituted with $(C_4-C_7)$cycloalkyl and each of $X^1$, $X^2$, $X^3$, $X^4$, $X^5$ and $X^6$ is H. In another embodiment, each of $R^1$, $R^4$, and $R^8$ is $(C_1-C_4)$alkyl and each of $X^1$, $X^2$, $X^3$, $X^4$, $X^5$ and $X^6$ is H. In another embodiment, each of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is H.

In one embodiment, at least one of $R^1$, $R^4$, and $R^8$ is $(C_1-C_4)$alkyl or $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H. In another embodiment, one of $R^1$, $R^4$, and $R^8$ is $(C_1-C_4)$alkyl and the other two are $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H. In another embodiment, two of $R^1$, $R^4$, and $R^8$ are $(C_1-C_4)$alkyl and the other is $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H. In another embodiment, each of $R^1$, $R^4$, and $R^8$ is $(C_1-C_4)$alkyl and at least one of $X^1$, $X^2$, $X^3$, $X^4$, $X^5$ and $X^6$ is $(C_1)$alkyl and the other are H. In another embodiment, each of $R^1$, $R^4$, and $R^8$ is $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H.

In one embodiment, each of $R^2$, $R^3$, $R^5$, $R^6$, $R^7$, $R^9$, $R^{10}$ and $R^{11}$ is independently $(C_1-C_3)$alkyl and each of $X^1$, $X^2$, $X^3$, $X^4$, $X^5$ and $X^6$ is independently H or $(C_1-C_6)$alkyl. In another embodiment, each of $R^2$, $R^5$, $R^7$, $R^9$, and $R^{11}$ is $(C_3)$alkyl and each of $X^1$, $X^2$, $X^3$, $X^4$, $X^5$ and $X^6$ is independently H or $(C_1-C_6)$alkyl. In another embodiment, each of $R^3$, $R^6$, and $R^{10}$ is $(C_1)$alkyl and each of $X^1$, $X^2$, $X^3$, $X^4$, $X^5$ and $X^6$ is independently H or $(C_1-C_6)$alkyl.

In one embodiment, each of $R^2$, $R^3$, $R^5$, $R^6$, $R^7$, $R^9$, $R^{10}$ and $R^{11}$ is independently $(C_1-C_3)$alkyl and each of $X^1$, $X^2$, $X^3$, $X^4$, $X^5$ and $X^6$ is H. In another embodiment, each of $R^2$, $R^5$, $R^7$, $R^9$, and $R^{11}$ is $(C_3)$alkyl and each of $X^1$, $X^2$, $X^3$, $X^4$, $X^5$ and $X^6$ is H. In another embodiment, each of $R^3$, $R^6$, and $R^{10}$ is $(C_1)$alkyl and each of $X^1$, $X^2$, $X^3$, $X^4$, $X^5$ and $X^6$ is H.

In one embodiment, each of $R^2$, $R^3$, $R^5$, $R^6$, $R^7$, $R^9$, $R^{10}$ and $R^{11}$ is independently $(C_1-C_3)$alkyl and at least one of $X^1$, $X^2$, $X^3$, $X^4$, $X^5$ and $X^6$ is $(C_1)$alkyl and the other are H. In another embodiment, each of $R^2$, $R^5$, $R^7$, $R^9$, and $R^{11}$ is $(C_3)$alkyl and at least one of $X^1$, $X^2$, $X^3$, $X^4$, $X^5$ and $X^6$ is $(C_1)$alkyl and the other are H. In another embodiment, each of $R^3$, $R^6$, and $R^{10}$ is $(C_1)$alkyl and at least one of $X^1$, $X^2$, $X^3$, $X^4$, $X^5$ and $X^6$ is $(C_1)$alkyl and the other are H.

In one embodiment, at least two of $R^1$, $R^4$, and $R^8$ are $(C_1-C_4)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^1$, $R^4$, and $R^8$ is $(C_1-C_4)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, at least one of $R^1$, $R^4$, and $R^8$ is $(C_4)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, at least two of $R^1$, $R^4$, and $R^8$ are $(C_4)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^1$, $R^4$, and $R^8$ is $(C_4)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit.

In one embodiment, at least one of $R^1$, $R^4$, and $R^8$ is $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, at least two of $R^1$, $R^4$, and $R^8$ are $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^1$, $R^4$, and $R^8$ is $(C_1-C_3)$alkyl substituted with $(C_4-C_7)$ cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit.

In one embodiment, at least one of $R^1$, $R^4$, and $R^8$ is $(C_1-C_4)$alkyl or $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, one of $R^1$, $R^4$, and $R^8$ is $(C_1-C_4)$alkyl and the other two are $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, two of $R^1$, $R^4$, and $R^8$ are $(C_1-C_4)$alkyl and the other is $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^1$, $R^4$, and $R^8$ is $(C_1-C_4)$alkyl $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^1$, $R^4$, and $R^8$ is $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit.

In one embodiment, each of $R^2$, $R^3$, $R^5$, $R^6$, $R^7$, $R^9$, $R^{10}$ and $R^{11}$ is independently $(C_1-C_3)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^2$, $R^5$, $R^7$, $R^9$, and $R^{11}$ is $(C_3)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^3$, $R^6$, and $R^{10}$ is $(C_1)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit.

In one embodiment, each of $X^1$, $X^2$, $X^3$, $X^4$, $X^5$ and $X^6$ is independently H or $(C_1-C_6)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $X^1$, $X^2$, $X^3$, $X^4$, $X^5$ and $X^6$ is H and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, at least one of $X^1$, $X^2$, $X^3$, $X^4$, $X^5$ and $X^6$ is $(C_1)$alkyl and the other are H and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit.

In some embodiments, the present disclosure provides a compound has formula (Ia):

(Ia)

or a pharmaceutically acceptable salt thereof, wherein
aa$_1$ is valine, threonine optionally substituted with a protecting group or a Linking Unit, and tyrosine optionally substituted with a protecting group or a Linking Unit.

In some embodiments, aa$_1$ is valine. In other embodiments, aa$_1$ is threonine optionally substituted with a Protecting Group or a Linking Unit. In some embodiments, aa$_1$ is threonine. In other embodiments, aa$_1$ is threonine substituted with a Protecting Group. In other embodiments, aa$_1$ is threonine substituted with a Linking Unit. In other embodiments, aa$_1$ is tyrosine optionally substituted with a Protecting Group or a Linking Unit. In some embodiments, aa$_1$ is tyrosine. In other embodiments, aa$_1$ is tyrosine substituted with a Protecting Group. In other embodiments, aa$_1$ is tyrosine substituted with a Linking Unit.

In some embodiments, the Linking Unit comprises a cleavable linker. In some embodiments, the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage. In some embodiments, the cleavable linker comprises a glycosidic bond, a hydrazone, a cathepsin-B-cleavable peptide, a disulfide or an ester bond. In some embodiments, the cleavable linker comprises glucuronide.

In some embodiments, A$_a$ is maleimidocaproyl.
In some embodiments, W$_w$ is Valine-Citrulline.
In some embodiments, Y$_y$ is p-aminobenzyloxycarbonyl.
In some embodiments, A$_a$ is maleimidocaproyl, W$_w$ is Valine-Citrulline and Y$_y$ is p-aminobenzyloxycarbonyl.

In some embodiments, the Linking Unit comprises a monoclonal antibody.

In some embodiments, the present disclosure provides a compound has formula (Ib):

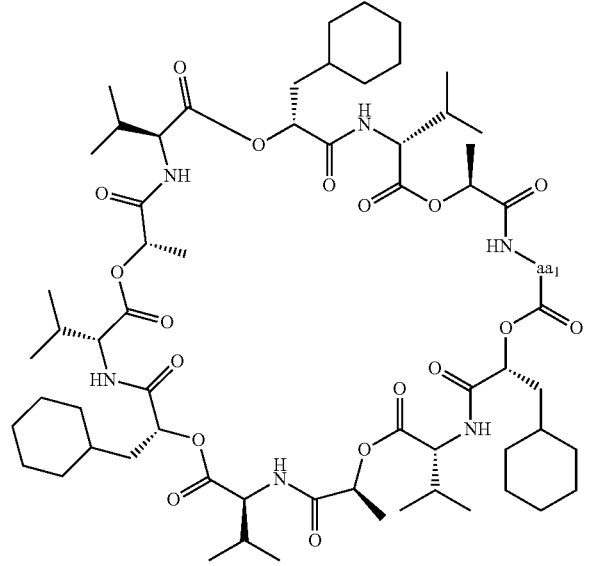

(Ib)

or a pharmaceutically acceptable salt thereof, wherein
aa$_1$ is valine, threonine optionally substituted with a protecting group or a Linking Unit, and tyrosine optionally substituted with a protecting group or a Linking Unit.

In some embodiments, aa$_1$ is valine. In other embodiments, aa$_1$ is threonine optionally substituted with a Protecting Group or a Linking Unit. In some embodiments, aa$_1$ is threonine. In other embodiments, aa$_1$ is threonine substituted with a Protecting Group. In other embodiments, aa$_1$ is threonine substituted with a Linking Unit. In other embodiments, aa$_1$ is tyrosine optionally substituted with a Protecting Group or a Linking Unit. In some embodiments, aa$_1$ is tyrosine. In other embodiments, aa$_1$ is tyrosine substituted with a Protecting Group. In other embodiments, aa$_1$ is tyrosine substituted with a Linking Unit.

In some embodiments, the Linking Unit comprises a cleavable linker. In some embodiments, the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage. In some embodiments, the cleavable linker comprises a glycosidic bond, a hydrazone, a cathepsin-B-cleavable peptide, a disulfide or an ester bond. In some embodiments, the cleavable linker comprises glucuronide.

In some embodiments, A$_a$ is maleimidocaproyl.
In some embodiments, W$_w$ is Valine-Citrulline.
In some embodiments, Y$_y$ is p-aminobenzyloxycarbonyl.
In some embodiments, A$_a$ is maleimidocaproyl, W$_w$ is Valine-Citrulline and Y$_y$ is p-aminobenzyloxycarbonyl.

In some embodiments, the Linking Unit comprises a monoclonal antibody.

In some embodiments, the present disclosure provides a compound has formula (Ic):

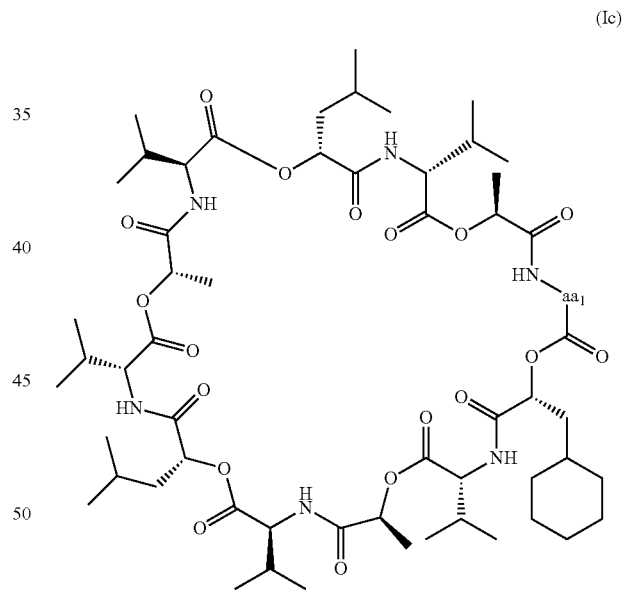

(Ic)

or a pharmaceutically acceptable salt thereof, wherein
aa$_1$ is valine, threonine optionally substituted with a protecting group or a Linking Unit, and tyrosine optionally substituted with a protecting group or a Linking Unit.

In some embodiments, aa$_1$ is valine. In other embodiments, aa$_1$ is threonine optionally substituted with a Protecting Group or a Linking Unit. In some embodiments, aa$_1$ is threonine. In other embodiments, aa$_1$ is threonine substituted with a Protecting Group. In other embodiments, aa$_1$ is threonine substituted with a Linking Unit. In other embodiments, aa$_1$ is tyrosine optionally substituted with a Protecting Group or a Linking Unit. In some embodiments, aa$_1$ is tyrosine. In other embodiments, aa$_1$ is tyrosine substituted with a Protecting Group. In other embodiments, $aa_1$ is tyrosine substituted with a Linking Unit.

In some embodiments, the Linking Unit comprises a cleavable linker. In some embodiments, the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage. In some embodiments, the cleavable linker comprises a glycosidic bond, a hydrazone, a cathepsin-B-cleavable peptide, a disulfide or an ester bond. In some embodiments, the cleavable linker comprises glucuronide.

In some embodiments, $A_a$ is maleimidocaproyl.
In some embodiments, $W_w$ is Valine-Citrulline.
In some embodiments, $Y_y$ is p-aminobenzyloxycarbonyl.
In some embodiments, $A_a$ is maleimidocaproyl, $W_w$ is Valine-Citrulline and $Y_y$ is p-aminobenzyloxycarbonyl.

In some embodiments, the Linking Unit comprises a monoclonal antibody.

Compounds of Formula (II)

In another embodiment, the present disclosure provides a compound of formula (II),

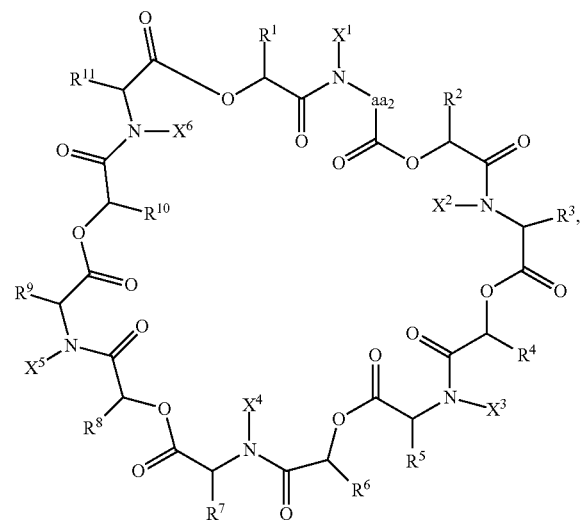

(II)

or a pharmaceutically acceptable salt thereof, wherein
$R^1$, $R^2$, $R^3$, $R^4$, $R^5$, $R^6$, $R^7$, $R^8$, $R^9$, $R^{10}$ and $R^{11}$ are independently selected from —$(C_1$-$C_6)$alkyl, —$(C_2$-$C_6)$ alkenyl and —$(C_2$-$C_6)$alkynyl,
  wherein the alkyl, alkenyl or alkynyl are unsubstituted or substituted with a substituent selected from —OH, —$NH_2$, —NHR', —NHR'R", —SH, —SR', —C(O) OH, —C(O)$NH_2$, —C(O)NHR', —C(O)NR'R", —NHC(=NH)$NH_2$, —$(C_6$-$C_{14})$aryl, —$(C_6$-$C_{14})$aryl substituted with OH, -(5- or 6-membered monocyclic heteroaryl), -(9- or 10-membered bicyclic heteroaryl) and —$(C_4$-$C_7)$cycloalkyl, wherein R' and R" are independently selected from —$(C_1$-$C_6)$alkyl, —$(C_2$-$C_6)$alkenyl and $(C_2$-$C_6)$alkynyl; or
  wherein the alkyl, taken together with an adjacent N, forms a (5- or 6-membered)heterocyclyl;
$X^1$, $X^2$, $X^3$, $X^4$, $X^5$ and $X^6$ are independently selected from —H, $(C_1$-$C_6)$alkyl, —$(C_2$-$C_6)$alkenyl and —$(C_2$-$C_6)$alkynyl;

$aa_2$ is an amino acid, wherein the amino acid is unsubstituted or substituted with a protecting group or a Linking Unit.

The Linker Unit is as defined for Compound of Formula (I).

In some embodiments, the compound of formula (II) is conjugated directly or indirectly to an antibody. In one embodiment, the compound of formula (II) is conjugated directly to an antibody. In another embodiment, the compound of formula (II) is conjugated to an antibody through a Linker Unit. The compound may be conjugated to an antibody through a Linker Unit at $aa_1$. The Linker Unit can operate to provide a suitable release of the compound of formula (II). The preparation of antibody drug conjugates is known to those of skill in the art.

The compounds of formula (II) may be conjugated to any antibody, e.g., an antibody that binds to a tumor associated antigen. In one embodiment, the antibody used in the antibody drug conjugate of the disclosure is a monoclonal antibody. In another embodiment, the antibody used in the antibody drug conjugate of the disclosure binds at least one of CD19, CD20, CD30, CD33, CD70, BCMA, Glypican-3, Liv-1 and Lewis Y antigen.

In some embodiments, at least one of $R_1$, $R_4$, and $R_8$ is $(C_1$-$C_6)$alkyl. In some embodiments, at least two of $R^1$, $R^4$, and $R^8$ are $(C_1$-$C_6)$alkyl. In some embodiments, each of $R^1$, $R^4$, and $R^8$ is $(C_1$-$C_6)$alkyl. In some embodiments, at least one of $R^1$, $R^4$, and $R^8$ is $(C_1$-$C_4)$alkyl. In some embodiments, at least two of $R^1$, $R^4$, and $R^8$ are $(C_1$-$C_4)$alkyl. In some embodiments, each of $R^1$, $R^4$, and $R^8$ is $(C_1$-$C_4)$alkyl. In some embodiments, at least one of $R^1$, $R^4$, and $R^8$ is $(C_4)$alkyl. In some embodiments, at least two of $R^1$, $R^4$, and $R^8$ are $(C_4)$alkyl. In some embodiments, each of $R^1$, $R^4$, and $R^8$ is $(C_4)$alkyl.

In some embodiments, at least one of $R^1$, $R^4$, and $R^8$ is $(C_1$-$C_6)$alkyl substituted with $(C_4$-$C_7)$cycloalkyl. In some embodiments, at least two of $R^1$, $R^4$, and $R^8$ are $(C_1$-$C_6)$alkyl substituted with $(C_4$-$C_7)$cycloalkyl. In some embodiments, each of $R^1$, $R^4$, and $R^8$ is $(C_1$-$C_6)$alkyl substituted with $(C_4$-$C_7)$cycloalkyl. In some embodiments, at least one of $R^1$, $R^4$, and $R^8$ is $(C_1$-$C_3)$alkyl substituted with $(C_4$-$C_7)$cycloalkyl. In some embodiments, at least two of $R^1$, $R^4$, and $R^8$ are $(C_1$-$C_3)$alkyl substituted with $(C_4$-$C_7)$cycloalkyl. In some embodiments, each of $R^1$, $R^4$, and $R^8$ is $(C_1$-$C_3)$alkyl substituted with $(C_4$-$C_7)$cycloalkyl. In some embodiments, at least one of $R^1$, $R^4$, and $R^8$ is $(C_1)$alkyl substituted with $(C_4$-$C_7)$cycloalkyl. In some embodiments, at least two of $R^1$, $R^4$, and $R^8$ are $(C_1)$alkyl substituted with $(C_4$-$C_7)$cycloalkyl. In some embodiments, each of $R^1$, $R^4$, and $R^8$ is $(C_1)$alkyl substituted with $(C_4$-$C_7)$cycloalkyl. In some embodiments, at least one of $R^1$, $R^4$, and $R^8$ is $(C_1$-$C_6)$alkyl substituted with $(C_6)$cycloalkyl. In some embodiments, at least two of $R^1$, $R^4$, and $R^8$ are $(C_1$-$C_6)$alkyl substituted with $(C_6)$cycloalkyl. In some embodiments, each of $R^1$, $R^4$, and $R^8$ is $(C_1$-$C_6)$alkyl substituted with $(C_6)$cycloalkyl. In some embodiments, at least one of $R^1$, $R^4$, and $R^8$ is $(C_1$-$C_3)$alkyl substituted with $(C_6)$cycloalkyl. In some embodiments, at least two of $R^1$, $R^4$, and $R^8$ are $(C_1$-$C_3)$alkyl substituted with $(C_6)$cycloalkyl. In some embodiments, each of $R^1$, $R^4$, and $R^8$ is $(C_1$-$C_3)$alkyl substituted with $(C_6)$cycloalkyl. In some embodiments, at least one of $R^1$, $R^4$, and $R^8$ is $(C_1)$alkyl substituted with $(C_6)$cycloalkyl. In some embodiments, at least two of $R^1$, $R^4$, and $R^8$ are $(C_1)$alkyl substituted with $(C_6)$cycloalkyl. In some embodiments, each of $R^1$, $R^4$, and $R^8$ is $(C_1)$alkyl substituted with $(C_6)$cycloalkyl.

In some embodiments, at least one of $R_1$, $R_4$, and $R_8$ is $(C_1$-$C_6)$alkyl or $(C_1$-$C_6)$alkyl substituted with $(C_4$-$C_7)$cycloalkyl. In another embodiment, one of $R^1$, $R^4$, and $R^8$ is ($C_1$-$C_4$)alkyl and the other two are ($C_1$-$C_3$)alkyl substituted with ($C_4$-$C_7$)cycloalkyl. In another embodiment, two of $R^1$, $R^4$, and $R^8$ are ($C_1$-$C_4$)alkyl and the other is ($C_1$-$C_3$)alkyl substituted with ($C_4$-$C_7$)cycloalkyl. In another embodiment, each of $R^1$, $R^4$, and $R^8$ is ($C_1$-$C_4$)alkyl. In another embodiment, each of $R^1$, $R^4$, and $R^8$ is ($C_1$-$C_3$)alkyl substituted with ($C_4$-$C_7$)cycloalkyl.

In some embodiments, each of $R^2$, $R^3$, $R^5$, $R^6$, $R^7$, $R^9$, $R^{10}$ and $R^{11}$ is independently ($C_1$-$C_3$)alkyl. In some embodiments, each of $R^2$, $R^5$, $R^7$, $R^9$, and $R^{11}$ is ($C_3$)alkyl. In some embodiments, each of $R^3$, $R^6$, and $R^{10}$ is ($C_1$)alkyl.

In some embodiments, each of $X^1$, $X^2$, $X^3$, $X^4$, $X^5$ and $X^6$ is independently H or ($C_1$-$C_6$)alkyl. In some embodiments, each of $X^1$, $X^2$, $X^3$, $X^4$, $X^5$ and $X^6$ is H. In some embodiments, at least one of $X^1$, $X^2$, $X^3$, $X^4$, $X^5$ and $X^6$ is ($C_1$-$C_6$)alkyl and the other are H. In some embodiments, at least one of $X^1$, $X^2$, $X^3$, $X^4$, $X^5$ and $X^6$ is ($C_1$-$C_3$)alkyl and the other are H. In some embodiments, at least one of $X^1$, $X^2$, $X^3$, $X^4$, $X^5$ and $X^6$ is ($C_1$)alkyl and the other are H.

In some embodiments, $aa_2$ is a natural amino acid. In other embodiments, $aa_2$ is an unnatural amino acid. In some embodiments, $aa_2$ comprises a functional group selected from —$NH_2$, —SH, —OH or —COOH. In some embodiments, $aa_1$ comprises —$NH_2$. In some embodiments, $aa_1$ comprises —SH. In some embodiments, $aa_1$ comprises —OH. In some embodiments, $aa_1$ comprises —COOH. In some embodiments, $aa_2$ is valine. In other embodiments, $aa_2$ is threonine optionally substituted with a Protecting Group or a Linking Unit. In some embodiments, $aa_2$ is threonine. In other embodiments, $aa_2$ is threonine substituted with a Protecting Group. In other embodiments, $aa_2$ is threonine substituted with a Linking Unit. In other embodiments, $aa_2$ is tyrosine optionally substituted with a Protecting Group or a Linking Unit. In some embodiments, $aa_2$ is tyrosine. In other embodiments, $aa_2$ is tyrosine substituted with a Protecting Group. In other embodiments, $aa_2$ is tyrosine substituted with a Linking Unit. In some embodiments, $aa_2$ is 4-aminophenylalanine optionally substituted with a Protecting Group or a Linking Unit. In some embodiments, $aa_2$ is 4-aminophenylalanine. In other embodiments, $aa_2$ is 4-aminophenylalanine substituted with a Protecting Group. In other embodiments, $aa_2$ is 4-aminophenylalanine substituted with a Linking Unit. In some embodiments, $aa_2$ is 3-aminophenylalanine optionally substituted with a Protecting Group or a Linking Unit. In some embodiments, $aa_2$ is 3-aminophenylalanine. In other embodiments, $aa_2$ is 3-aminophenylalanine substituted with a Protecting Group. In other embodiments, $aa_2$ is 3-aminophenylalanine substituted with a Linking Unit. In some embodiments, $aa_2$ is 2-aminophenylalanine optionally substituted with a Protecting Group or a Linking Unit. In some embodiments, $aa_2$ is 2-aminophenylalanine. In other embodiments, $aa_2$ is 2-aminophenylalanine substituted with a Protecting Group. In other embodiments, $aa_2$ is 2-aminophenylalanine substituted with a Linking Unit.

In some embodiments, the Linking Unit comprises a cleavable linker. In some embodiments, the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage. In some embodiments, the cleavable linker comprises a glycosidic bond, a hydrazone, a cathepsin-B-cleavable peptide, a disulfide or an ester bond. In some embodiments, the cleavable linker comprises glucuronide.

In some embodiments, $A_a$ is maleimidocaproyl.
In some embodiments, $W_w$ is Valine-Citrulline.
In some embodiments, $Y_y$ is p-aminobenzyloxycarbonyl.

In some embodiments, $A_a$ is maleimidocaproyl, $W_w$ is Valine-Citrulline and $Y_y$ is p-aminobenzyloxycarbonyl.

In some embodiments, the Linking Unit comprises a monoclonal antibody.

In one embodiment, at least one of $R^1$, $R^4$, and $R^8$ is ($C_1$-$C_4$)alkyl and each of $R^2$, $R^3$, $R^5$, $R^6$, $R^7$, $R^9$, $R^{10}$ and $R^{11}$ is independently ($C_1$-$C_3$)alkyl. In one embodiment, at least two of $R^1$, $R^4$, and $R^8$ are ($C_1$-$C_4$)alkyl and each of $R^2$, $R^3$, $R^5$, $R^6$, $R^7$, $R^9$, $R^{10}$ and $R^{11}$ is independently ($C_1$-$C_3$)alkyl. In another embodiment, each of $R^1$, $R^4$, and $R^8$ is ($C_1$-$C_4$)alkyl and each of $R^2$, $R^3$, $R^5$, $R^6$, $R^7$, $R^9$, $R^{10}$ and $R^{11}$ is independently ($C_1$-$C_3$)alkyl. In another embodiment, at least one of $R^1$, $R^4$, and $R^8$ is ($C_4$)alkyl and each of $R^2$, $R^3$, $R^5$, $R^6$, $R^7$, $R^9$, $R^{10}$ and $R^{11}$ is independently ($C_1$-$C_3$)alkyl. In another embodiment, at least two of $R^1$, $R^4$, and $R^8$ are ($C_4$)alkyl and each of $R^2$, $R^3$, $R^5$, $R^6$, $R^7$, $R^9$, $R^{10}$ and $R^{11}$ is independently ($C_1$-$C_3$)alkyl. In another embodiment, each of $R^1$, $R^4$, and $R^8$ is ($C_4$)alkyl and each of $R^2$, $R^3$, $R^5$, $R^6$, $R^7$, $R^9$, $R^{10}$ and $R^{11}$ is independently ($C_1$-$C_3$)alkyl.

In one embodiment, at least one of $R^1$, $R^4$, and $R^8$ is ($C_1$-$C_4$)alkyl and each of $R^2$, $R^5$, $R^7$, $R^9$, and $R^{11}$ is ($C_1$)alkyl. In another embodiment, at least two of $R^1$, $R^4$, and $R^8$ are ($C_1$-$C_4$)alkyl and each of $R^2$, $R^5$, $R^7$, $R^9$, and $R^{11}$ is ($C_1$)alkyl. In another embodiment, each of $R^1$, $R^4$, and $R^8$ is ($C_1$-$C_4$)alkyl and each of $R^2$, $R^5$, $R^7$, $R^9$, and $R^{11}$ is ($C_1$)alkyl. In another embodiment, at least one of $R^1$, $R^4$, and $R^8$ is ($C_4$)alkyl and each of $R^2$, $R^5$, $R^7$, $R^9$, and $R^{11}$ is ($C_1$)alkyl. In another embodiment, at least two of $R^1$, $R^4$, and $R^8$ are ($C_4$)alkyl and each of $R^2$, $R^5$, $R^7$, $R^9$, and $R^{11}$ is ($C_1$)alkyl. In another embodiment, each of $R^1$, $R^4$, and $R^8$ is ($C_4$)alkyl and each of $R^2$, $R^5$, $R^7$, $R^9$, and $R^{11}$ is ($C_1$)alkyl.

In one embodiment, at least one of $R^1$, $R^4$, and $R^8$ is ($C_1$-$C_4$)alkyl and each of $R^3$, $R^6$, and $R^{10}$ is ($C_3$)alkyl. In another embodiment, at least two of $R^1$, $R^4$, and $R^8$ are ($C_1$-$C_4$)alkyl and each of $R^3$, $R^6$, and $R^{10}$ is ($C_3$)alkyl. In another embodiment, each of $R^1$, $R^4$, and $R^8$ is ($C_1$-$C_4$)alkyl and each of $R^3$, $R^6$, and $R^{10}$ is ($C_3$)alkyl. In another embodiment, at least one of $R^1$, $R^4$, and $R^8$ is ($C_4$)alkyl and each of $R^3$, $R^6$, and $R^{10}$ is ($C_3$)alkyl. In another embodiment, at least two of $R^1$, $R^4$, and $R^8$ are ($C_4$)alkyl and each of $R^3$, $R^6$, and $R^{10}$ is ($C_3$)alkyl. In another embodiment, each of $R^1$, $R^4$, and $R^8$ is ($C_4$)alkyl and each of $R^3$, $R^6$, and $R^{10}$ is ($C_3$)alkyl.

In one embodiment, at least one of $R^1$, $R^4$, and $R^8$ is ($C_1$-$C_3$)alkyl substituted with ($C_4$-$C_7$)cycloalkyl and each of $R^2$, $R^5$, $R^7$, $R^9$, and $R^{11}$ is ($C_1$)alkyl. In another embodiment, at least two of $R^1$, $R^4$, and $R^8$ are ($C_1$-$C_3$)alkyl substituted with ($C_4$-$C_7$)cycloalkyl and each of $R^2$, $R^5$, $R^7$, $R^9$, and $R^{11}$ is ($C_1$)alkyl. In another embodiment, each of $R^1$, $R^4$, and $R^8$ is ($C_1$-$C_3$)alkyl substituted with ($C_4$-$C_7$)cycloalkyl and each of $R^2$, $R^5$, $R^7$, $R^9$, and $R^{11}$ is ($C_1$)alkyl.

In one embodiment, at least one of $R^1$, $R^4$, and $R^8$ is ($C_1$-$C_3$)alkyl substituted with ($C_4$-$C_7$)cycloalkyl and each of $R^2$, $R^5$, $R^7$, $R^9$, and $R^{11}$ is ($C_1$)alkyl. In another embodiment, at least two of $R^1$, $R^4$, and $R^8$ are ($C_1$-$C_3$)alkyl substituted with ($C_4$-$C_7$)cycloalkyl and each of $R^2$, $R^5$, $R^7$, $R^9$, and $R^{11}$ is ($C_1$)alkyl. In another embodiment, each of $R^1$, $R^4$, and $R^8$ is ($C_1$-$C_3$)alkyl substituted with ($C_4$-$C_7$)cycloalkyl and each of $R^2$, $R^5$, $R^7$, $R^9$, and $R^{11}$ is ($C_1$)alkyl.

In one embodiment, at least one of $R^1$, $R^4$, and $R^8$ is ($C_1$-$C_3$)alkyl substituted with ($C_4$-$C_7$)cycloalkyl and each of $R^3$, $R^6$, and $R^{10}$ is ($C_3$)alkyl. In another embodiment, at least two of $R^1$, $R^4$, and $R^8$ are ($C_1$-$C_3$)alkyl substituted with ($C_4$-$C_7$)cycloalkyl and each of $R^3$, $R^6$, and $R^{10}$ is ($C_3$)alkyl. In another embodiment, each of $R^1$, $R^4$, and $R^8$ is ($C_1$-$C_3$)alkyl substituted with ($C_4$-$C_7$)cycloalkyl and each of $R^3$, $R^6$, and $R^{10}$ is ($C_3$)alkyl.

In one embodiment, at least one of $R^1$, $R^4$, and $R^8$ is $(C_1-C_4)$alkyl or $(C_1-C_3)$alkyl substituted with $(C_4-C_7)$cycloalkyl and each of $R^2$, $R^3$, $R^5$, $R^6$, $R^7$, $R^9$, $R^{10}$ and $R^{11}$ is independently $(C_1-C_3)$alkyl. In another embodiment, one of $R^1$, $R^4$, and $R^8$ is $(C_1-C_4)$alkyl and the other two are $(C_1-C_3)$alkyl substituted with $(C_4-C_7)$cycloalkyl and each of $R^2$, $R^3$, $R^5$, $R^6$, $R^7$, $R^9$, $R^{10}$ and is independently $(C_1-C_3)$alkyl. In another embodiment, two of $R^1$, $R^4$, and $R^8$ are $(C_1-C_4)$alkyl and the other is $(C_1-C_3)$alkyl substituted with $(C_4-C_7)$cycloalkyl and each of $R^2$, $R^3$, $R^5$, $R^6$, $R^7$, $R^9$, $R^{10}$ and $R^{11}$ is independently $(C_1-C_3)$alkyl. In another embodiment, each of $R^1$, $R^4$, and $R^8$ is $(C_1-C_4)$alkyl and each of $R^2$, $R^3$, $R^5$, $R^6$, $R^7$, $R^9$, $R^{10}$ and $R^{11}$ is independently $(C_1-C_3)$alkyl. In another embodiment, each of $R^1$, $R^4$, and $R^8$ is $(C_1-C_3)$alkyl substituted with $(C_4-C_7)$cycloalkyl and each of $R^2$, $R^3$, $R^5$, $R^6$, $R^7$, $R^9$, $R^{10}$ and $R^{11}$ is independently $(C_1-C_3)$alkyl.

In one embodiment, at least one of $R^1$, $R^4$, and $R^8$ is $(C_1-C_4)$alkyl or $(C_1-C_3)$alkyl substituted with $(C_4-C_7)$cycloalkyl and each of $R^2$, $R^5$, $R^7$, $R^9$, and $R^{11}$ is $(C_1)$alkyl. In another embodiment, one of $R^1$, $R^4$, and $R^8$ is $(C_1-C_4)$alkyl and the other two are $(C_1-C_3)$alkyl substituted with $(C_4-C_7)$cycloalkyl and each of $R^2$, $R^5$, $R^7$, $R^9$, and $R^{11}$ is $(C_1)$alkyl. In another embodiment, two of $R^1$, $R^4$, and $R^8$ are $(C_1-C_4)$alkyl and the other is $(C_1-C_3)$alkyl substituted with $(C_4-C_7)$cycloalkyl and each of $R^2$, $R^5$, $R^7$, $R^9$, and $R^{11}$ is $(C_1)$alkyl. In another embodiment, each of $R^1$, $R^4$, and $R^8$ is $(C_1-C_4)$alkyl and each of $R^2$, $R^5$, $R^7$, $R^9$, and $R^{11}$ is $(C_1)$alkyl. In another embodiment, each of $R^1$, $R^4$, and $R^8$ is $(C_1-C_3)$alkyl substituted with $(C_4-C_7)$cycloalkyl and each of $R^2$, $R^5$, $R^7$, $R^9$, and $R^{11}$ is $(C_1)$alkyl.

In one embodiment, at least one of $R^1$, $R^4$, and $R^8$ is $(C_1-C_4)$alkyl or $(C_1-C_3)$alkyl substituted with $(C_4-C_7)$cycloalkyl and each of $R^3$, $R^6$, and $R^{10}$ is $(C_3)$alkyl. In another embodiment, one of $R^1$, $R^4$, and $R^8$ is $(C_1-C_4)$alkyl and the other two are $(C_1-C_3)$alkyl substituted with $(C_4-C_7)$cycloalkyl and each of $R^3$, $R^6$, and $R^{10}$ is $(C_3)$alkyl. In another embodiment, two of $R^1$, $R^4$, and $R^8$ are $(C_1-C_4)$alkyl and the other is $(C_1-C_3)$alkyl substituted with $(C_4-C_7)$cycloalkyl and each of $R^3$, $R^6$, and $R^{10}$ is $(C_3)$alkyl. In another embodiment, each of $R^1$, $R^4$, and $R^8$ is $(C_1-C_4)$alkyl and each of $R^3$, $R^6$, and $R^{10}$ is $(C_3)$alkyl. In another embodiment, each of $R^1$, $R^4$, and $R^8$ is $(C_1-C_3)$alkyl substituted with $(C_4-C_7)$cycloalkyl and each of $R^3$, $R^6$, and $R^{10}$ is $(C_3)$alkyl.

In one embodiment, at least two of $R^1$, $R^4$, and $R^8$ are $(C_1-C_4)$alkyl and each of $X^1$, $X^2$, $X^3$, $X^4$, $X^5$ and $X^6$ is independently H or $(C_1-C_6)$alkyl. In another embodiment, each of $R^1$, $R^4$, and $R^8$ is $(C_1-C_4)$alkyl and each of $X^1$, $X^2$, $X^3$, $X^4$, $X^5$ and $X^6$ is independently H or $(C_1-C_6)$alkyl. In another embodiment, at least one of $R^1$, $R^4$, and $R^8$ is $(C_4)$alkyl and each of $X^1$, $X^2$, $X^3$, $X^4$, $X^5$ and $X^6$ is independently H or $(C_1-C_6)$alkyl. In another embodiment, at least two of $R^1$, $R^4$, and $R^8$ are $(C_4)$alkyl and each of $X^1$, $X^2$, $X^3$, $X^4$, $X^5$ and $X^6$ is independently H or $(C_1-C_6)$alkyl. In another embodiment, each of $R^1$, $R^4$, and $R^8$ is $(C_4)$alkyl and each of $X^1$, $X^2$, $X^3$, $X^4$, $X^5$ and $X^6$ is independently H or $(C_1-C_6)$alkyl.

In one embodiment, at least two of $R^1$, $R^4$, and $R^8$ are $(C_1-C_4)$alkyl and each of $X^1$, $X^2$, $X^3$, $X^4$, $X^5$ and $X^6$ is H. In another embodiment, each of $R^1$, $R^4$, and $R^8$ is $(C_1-C_4)$alkyl and each of $X^1$, $X^2$, $X^3$, $X^4$, $X^5$ and $X^6$ is H. In another embodiment, at least one of $R^1$, $R^4$, and $R^8$ is $(C_4)$alkyl and each of $X^1$, $X^2$, $X^3$, $X^4$, $X^5$ and $X^6$ is H. In another embodiment, at least two of $R^1$, $R^4$, and $R^8$ are $(C_4)$alkyl and each of $X^1$, $X^2$, $X^3$, $X^4$, $X^5$ and $X^6$ is H. In another embodiment, each of $R^1$, $R^4$, and $R^8$ is $(C_4)$alkyl and each of $X^1$, $X^2$, $X^3$, $X^4$, $X^5$ and $X^6$ is H.

In one embodiment, at least two of $R^1$, $R^4$, and $R^8$ are $(C_1-C_4)$alkyl and at least one of $X^1$, $X^2$, $X^3$, $X^4$, $X^5$ and $X^6$ is $(C_1)$alkyl and the other are H. In another embodiment, each of $R^1$, $R^4$, and $R^8$ is $(C_1-C_4)$alkyl and at least one of $X^1$, $X^2$, $X^3$, $X^4$, $X^5$ and $X^6$ is $(C_1)$alkyl and the other are H. In another embodiment, at least one of $R^1$, $R^4$, and $R^8$ is $(C_4)$alkyl and at least one of $X^1$, $X^2$, $X^3$, $X^4$, $X^5$ and $X^6$ is $(C_1)$alkyl and the other are H. In another embodiment, at least two of $R^1$, $R^4$, and $R^8$ are $(C_4)$alkyl and at least one of $X^1$, $X^2$, $X^3$, $X^4$, $X^5$ and $X^6$ is $(C_1)$alkyl and the other are H. In another embodiment, each of $R^1$, $R^4$, and $R^8$ is $(C_4)$alkyl and at least one of $X^1$, $X^2$, $X^3$, $X^4$, $X^5$ and $X^6$ is $(C_1)$alkyl and the other are H.

In one embodiment, at least one of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl. In another embodiment, at least two of $R^1$, $R^4$, and $R^8$ are $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl. In another embodiment, each of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl.

In one embodiment, at least one of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is H. In another embodiment, at least two of $R^1$, $R^4$, and $R^8$ are $(C_1-C_3)$alkyl substituted with $(C_4-C_7)$cycloalkyl and each of $X^1$, $X^2$, $X^3$, $X^4$, $X^5$ and $X^6$ is H. In another embodiment, each of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is H.

In one embodiment, at least one of $R^1$, $R^4$, and $R^8$ is $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H. In another embodiment, at least two of $R^1$, $R^4$, and $R^8$ are $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H. In another embodiment, each of $R^1$, $R^4$, and $R^8$ is $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H.

In one embodiment, at least one of $R^1$, $R^4$, and $R^8$ is $(C_1-C_4)$alkyl or $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl. In another embodiment, one of $R^1$, $R^4$, and $R^8$ is $(C_1-C_4)$alkyl and the other two are $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl. In another embodiment, two of $R^1$, $R^4$, and $R^8$ are $(C_1-C_4)$alkyl and the other is $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl. In another embodiment, each of $R^1$, $R^4$, and $R^8$ is $(C_1-C_4)$alkyl and each of $X^1$, $X^2$, $X^3$, $X^4$, $X^5$ and $X^6$ is independently H or $(C_1-C_6)$alkyl. In another embodiment, each of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is independently H or $(C_1-C_6)$alkyl.

In one embodiment, at least one of $R^1$, $R^4$, and $R^8$ is $(C_1-C_4)$alkyl or $(C_1-C_3)$alkyl substituted with $(C_4-C_7)$cycloalkyl 1 and each of $X^1$, $X^2$, $X^3$, $X^4$, $X^5$ and $X^6$ is H. In another embodiment, one of $R^1$, $R^4$, and $R^8$ is $(C_1-C_4)$alkyl and the other two are $(C_1-C_3)$alkyl substituted with $(C_4-C_7)$cycloalkyl and each of $X^1$, $X^2$, $X^3$, $X^4$, $X^5$ and $X^6$ is H. In another embodiment, two of $R^1$, $R^4$, and $R^8$ are $(C_1-C_4)$alkyl and the other is $(C_1-C_3)$alkyl substituted with $(C_4-C_7)$cycloalkyl and each of $X^1$, $X^2$, $X^3$, $X^4$, $X^5$ and $X^6$ is H. In another embodiment, each of $R^1$, $R^4$, and $R^8$ is $(C_1-C_4)$alkyl and each of $X^1$, $X^2$, $X^3$, $X^4$, $X^5$ and $X^6$ is H. In another embodiment, each of $R^1$, $R^4$, and $R^8$ is $(C_1-C_3)$alkyl substituted with $(C_4-C_7)$cycloalkyl and each of $X^1$, $X^2$, $X^3$, $X^4$, $X^5$ and $X^6$ is H.

In one embodiment, at least one of $R^1$, $R^4$, and $R^8$ is $(C_1-C_4)$alkyl or $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H. In another embodiment, one of $R^1$, $R^4$, and $R^8$ is $(C_1-C_4)$alkyl and the other two are $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H. In another embodiment, two of $R^1$, $R^4$, and $R^8$ are $(C_1-C_4)$alkyl and the other is $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H. In another embodiment, each of $R^1$, $R^4$, and $R^8$ is $(C_1-C_4)$alkyl and at least one of $X^1$, $X^2$, $X^3$, $X^4$, $X^5$ and $X^6$ is $(C_1)$alkyl and the other are H. In another embodiment, each of $R^1$, $R^4$, and $R^8$ is $(C_1-C_3)$alkyl substituted with $(C_4-C_7)$cycloalkyl and at least one of $X^1$, $X^2$, $X^3$, $X^4$, $X^5$ and $X^6$ is $(C_1)$alkyl and the other are H.

In one embodiment, each of $R^2$, $R^3$, $R^5$, $R^6$, $R^7$, $R^9$, $R^{10}$ and $R^{11}$ is independently $(C_1-C_3)$alkyl and each of $X^1$, $X^2$, $X^3$, $X^4$, $X^5$ and $X^6$ is independently H or $(C_1-C_6)$alkyl. In another embodiment, each of $R^2$, $R^5$, $R^7$, $R^9$, and $R^{11}$ is $(C_1)$alkyl and each of $X^1$, $X^2$, $X^3$, $X^4$, $X^5$ and $X^6$ is independently H or $(C_1-C_6)$alkyl. In another embodiment, each of $R^3$, $R^6$, and $R^{10}$ is $(C_3)$alkyl and each of $X^1$, $X^2$, $X^3$, $X^4$, $X^5$ and $X^6$ is independently H or $(C_1-C_6)$alkyl.

In one embodiment, each of $R^2$, $R^3$, $R^5$, $R^6$, $R^7$, $R^9$, $R^{10}$ and $R^{11}$ is independently $(C_1-C_3)$alkyl and each of $X^1$, $X^2$, $X^4$, $X^5$ and $X^6$ is H. In another embodiment, each of $R^2$, $R^5$, $R^7$, $R^9$, and $R^{11}$ is $(C_1)$alkyl and each of $X^1$, $X^2$, $X^3$, $X^4$, $X^5$ and $X^6$ is H. In another embodiment, each of $R^3$, $R^6$, and $R^{10}$ is $(C_3)$alkyl and each of $X^1$, $X^2$, $X^3$, $X^4$, $X^5$ and $X^6$ is H.

In one embodiment, each of $R^2$, $R^3$, $R^5$, $R^6$, $R^7$, $R^9$, $R^{10}$ and $R^{11}$ is independently $(C_1-C_3)$alkyl and at least one of $X^1$, $X^2$, $X^3$, $X^4$, $X^5$ and $X^6$ is $(C_1)$alkyl and the other are H. In another embodiment, each of $R^2$, $R^3$, $R^5$, $R^6$, $R^7$, $R^9$, $R^{10}$ and $R^{11}$ is independently $(C_1-C_3)$alkyl and at least one of $X^1$, $X^2$, $X^3$, $X^4$, $X^5$ and $X^6$ is $(C_1)$alkyl and the other are H. In another embodiment, each of $R^2$, $R^3$, $R^5$, $R^6$, $R^7$, $R^9$, $R^{10}$ and $R^{11}$ is independently $(C_1-C_3)$alkyl and at least one of $X^1$, $X^2$, $X^3$, $X^4$, $X^5$ and $X^6$ is $(C_1)$alkyl and the other are H. In another embodiment, each of $R^2$, $R^3$, $R^5$, $R^6$, $R^7$, $R^9$, $R^{10}$ and $R^{11}$ is independently $(C_1-C_3)$alkyl and at least one of $X^1$, $X^2$, $X^3$, $X^4$, $X^5$ and $X^6$ is $(C_1)$alkyl and the other are H.

In one embodiment, at least two of $R^1$, $R^4$, and $R^8$ are $(C_1-C_4)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^1$, $R^4$, and $R^8$ is $(C_1-C_4)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, at least one of $R^1$, $R^4$, and $R^8$ is $(C_4)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, at least two of $R^1$, $R^4$, and $R^8$ are $(C_4)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^1$, $R^4$, and $R^8$ is $(C_4)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit.

In one embodiment, at least one of $R^1$, $R^4$, and $R^8$ is $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, at least two of $R^1$, $R^4$, and $R^8$ are $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^1$, $R^4$, and $R^8$ is $(C_1-C_3)$alkyl substituted with $(C_4-C_7)$ cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit.

In one embodiment, at least one of $R^1$, $R^4$, and $R^8$ is $(C_1-C_4)$alkyl or $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, one of $R^1$, $R^4$, and $R^8$ is $(C_1-C_4)$alkyl and the other two are $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, two of $R^1$, $R^4$, and $R^8$ are $(C_1-C_4)$alkyl and the other is $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^1$, $R^4$, and $R^8$ is $(C_1-C_4)$alkyl $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^1$, $R^4$, and $R^8$ is $(C_1-C_3)$alkyl substituted with $(C_4-C_7)$cycloalkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit.

In one embodiment, each of $R^2$, $R^3$, $R^5$, $R^6$, $R^7$, $R^9$, $R^{10}$ and $R^{11}$ is independently $(C_1-C_3)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^2$, $R^5$, $R^7$, $R^9$, and $R^{11}$ is $(C_1)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $R^3$, $R^6$, and $R^{10}$ is $(C_3)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit.

In one embodiment, each of $X^1$, $X^2$, $X^3$, $X^4$, $X^5$ and $X^6$ is independently H or $(C_1-C_6)$alkyl and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, each of $X^1$, $X^2$, $X^3$, $X^4$, $X^5$ and $X^6$ is H and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit. In another embodiment, at least one of $X^1$, $X^2$, $X^3$, $X^4$, $X^5$ and $X^6$ is $(C_1)$alkyl and the other are H and $aa_1$ is valine, threonine optionally substituted with a Protecting Group or a Linking Unit, tyrosine optionally substituted with a Protecting Group or a Linking Unit, 4-aminophenylalanine optionally substituted with a Protecting Group or a Linking Unit, 3-aminophenylalanine optionally substituted with a Protecting Group or a Linking Unit or 2-aminophenylalanine optionally substituted with a Protecting Group or a Linking Unit.

In some embodiments, the present disclosure provides a compound of formula (IIa):

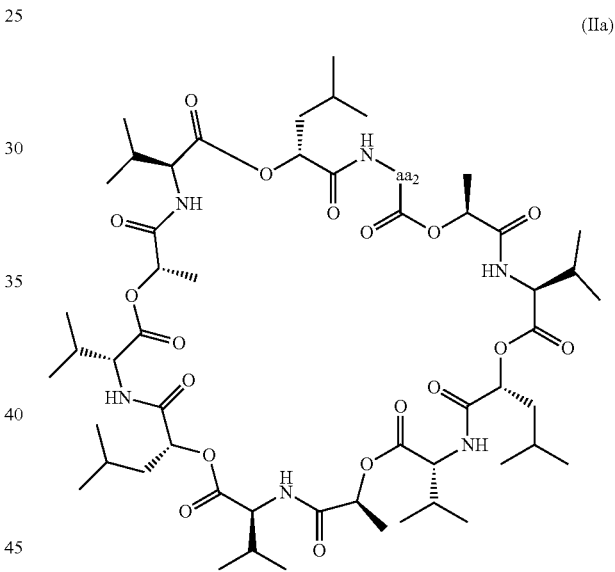

(IIa)

or a pharmaceutically acceptable salt thereof, wherein
$aa_2$ is valine, threonine optionally substituted with a protecting group or a Linking Unit, and tyrosine optionally substituted with a protecting group or a Linking Unit.

In some embodiments, $aa_2$ is valine. In other embodiments, $aa_2$ is threonine optionally substituted with a Protecting Group or a Linking Unit. In some embodiments, $aa_2$ is threonine. In other embodiments, $aa_2$ is threonine substituted with a Protecting Group. In other embodiments, $aa_2$ is threonine substituted with a Linking Unit. In other embodiments, $aa_2$ is tyrosine optionally substituted with a Protecting Group or a Linking Unit. In some embodiments, $aa_2$ is tyrosine. In other embodiments, $aa_2$ is tyrosine substituted with a Protecting Group. In other embodiments, $aa_2$ is tyrosine substituted with a Linking Unit.

In some embodiments, the Linking Unit comprises a cleavable linker. In some embodiments, the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage. In some embodiments, the cleavable linker comprises a glycosidic bond, a hydrazone, a cathepsin-B-cleavable peptide, a disulfide or an ester bond. In some embodiments, the cleavable linker comprises glucuronide.

In some embodiments, $A_a$ is maleimidocaproyl.
In some embodiments, $W_w$ is Valine-Citrulline.
In some embodiments, $Y_y$ is p-aminobenzyloxycarbonyl.
In some embodiments, $A_a$ is maleimidocaproyl, $W_w$ is Valine-Citrulline and $Y_y$ is p-aminobenzyloxycarbonyl.

In some embodiments, the Linking Unit comprises a monoclonal antibody.

In some embodiments, the present disclosure provides a compound of formula (IIb):

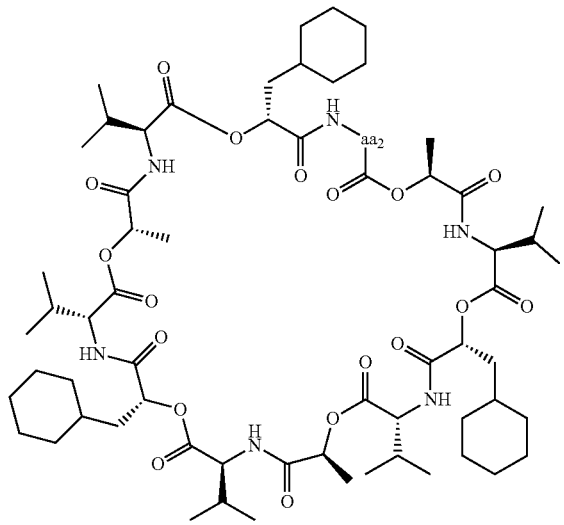

(IIb)

or a pharmaceutically acceptable salt thereof, wherein
aa$_2$ is valine, threonine optionally substituted with a protecting group or a Linking Unit, and tyrosine optionally substituted with a protecting group or a Linking Unit.

In some embodiments, aa$_2$ is valine. In other embodiments, aa$_2$ is threonine optionally substituted with a Protecting Group or a Linking Unit. In some embodiments, aa$_2$ is threonine. In other embodiments, aa$_2$ is threonine substituted with a Protecting Group. In other embodiments, aa$_2$ is threonine substituted with a Linking Unit. In other embodiments, aa$_2$ is tyrosine optionally substituted with a Protecting Group or a Linking Unit. In some embodiments, aa$_2$ is tyrosine. In other embodiments, aa$_2$ is tyrosine substituted with a Protecting Group. In other embodiments, aa$_2$ is tyrosine substituted with a Linking Unit.

In some embodiments, the Linking Unit comprises a cleavable linker. In some embodiments, the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage. In some embodiments, the cleavable linker comprises a glycosidic bond, a hydrazone, a cathepsin-B-cleavable peptide, a disulfide or an ester bond. In some embodiments, the cleavable linker comprises glucuronide.

In some embodiments, $A_a$ is maleimidocaproyl.
In some embodiments, $W_w$ is Valine-Citrulline.
In some embodiments, $Y_y$ is p-aminobenzyloxycarbonyl.

In some embodiments, $A_a$ is maleimidocaproyl, $W_w$ is Valine-Citrulline and $Y_y$ is p-aminobenzyloxycarbonyl.

In some embodiments, the Linking Unit comprises a monoclonal antibody.

In some embodiments, the present disclosure provides a compound of formula (IIc):

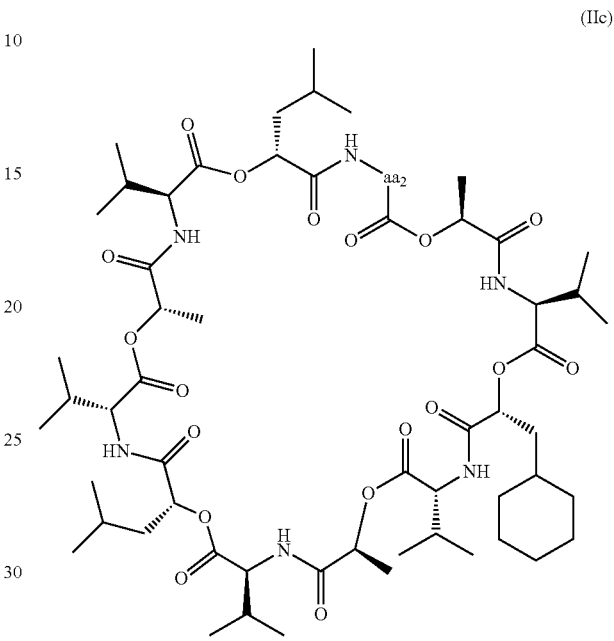

(IIc)

or a pharmaceutically acceptable salt thereof, wherein
aa$_2$ is valine, threonine optionally substituted with a protecting group or a Linking Unit, and tyrosine optionally substituted with a protecting group or a Linking Unit.

In some embodiments, aa$_2$ is valine. In other embodiments, aa$_2$ is threonine optionally substituted with a Protecting Group or a Linking Unit. In some embodiments, aa$_2$ is threonine. In other embodiments, aa$_2$ is threonine substituted with a Protecting Group. In other embodiments, aa$_2$ is threonine substituted with a Linking Unit. In other embodiments, aa$_2$ is tyrosine optionally substituted with a Protecting Group or a Linking Unit. In some embodiments, aa$_2$ is tyrosine. In other embodiments, aa$_2$ is tyrosine substituted with a Protecting Group. In other embodiments, aa$_2$ is tyrosine substituted with a Linking Unit.

In some embodiments, the Linking Unit comprises a cleavable linker. In some embodiments, the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage. In some embodiments, the cleavable linker comprises a glycosidic bond, a hydrazone, a cathepsin-B-cleavable peptide, a disulfide or an ester bond. In some embodiments, the cleavable linker comprises glucuronide.

In some embodiments, $A_a$ is maleimidocaproyl.
In some embodiments, $W_w$ is Valine-Citrulline.
In some embodiments, $Y_y$ is p-aminobenzyloxycarbonyl.
In some embodiments, $A_a$ is maleimidocaproyl, $W_w$ is Valine-Citrulline and $Y_y$ is p-aminobenzyloxycarbonyl.

In some embodiments, the Linking Unit comprises a monoclonal antibody.

Representative compounds of formulae (I) and (II) include:
Cyclo-[Val-D-Hica-D-Val-Lac]$_3$;
Cyclo-{Thr-D-Hica-D-Val-Lac-[Val-D-Hica-D-Val-Lac]$_2$};
Cyclo-{Tyr-D-Hica-D-Val-Lac-[Val-D-Hica-D-Val-Lac]$_2$};
Cyclo-[Val-D-Hcha-D-Val-Lac]3;
Cyclo-{Thr-D-Hcha-D-Val-Lac-[Val-D-Hcha-D-Val-Lac]$_2$};
Cyclo-{Tyr-D-Hcha-D-Val-Lac-[Val-D-Hcha-D-Val-Lac]$_2$};
Cyclo-{Thr-D-Hcha-D-Val-Lac-[Val-D-Hica-D-Val-Lac]$_2$};
Cyclo-{Tyr-D-Hcha-D-Val-Lac-[Val-D-Hica-D-Val-Lac]$_2$}; and
pharmaceutically acceptable salts thereof.

In one embodiment, the compound is

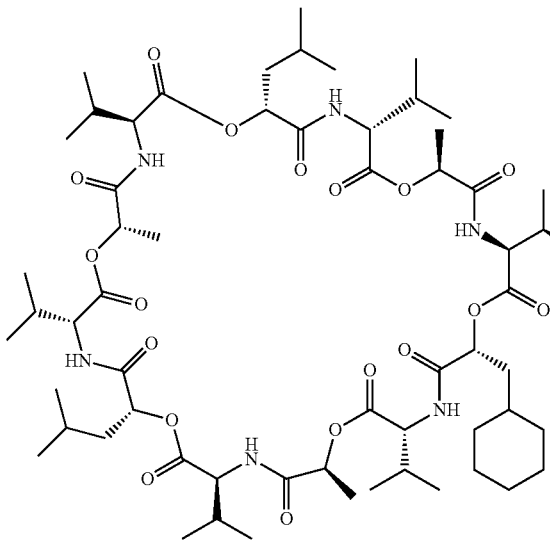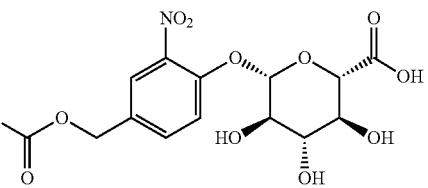

and a pharmaceutically acceptable salt thereof.

The compounds of this disclosure may be prepared by methods known to those skilled in the art, methods of Schemes I through IV, or the synthetic Examples set forth below.

Pharmaceutical Compositions

According to another embodiment, the present disclosure provides a pharmaceutical composition comprising a compound described herein or a pharmaceutically acceptable salt thereof and a pharmaceutically acceptable carrier.

The pharmaceutical composition of the disclosure may be formulated for administration in solid or liquid form, including those adapted for administration by oral, nasal, parenteral, rectal, topical, ocular, inhalation and intra-tumor administration. Parenteral administration includes subcutaneous injections, intravenous, intramuscular or intrasternal injection or infusion techniques. In one embodiment, the compositions are administered parenterally. In another embodiment, the compositions are administered intravenously.

The pharmaceutical composition of the disclosure may be in the form of a liquid, e.g., a solution, emulsion or suspension, pellets, powders, sustained-release formulations, or any other form suitable for use. The pharmaceutical composition may comprise sterile diluents such as water, saline solution, preferably physiological saline, Ringer's solution, isotonic sodium chloride, fixed oils such as synthetic mono- or digylcerides, which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids; agents for the adjustment of tonicity such as sodium chloride or dextrose; surfactants; preservatives; wetting agents; dispersing agents; suspending agents; stabilizers; solubilizing agents; local anesthetics, e.g., lignocaine; or isotonic agent.

It should be understood that a specific dosage and treatment regimen for any particular patient will depend upon a variety of factors, including the type of patient (e.g., human), the activity of the specific compound employed, the composition employed, the manner of administration, the age, body weight, general health, sex, diet, time of administration, rate of excretion, drug combination, and the judgment of the treating physician and the nature and the severity of the particular disorder being treated. The amount of active ingredients will also depend upon the particular compound in the composition. The amount of active ingredient can be determined by standard clinical techniques. In addition, in vitro or in vivo assays can optionally be employed to help identify optimal dosage ranges.

Preferably, the compositions are formulated so that a dosage of between about 0.01 to about 20 mg/kg body weight/day of the compound of formula (I) can be administered to a patient receiving the composition. In one embodiment, the dosage administered to the patient is between about 0.01 mg/kg and about 10 mg/kg of the patient's body weight. In another embodiment, the dosage administered to the patient is between about 0.1 mg/kg and about 10 mg/kg of the patient's body weight. In yet another embodiment, the dosage administered to the patient is between about 0.1 mg/kg and about 5 mg/kg of the patient's body weight. In yet another embodiment, the dosage administered is between about 0.1 mg/kg and about 3 mg/kg of the patient's body weight. In yet another embodiment, the dosage administered is between about 1 mg/kg and about 3 mg/kg of the patient's body weight.

The pharmaceutical compositions comprise an effective amount of a compound described herein such that a suitable dosage will be obtained. Typically, this amount is at least about 0.01% of a compound by weight of the composition. In a preferred embodiment, pharmaceutical compositions are prepared so that a parenteral dosage unit contains from about 0.01% to about 2% by weight of the compound of the disclosure.

For intravenous administration, the pharmaceutical composition may comprise from about 0.01 to about 100 mg of a compound described herein per kg of the patient's body weight. In one aspect, the composition may include from about 1 to about 100 mg of a compound described herein per kg of the patient's body weight. In another aspect, the amount administered will be in the range from about 0.1 to about 25 mg of a compound described herein per kg of body weight.

The pharmaceutical compositions of the present disclosure may optionally further comprise a second therapeutic agent in a therapeutically effective amount. The second therapeutic agent includes those that are known and those discovered to be effective in the treatment of cancer, a bacterial infection or a fungal infection. In some embodiments, the second therapeutic agent is selected from the group consisting of a tubulin-forming inhibitor, a topoisomerase inhibitor, and a DNA binder.

Methods Of Use

The present disclosure also provides methods of using the compounds described herein or pharmaceutical compositions thereof. The compounds and compositions are useful for killing or inhibiting the proliferation of tumor cells or cancer cells. The compounds and compositions are also useful for treating cancer in a patient. In addition, the compounds and compositions are useful for inhibiting bacterial or fungal growth. The compounds and compositions are useful in treating a bacterial or fungal infection in a patient.

In some embodiments, the present disclosure provides methods of killing or inhibiting the proliferation of tumor cells or cancer cells. In some embodiments, the method comprises contacting the tumor cells or cancer cells with a compound described herein, or a pharmaceutically acceptable salt thereof, in an amount effective to kill or inhibit the proliferation of the tumor cells or cancer cells. In alternate embodiments, the method comprises contacting the tumor cells or cancer cells with a pharmaceutical composition comprising a compound described herein in an amount effective to kill or inhibit the proliferation of the tumor cells or cancer cells.

In some embodiments, the method further comprises contacting the cells with an effective amount of a second therapeutic agent or a pharmaceutical composition thereof. In one embodiment, the second therapeutic agent can be selected from the group consisting of a tubulin-forming inhibitor, a topoisomerase inhibitor, and a DNA binder.

The cells may be contacted with the compound described herein and the second therapeutic agent simultaneously in either the same or different compositions or sequentially in any order. The amounts of compound described herein and the second therapeutic agent and the relative timings of their contact will be selected in order to achieve the desired combined effect.

In another embodiment, the present disclosure provides a method of determining inhibition of cellular proliferation by a compound described herein. The method comprises contacting cells in a cell culture medium with the compound described herein and measuring the cytotoxic activity of the compound, whereby proliferation of the cells is inhibited. In some embodiments, the method further comprises culturing the cells for a period from about 6 hours to about 5 days.

Suitable cell lines are known to those skilled in the art and include those used for evaluating other anti-cancer drugs. Such cell lines include, but are not limited to, 786-O (a renal cell carcinoma); Caki-1 (a renal cell carcinoma); L428 (Hodgkin's disease); UMRC-3 (renal cell carcinoma); LP-1 (human myeloma); U251 (glioblastoma cell line); BXPC-3 (pancreas); MCF-7 (breast); SF-268 (CNS); NCI-H460 (lung); KM20L2 (colon); and DU-145 (prostate). In some embodiments, the cells are obtained from a patient having a disease to be treated (e.g., cancer) or from a relevant cell line.

In another embodiment, the present disclosure provides a method of measuring cell viability in the presence of a compound described herein. The method comprises contacting cells in a cell culture medium with the compound of described herein, culturing the cells for a period from about 6 hours to about 5 days, preferably 96 hours; and measuring cell viability. In some embodiments, the cells are obtained from a patient having a disease to be treated (e.g., cancer) or from a relevant cell line.

In another embodiment, the present disclosure provides a method for treating cancer in a patient. In some embodiments, the method comprises administering to the patient a compound described herein, or a pharmaceutically acceptable salt thereof, in an amount effective to treat cancer. In other embodiments, the method comprises administering to the patient a composition comprising a compound described herein in an amount effective to treat cancer.

In some embodiments, the patient receives an additional treatment, such as radiation therapy, surgery, chemotherapy with another chemotherapeutic agent or combinations thereof. In some embodiments, the compound of the disclosure is administered concurrently with the chemotherapeutic agent or with radiation therapy or with surgery. In other embodiments, the chemotherapeutic agent or radiation therapy or surgery is administered or performed prior or subsequent to administration of a compound of the disclosure.

In some embodiments, the method for treating cancer further comprises administering to the patient an effective amount of a second therapeutic agent, e.g., a chemotherapeutic agent. Any one or a combination of the chemotherapeutic agents, such a standard of care chemotherapeutic agent(s), can be administered. In some embodiments, the chemotherapeutic agent may be selected from the group consisting of a tubulin-forming inhibitor, a topoisomerase inhibitor, and a DNA binder.

The compound described herein and the chemotherapeutic agent may be administered simultaneously in either the same or different pharmaceutical composition or sequentially in any order. The amounts of compound described herein and the chemotherapeutic agent and the relative timings of their administration will be selected in order to achieve the desired combined effect.

In another embodiment, the present disclosure provides a method of inhibiting the growth of tumor cells that overexpress a tumor-associated antigen in a patient. In some embodiments, the method comprises administering to the patient a compound described herein conjugated to an antibody that is specific for said tumor-associated antigen, wherein the compound described herein is administered in amount effective to inhibit growth of tumor cells in the patient. In alternate embodiments, the method comprises administering to the patient a pharmaceutical composition comprising a compound described herein conjugated to an antibody that is specific for said tumor-associated antigen, wherein the compound described herein is administered in amount effective to inhibit growth of tumor cells in the patient. The method may optionally further comprises administering to the patient a chemotherapeutic agent, or a pharmaceutical composition thereof, in an amount effective to inhibit the growth of tumor cells in the patient.

In some embodiments, the compound sensitizes the tumor cells to the chemotherapeutic agent.

In some embodiments, the compound induces cell death. In other embodiments, the compound induces apoptosis.

In some embodiments, the tumor cells are associated with a cancer selected from the group consisting of breast, ovarian, stomach, endometrial, salivary gland, lung, kidney, colon, colorectal, thyroid, pancreatic, prostate, central nervous system and bladder cancer.

In some embodiments, the compound described herein is conjugated to an antibody selected from the group consisting of CD19, CD20, CD30, CD33, CD70, BCMA, Glypican-3, Liv-1 and Lewis Y.

In some embodiments, the present disclosure provides methods of inhibiting bacterial or fungal growth in a sample. In some embodiments, the method comprises contacting the sample with a compound described herein, or a pharmaceutically acceptable salt thereof, in an amount effective to inhibit growth of bacteria or fungus in the sample. In alternate embodiments, the method comprises contacting the sample with a pharmaceutical composition comprising a compound described herein in an amount effective to inhibit the growth of bacteria or fungus in the sample.

In some embodiments, the present disclosure provides methods of treating a bacterial or fungal infection in a patient. In some embodiments, the method comprises administering to the patient a compound described herein, or a pharmaceutically acceptable salt thereof, in an amount effective to treat the bacterial or fungal infection. In other embodiments, the method comprises administering to the patient a composition comprising a compound described herein in an amount effective to the bacterial or fungal infection.

The compounds of the present disclosure may be used in methods for inhibiting bacterial or fungal growth and in methods for treating bacterial or fungal infections. The compounds are used in a method for inhibiting bacterial growth in one embodiment, in a method for treating a bacterial infection in a second embodiment, in a method for inhibiting fungal growth in a third embodiment, and in a method for treating a fungal infection in a four embodiment. In each embodiment of this paragraph in which the compounds inhibit bacterial growth or treat a bacterial infection, the bacteria is selected from gram-negative bacteria or gram-positive bacteria. In some embodiments, the bacteria or fungi is selected from vancomycin-resistant *Enterococcus faecalis*, *Staphylococcus aureus*, methicillin-resistant *Staphylococcus aureus*, *Streptococcus pneumoniae*, multi-drug-resistant *Streptococcus pneumoniae*, *Streptococcus pyogenes*, *Pseudomonas aeruginosa*, *Neisseria gonorrhoeae*, *Cryptococcus neoformans* and *Candida albicans*. In one embodiment, the bacteria is *Streptococcus pneumoniae* (including a penicillin-resistant strain and a multi-drug resistant strain) or *Streptococcus pyogenes*.

In some embodiments, the method for treating a bacterial or fungal infection further comprises administering to the patient an effective amount of a second therapeutic agent. Any one or a combination of the second therapeutic agent, such a standard of care therapeutic agent(s) for bacterial or fungal infections, can be administered.

Any compound or pharmaceutical composition described herein may be used in the methods of the present disclosure.

In some of the above methods, the compound described herein is administered to a patient in a composition comprising a pharmaceutically acceptable carrier. In some of these embodiments, the composition is administered intravenously. In certain embodiments, the compound is formulated in a unit dosage injectable form.

In preferred embodiments of each of the above methods, the patient is a human.

In an additional embodiment, the present disclosure provides the use of a compound of described herein in the manufacture of a medicament for the treatment of any of the above mentioned conditions. In one embodiment, the medicament is useful for the treatment of any of the above mentioned cancers. In another embodiment, the medicament is useful for the treatment of a bacterial or fungal infection. It will be appreciated that a compound described herein and one or more second therapeutic agents may be used in the manufacture of the medicament.

In additional embodiments, the present disclosure provides an article of manufacture comprising a compound described herein, a container, and a package insert or label indicating that the compound can be used to treat cancer characterized by the overexpression of at least one tumor-associated antigen.

In additional embodiments, the present disclosure provides an article of manufacture comprising a compound described herein, a container, and a package insert or label indicating that the compound can be used to treat a bacterial or fungal infection.

The term "package insert" is used to refer to instructions customarily included in commercial packages of therapeutic products that contain information about the indication(s), usage, dosage, administration, contraindications and/or warnings concerning the use of such therapeutic products.

In order that this invention be more fully understood, the following examples are set forth. These examples are for the purpose of illustration only and are not to be construed as limiting the scope of the invention in any way.

EXAMPLES

Reagents and anhydrous solvents were purchased from Sigma-Aldrich Chemical Company and Alfa-Aesar Inc, and were used as received. Degussa type E101 NE/W was employed for 20% palladium hydroxide on carbon. The reactions were carried out under an atmosphere of nitrogen unless specified otherwise. Column chromatography was conducted using silica gel (E. Merck 60 Å, 230-400 mesh), applying a low-pressure stream of nitrogen. Analytical thin layer chromatography separations were carried out on glass plates coated with silica gel (Analtech, GHLF uniplates). The TLC chromatograms were visualized using UV (short wave) lamp irradiation or by immersing the plates in ceric ammonium molybdate (CAM) staining solution followed by heating with a heat gun.

Melting points are uncorrected and were determined with a Fischer-Johns melting point apparatus. Optical rotations were measured by use of a Perkin-Elmer 241 polarimeter, and the $[\alpha]_D$ values are given in $10^{-1}$ deg cm$^2$ g$^{-1}$. $^1$H and $^{13}$C NMR spectra were recorded on a Varian Unity INOVA 400 instrument with deuterated solvents; $^1$H NMR chemical shifts were recorded relative to residual CHCl$_3$ at 7.26 ppm, or MeOH 3.31 ppm; $^{13}$C NMR chemical shifts were reported relative to residual CHCl$_3$ at 77.16 ppm, or MeOH 49.00 ppm. High resolution mass spectra were obtained in the Arizona State University CLAS High Resolution Mass Spectrometry Laboratory.

Compounds 7a, 8a and 8b were synthesized according to the method depicted in Scheme 1.

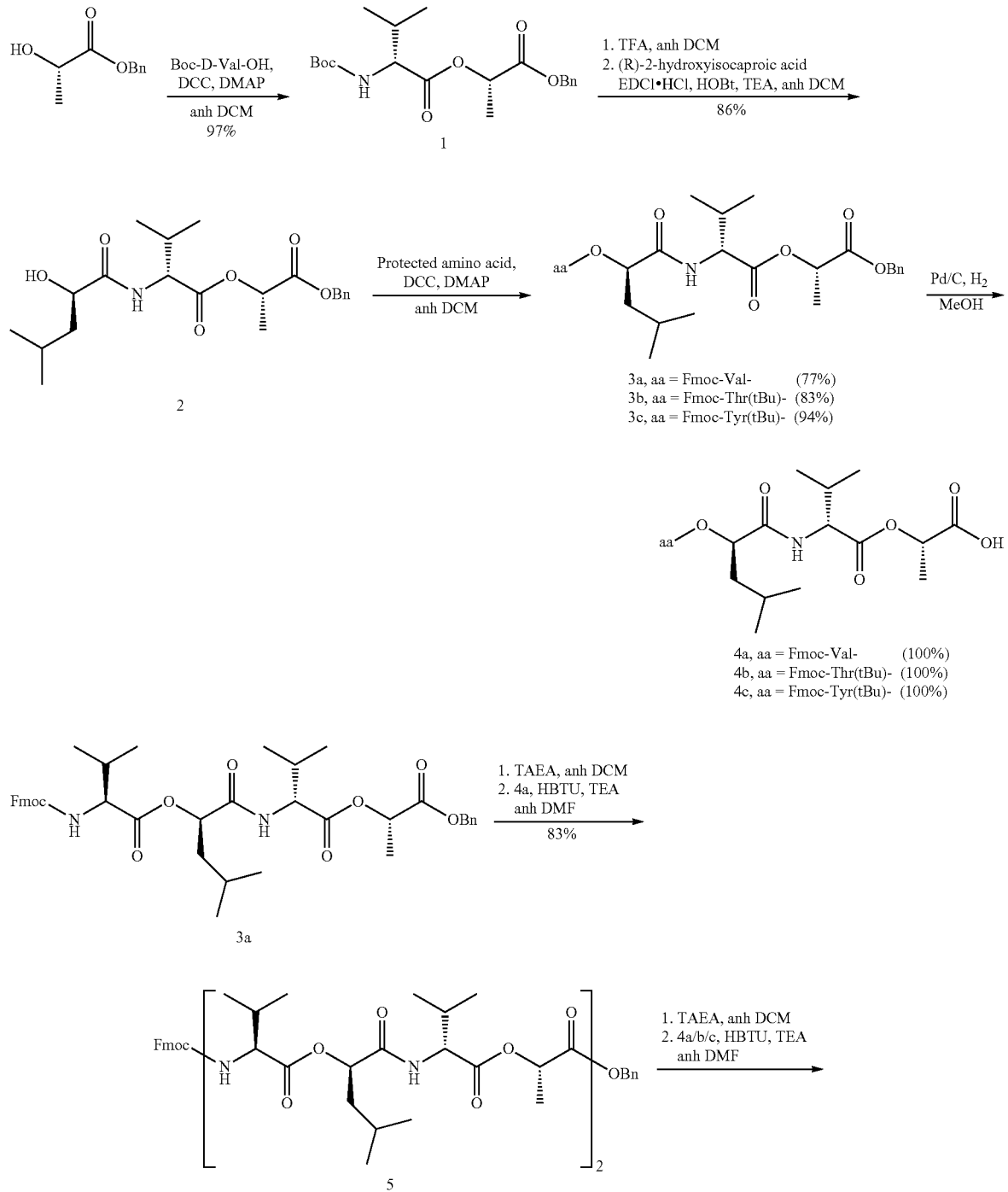

-continued
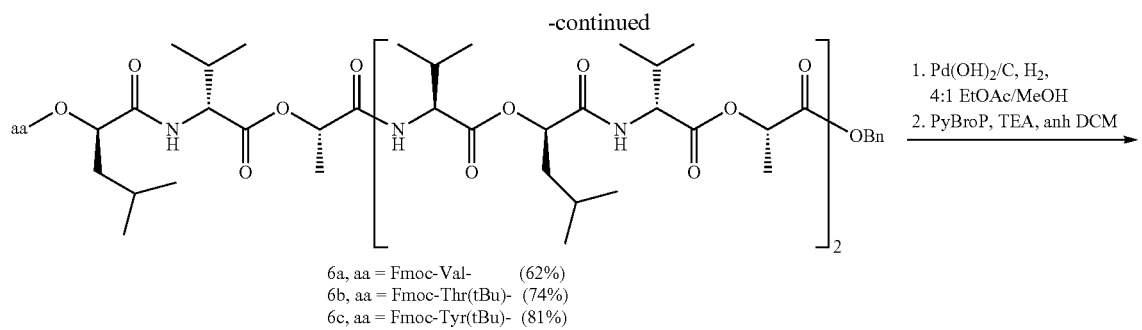
6a, aa = Fmoc-Val- (62%)
6b, aa = Fmoc-Thr(tBu)- (74%)
6c, aa = Fmoc-Tyr(tBu)- (81%)
1. Pd(OH)₂/C, H₂, 4:1 EtOAc/MeOH
2. PyBroP, TEA, anh DCM
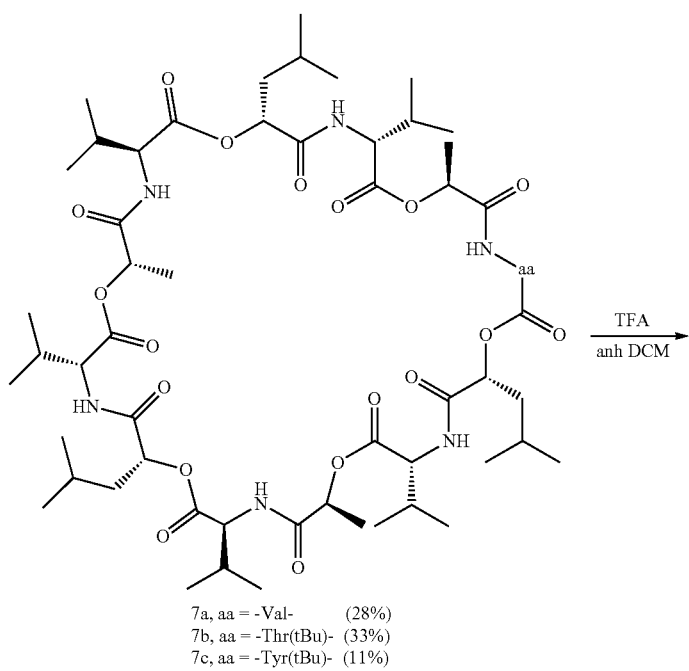
7a, aa = -Val- (28%)
7b, aa = -Thr(tBu)- (33%)
7c, aa = -Tyr(tBu)- (11%)
TFA
anh DCM
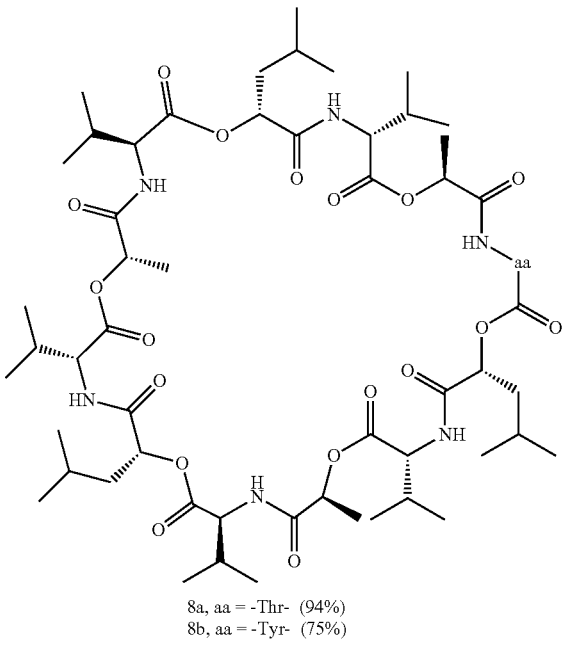
8a, aa = -Thr- (94%)
8b, aa = -Tyr- (75%)

Boc-D-Val-Lac-OBn (1): To a stirred solution containing Boc-D-Val (1.00 g, 4.60 mmol) and benzyl L-lactate (638 mg, 3.54 mmol) in 20 mL of anhydrous DCM at 0° C. was added DMAP (86 mg, 0.71 mmol) followed by DCC (840 mg, 4.07 mmol). The reaction mixture was stirred at 23° C. for 4 h. The mixture was filtered to remove most of the DCU and the filtrate was diluted with 80 mL of DCM. The organic solution was washed with 50 mL of 0.3 N HCl, 50 mL of satd aq $NaHCO_3$ and 50 mL of brine. The organic solution was dried over $MgSO_4$ and concentrated under reduced pressure. The residue was dissolved in 50 mL of cold acetonitrile and the formed precipitate was filtered. The filtrate was concentrated under reduced pressure to afford 1 as a colorless oil: yield 97% (1.32 g, 3.47 mmol); $[\alpha]^{24}_D$−3.43 (c 0.18, ethyl acetate); $^1H$ NMR ($CDCl_3$, 400 MHz) δ 7.25 (5H, m), 5.06 (4H, m), 4.22 (1H, m), 2.11 (1H, m), 1.42 (3H, d, J=7.2 Hz), 1.37 (9H, s), 0.90 (3H, d, J=6.8 Hz) and 0.83 (3H, d, J=6.8 Hz); $^{13}C$ NMR ($CDCl_3$, 101 MHz) δ 171.3, 169.9, 155.4, 135.1, 128.4, 128.5, 128.0, 79.5, 69.0, 66.9, 58.5, 31.0, 28.2, 18.8, 17.4 and 16.8; HRMS (APCI), m/z 380.2067 $[M+H]^+$ (calcd for $C_{20}H_{30}NO_6$, 380.2073).

D-Hica-D-Val-Lac-OBn (2): To a stirred solution containing ester 1 (4.12 g, 10.9 mmol) in 60 mL of anhydrous DCM was added TFA (15 mL). The reaction mixture was stirred at 23° C. for 5 h and then concentrated under reduced pressure. The residue was dissolved in 140 mL of DCM and washed with two 100-mL portions of satd aq $NaHCO_3$ and 100 mL of brine. The organic solution was dried over $MgSO_4$ and concentrated under reduced pressure. The residue was dissolved in 60 mL of anhydrous DCM and cooled to 0° C. Next, (R)-2-hydroxyisocaproic acid (1.44 g, 10.9 mmol) was added followed by HOBt (2.22 g, 16.4 mmol), TEA (2.27 mL, 1.66 g, 16.4 mmol) and EDCI hydrochloride (3.14 g, 16.4 mmol). The reaction mixture was stirred at 23° C. for 18 h. The solution was diluted with 140 mL of DCM and washed with 100 mL of 0.3 N HCl, 100 mL of satd aq $NaHCO_3$ and 100 mL of brine. The organic solution was dried over $MgSO_4$ and concentrated under reduced pressure. The residue was separated by chromatography on a silica gel column. Elution with 1:2 ethyl acetate/hexanes gave 2 as a colorless oil: yield 86% (3.68 g, 9.35 mmol); TLC $R_f$ 0.40 (1:2 ethyl acetate/hexanes); $[\alpha]^{24}_D$+12.8 (c 0.18, ethyl acetate); $^1H$ NMR ($CDCl_3$, 400 MHz) δ 7.33 (5H, m), 6.93 (1H, d, J=9.2 Hz), 5.14 (3H, m), 4.64 (1H, dd, J=9.2 Hz, 4.8 Hz), 4.14 (1H, m), 2.66 (1H, d, J=4.8 Hz), 2.21 (1H, m), 1.84 (1H, m), 1.65 (1H, m), 1.53 (4H, m) and 0.93 (12H, m); $^{13}C$ NMR ($CDCl_3$, 101 MHz) δ 174.4, 171.2, 170.2, 135.3, 128.8, 128.6, 128.3, 71.1, 69.5, 67.3, 56.7, 44.0, 31.4, 24.7, 23.6, 21.5, 19.1, 17.7 and 17.1; HRMS (APCI), m/z 394.2239 $[M+H]^+$ (calcd for $C_{21}H_{32}NO_6$, 394.2230).

Fmoc-Val-D-Hica-D-Val-Lac-OBn (3a): To a stirred solution containing compound 2 (3.58 g, 9.10 mmol), Fmoc-Val (3.70 g, 10.9 mmol) and DMAP (334 mg, 2.73 mmol) in 100 mL of anhydrous DCM at 0° C. was added DCC (2.06 g, 10.0 mmol). The reaction mixture was stirred at 23° C. for 2 h. The solution was filtered and the filtrate was concentrated under reduced pressure. The crude product was separated by chromatography on a silica gel column. Elution with 1:4 ethyl acetate/hexanes gave 3a as a colorless solid: yield 77% (5.0 g, 6.98 mmol); TLC $R_f$ 0.40 (1:4 ethyl acetate/hexanes); mp 43-47° C.; $[\alpha]^{24}_D$+6.59 (c 0.43, ethyl acetate); $^1H$ NMR ($CDCl_3$, 400 MHz) δ 7.74 (2H, d, J=7.2 Hz), 7.58 (2H, d, J=7.6 Hz), 7.39 (2H, m), 7.33 (7H, m), 6.76 (1H, d, J=8.4 Hz), 5.39 (1H, d, J=8.8 Hz), 5.24 (1H, m), 5.09 (3H, m), 4.55 (1H, m), 4.41 (1H, m), 4.25 (3H, m), 2.28 (1H, m), 2.15 (1H, m), 1.74 (3H, m), 1.42 (3H, d, J=6.8 Hz) and 0.95 (18H, m); $^{13}C$ NMR ($CDCl_3$, 101 MHz) δ 171.6, 170.6, 170.1, 170.0, 156.5, 144.0, 143.8, 141.4, 135.3, 128.6, 128.4, 128.2, 127.8, 127.1, 125.2, 120.1, 120.0, 73.6, 69.3, 67.4, 67.1, 59.8, 57.4, 47.2, 40.8, 30.8, 30.7, 24.5, 23.3, 21.5, 19.2, 19.1, 18.0 and 16.8; HRMS (APCI), m/z 715.3586 $[M+H]^+$ (calcd for $C_{41}H_{51}N_2O_9$, 715.3594).

Fmoc-Thr(tBu)-D-Hica-D-Val-Lac-OBn (3b): Using the strategy followed for the preparation and purification of 3a, unit 2 (492 mg, 1.25 mmol) was coupled to Fmoc-Thr(tBu) (596 mg, 1.50 mmol) using DMAP (46 mg, 0.38 mmol) and DCC (285 mg, 1.38 mmol) in 15 mL of anhydrous DCM. After separation by column chromatography 3b was obtained as a colorless solid. Yield 83% (800 mg, 1.04 mmol); TLC $R_f$ 0.40 (1:3 ethyl acetate/hexanes); mp 40-44° C.; $[\alpha]^{24}_D$+10.8 (c 0.42, ethyl acetate); $^1H$ NMR ($CDCl_3$, 400 MHz) δ 7.74 (2H, d, J=7.6 Hz), 7.58 (2H, t, J=7.2 Hz), 7.38 (2H, t, J=7.6 Hz), 7.29 (7H, m), 6.77 (1H, d, J=8.4 Hz), 5.69 (1H, d, J=8.4 Hz), 5.18 (1H, m), 5.09 (3H, m), 4.55 (1H, dd, J=8.8 Hz, 5.6 Hz), 4.35 (3H, m), 4.21 (2H, m), 2.27 (1H, m), 1.79 (3H, m), 1.45 (3H, d, J=6.8 Hz), 1.23 (3H, d, J=6.4 Hz), 1.18 (9H, s) and 0.95 (12H, m); $^{13}C$ NMR ($CDCl_3$, 101 MHz) δ 170.51, 170.50, 169.99, 169.72, 156.57, 144.03, 143.75, 141.32, 135.22, 128.60, 128.43, 128.18, 127.75, 127.10, 125.23, 120.01, 74.44, 73.87, 69.28, 67.42, 67.13, 67.07, 60.06, 57.23, 47.16, 40.89, 30.95, 28.55, 24.32, 23.08, 21.92, 20.53, 18.99, 17.93 and 16.85; HRMS (APCI), m/z 773.4015 $[M+H]^+$ (calcd for $C_{44}H_{57}N_2O_{10}$, 773.4013).

Fmoc-Tyr(tBu)-D-Hica-D-Val-Lac-OBn (3c): Using the procedure followed for the preparation and purification of 3a, unit 2 (492 mg, 1.25 mmol) was coupled to Fmoc-Tyr(tBu) (584 mg, 1.27 mmol) using DMAP (39 mg, 0.32 mmol) and DCC (241 mg, 1.17 mmol) in 15 mL of anhydrous DCM. After separation by column chromatography 3c was obtained as a colorless solid. Yield 94% (830 mg, 0.99 mmol); TLC $R_f$ 0.40 (1:3 ethyl acetate/hexanes); mp 45-50° C.; $[\alpha]^{24}_D$+6.04 (c 0.27, ethyl acetate); $^1H$ NMR ($CDCl_3$, 400 MHz) δ 7.74 (2H, d, J=7.6 Hz), 7.55 (2H, m), 7.38 (2H, t, J=7.6 Hz), 7.26 (7H, m), 7.08 (2H, d, J=8.4 Hz), 6.95 (1H, d, J=8.8 Hz), 6.90 (2H, d, J=8.4 Hz), 5.55 (1H, d, J=7.2 Hz), 5.22 (1H, m), 5.07 (3H, m), 4.55 (2H, m), 4.35 (1H, m), 4.28 (1H, m), 4.15 (1H, t, J=7.2 Hz), 3.13 (1H, m), 3.04 (1H, m), 2.31 (1H, m), 1.71 (2H, m), 1.50 (1H, m), 1.45 (3H, d, J=7.2 Hz), 1.31 (9H, s), 0.97 (6H, m) and 0.87 (6H, m); $^{13}C$ NMR ($CDCl_3$, 101 MHz) δ 171.19, 170.51, 170.11, 170.06, 156.01, 154.68, 143.81, 143.67, 141.26, 135.18, 130.17, 129.66, 128.54, 128.36, 128.11, 127.74, 127.05, 125.07, 124.12, 119.97, 78.34, 73.66, 69.16, 67.31, 67.01, 57.40, 55.67, 47.01, 40.70, 36.93, 30.58, 28.84, 24.37, 23.14, 21.55, 19.05, 18.10 and 16.79; HRMS (APCI), m/z 835.4176 $[M+H]^+$ (calcd for $C_{49}H_{59}N_2O_{10}$, 835.4169).

Fmoc-[Val-D-Hica-D-Val-Lac]$_2$-OBn (5): To a stirred solution containing compound 3a (300 mg, 0.42 mmol) in 10 mL of anhydrous DCM was added 2,2',2"-triaminotriethylamine (633 μL, 614 mg, 4.20 mmol). The reaction mixture was stirred at 23° C. for 2 h. The solution was diluted with 10 mL of DCM and washed with two 10-mL portions of phosphate buffer (25.3 g of $K_2HPO_4$/12.3 g of $KH_2PO_4$ in 250 mL of water) and 10 mL of brine. The organic solution was dried over $MgSO_4$ and concentrated under reduced pressure. The residue was dissolved in 5 mL of anhydrous DMF and unit 4a (262 mg, 0.42 mmol) was added followed by TEA (58 μL, 42 mg, 0.42 mmol) and HBTU (319 mg, 0.84 mmol). The solution was stirred at 23° C. for 16 h and then diluted with 50 mL of ethyl acetate and washed with 50 mL of brine. The organic solution was dried over $MgSO_4$ and concentrated under reduced pressure. The mixture was separated by chromatography on a silica gel column. Elution with 1:4 ethyl acetate/hexanes gave 5 as a colorless solid: yield 83% (384 mg, 0.35 mmol); TLC $R_f$ 0.20 (1:4 ethyl acetate/hexanes); mp 59-64° C.; $[\alpha]^{24}_D$+6.27 (c 0.26, ethyl acetate); $^1$H NMR (CDCl$_3$, 400 MHz) δ 7.74 (2H, d, J=7.2 Hz), 7.58 (2H, dd, J=13.2 Hz, 7.6 Hz), 7.39 (3H, m), 7.33 (7H, m), 7.20 (1H, d, J=7.2 Hz), 7.16 (1H, d, J=8.8 Hz), 5.51 (1H, d, J=7.6 Hz), 5.27 (2H, m), 5.23 (1H, m), 5.09 (3H, m), 4.42 (2H, m), 4.33 (1H, m), 4.20 (2H, m), 4.11 (1H, t, J=7.6 Hz), 4.04 (1H, t, J=7.6 Hz), 2.27 (3H, m), 2.15 (1H, m), 1.74 (6H, m), 1.41 (6H, d, J=6.4 Hz) and 0.95 (36H, m); $^{13}$C NMR (CDCl$_3$, 101 MHz) δ 171.99, 171.04, 170.91, 170.85, 170.52, 170.41, 170.28, 170.21, 156.89, 143.87, 143.62, 141.28, 135.29, 128.48, 128.24, 128.12, 127.72, 127.02, 125.02, 119.97, 73.15, 73.07, 70.43, 69.12, 67.46, 66.92, 60.40, 59.02, 57.80, 47.03, 40.68, 40.44, 34.64, 31.56, 30.38, 30.08, 29.72, 29.42, 25.25, 24.41, 23.19, 22.62, 21.42, 21.37, 19.17, 19.06, 19.01, 18.89, 18.79, 18.55, 18.32, 17.42 and 16.75; HRMS (APCI), m/z 1099.586 [M+H]$^+$ (calcd for C$_{60}$H$_{82}$N$_4$O$_{15}$, 1099.585).

Fmoc-[Val-D-Hica-D-Val-Lac]$_3$-OBn (6a): By means of the strategy followed for the preparation and purification of 5, unit 5 (345 mg, 0.31 mmol) was deprotected with 2,2',2"-triaminotriethylamine (467 μL, 453 mg, 3.10 mmol) in 10 mL of DCM and then coupled to unit 4a (194 mg, 0.31 mmol) using HBTU (235 mg, 0.62 mmol) and TEA (43 μL, 31 mg, 0.42 mmol) in 5 mL of anhydrous DMF. After separation by column chromatography 6a was obtained as a colorless solid. Yield 62% (284 mg, 0.19 mmol); TLC $R_f$ 0.35 (1:2 ethyl acetate/hexanes); mp 59-63° C.; $[\alpha]^{24}_D$+3.56 (c 0.23, ethanol); $^1$H NMR (CDCl$_3$, 400 MHz) δ 7.74 (2H, d, J=7.6 Hz), 7.66 (2H, m), 7.58 (2H, dd, J=14.8 Hz, 7.2 Hz), 7.51 (1H, d, J=6.0 Hz), 7.39 (3H, m), 7.33 (8H, m), 5.74 (1H, d, J=7.2 Hz), 5.34 (1H, m), 5.20 (4H, m), 5.10 (3H, m), 4.38 (3H, m), 4.22 (1H, t, J=7.2 Hz), 4.13 (2H, m), 4.04 (1H, t, J=6.4 Hz), 3.95 (2H, m), 2.27 (5H, m), 1.99 (1H, m), 1.74 (9H, m), 1.41 (9H, d, J=6.8 Hz) and 0.95 (54H, m); $^{13}$C NMR (CDCl$_3$, 101 MHz) δ 172.54, 171.69, 171.55, 171.40, 170.96, 170.70, 170.68, 170.59, 170.58, 170.41, 170.38, 170.36, 157.20, 144.16, 143.78, 141.44, 135.49, 128.60, 128.35, 127.85, 127.19, 125.25, 120.10, 73.35, 73.10, 72.68, 70.54, 70.17, 69.21, 67.64, 67.04, 60.77, 60.04, 59.82, 59.66, 59.08, 58.16, 47.19, 40.94, 40.59, 40.51, 34.79, 31.71, 30.42, 30.08, 29.77, 29.47, 29.29, 29.18, 25.40, 24.57, 24.53, 24.50, 23.38, 23.35, 22.77, 21.68, 21.49, 21.40, 19.48, 19.35, 19.30, 19.26, 19.19, 19.16, 19.06, 18.88, 18.64, 17.56, 17.35 and 16.91; HRFTMS (ESI), m/z 1505.788 [M+Na]$^+$ (calcd for C$_{79}$H$_{114}$N$_6$O$_{21}$Na, 1505.793).

Fmoc-Thr(tBu)-D-Hica-D-Val-Lac-[Val-D-Hica-D-Val-Lac]$_2$-OBn (6b): With the procedure followed for the preparation and purification of 5, unit 5 (300 mg, 0.27 mmol) was deprotected with 2,2',2"-triaminotriethylamine (407 μL, 395 mg, 2.70 mmol) in 12 mL of DCM and then coupled to unit 4b (184 mg, 0.27 mmol) using HBTU (205 mg, 0.54 mmol) and TEA (37 μL, 27 mg, 0.27 mmol) in 5 mL of anhydrous DMF. After separation by column chromatography 6b was obtained as a colorless solid. Yield 74% (308 mg, 0.20 mmol); TLC $R_f$ 0.35 (1:2 ethyl acetate/hexanes); mp 62-65° C.; $[\alpha]^{24}_D$+13.0 (c 0.10, ethanol); $^1$H NMR (CDCl$_3$, 400 MHz) δ 7.73 (2H, d, J=7.6 Hz), 7.70 (1H, d, J=6.0 Hz), 7.56 (4H, m), 7.51 (2H, t, J=7.6 Hz), 7.33 (8H, m), 7.17 (1H, d, J=6.4 Hz), 5.68 (1H, d, J=7.2 Hz), 5.23 (5H, m), 5.10 (3H, m), 4.35 (3H, m), 4.22 (1H, t, J=7.2 Hz), 4.04 (6H, m), 2.27 (5H, m), 1.74 (9H, m), 1.41 (9H, m), 1.22 (3H, d, J=5.6 Hz), 1.18 (9H, s) and 0.95 (48H, m); $^{13}$C NMR (CDCl$_3$, 101 MHz) δ 171.34, 171.27, 171.25, 170.89, 170.83, 170.63, 170.59, 170.45, 170.44, 170.29, 170.27, 156.80, 143.84, 143.58, 141.25, 135.35, 128.46, 128.21, 128.14, 127.72, 127.04, 125.05, 119.98, 74.62, 73.22, 72.99, 72.54, 70.19, 70.08, 69.07, 67.50, 66.88, 66.83, 60.19, 59.91, 59.80, 59.46, 59.26, 58.05, 47.03, 40.79, 40.33, 34.62, 30.23, 29.65, 29.57, 29.33, 28.51, 28.46, 25.23, 24.36, 24.33, 24.21, 23.22, 23.02, 21.71, 21.40, 21.33, 20.54, 19.34, 19.22, 19.19, 19.15, 19.11, 19.09, 19.04, 18.97, 18.93, 18.52, 17.25, 17.12 and 16.74; HRFTMS (ESI), m/z 1563.833 [M+Na]$^+$ (calcd for C$_{82}$H$_{120}$N$_6$O$_{22}$Na, 1563.835).

Fmoc-Tyr(tBu)-D-Hica-D-Val-Lac-[Val-D-Hica-D-Val-Lac]$_2$-OBn (6c): Employing the strategy followed for the preparation and purification of 5, unit 5 (630 mg, 0.57 mmol) was deprotected with 2,2',2"-triaminotriethylamine (850 μL, 834 mg, 5.70 mmol) in 20 mL of DCM and then coupled to unit 4c (425 mg, 0.57 mmol) using HBTU (434 mg, 1.14 mmol) and TEA (79 μL, 58 mg, 0.57 mmol) in 5 mL of anhydrous DMF. After separation by column chromatography 6c was obtained as a colorless solid. Yield 81% (744 mg, 0.46 mmol); TLC $R_f$ 0.35 (1:2 ethyl acetate/hexanes); mp 62-65° C.; $[\alpha]^{24}_D$+5.71 (c 0.28, ethanol); $^1$H NMR (CDCl$_3$, 400 MHz) δ 7.78 (1H, d, J=7.6 Hz), 7.74 (2H, d, J=7.6 Hz), 7.67 (1H, m), 7.62 (1H, d, J=6.4 Hz), 7.52 (2H, m), 7.44 (1H, m), 7.37 (3H, m), 7.30 (7H, m), 7.06 (2H, d, J=8.0 Hz), 6.89 (2H, d, J=8.4 Hz), 5.73 (1H, d, J=6.4 Hz), 5.18 (8H, m), 4.35 (4H, m), 4.19 (1H, t, J=6.8 Hz), 4.06 (3H, m), 3.95 (1H, t, J=6.4 Hz), 3.03 (2H, m), 2.25 (5H, m), 1.74 (8H, m), 1.59 (1H, m), 1.41 (9H, m), 1.30 (9H, s) and 0.95 (48H, m); $^{13}$C NMR (CDCl$_3$, 101 MHz) δ 171.92, 171.59, 171.45, 171.42, 171.21, 170.97, 170.88, 170.72, 170.64, 170.53, 170.44, 170.43, 156.72, 154.89, 144.01, 143.74, 141.36, 135.51, 130.70, 129.76, 128.61, 128.35, 128.31, 127.89, 127.17, 125.21, 124.24, 120.13, 80.72, 73.45, 73.14, 72.74, 70.46, 70.28, 69.26, 67.68, 67.05, 59.95, 59.92, 59.70, 59.24, 58.24, 56.19, 47.14, 40.93, 40.52, 36.61, 36.59, 30.40, 29.83, 29.79, 29.55, 29.47, 29.38, 29.26, 29.19, 28.99, 24.53, 24.51, 24.34, 23.39, 23.23, 21.65, 21.49, 19.46, 19.43, 19.31, 19.30, 19.27, 19.21, 19.12, 19.09, 18.68, 17.49, 17.44 and 16.91; HRFTMS (ESI), m/z 1625.844 [M+Na]$^+$ (calcd for C$_{87}$H$_{122}$N$_6$O$_{22}$Na, 1625.850).

Cyclo-[Val-D-Hica-D-Val-Lac]$_3$ (7a, Silstatin 1): To a stirred solution containing depsipeptide 6a (250 mg, 0.17 mmol) in 5 mL of 4:1 ethyl acetate/methanol was added 20% palladium hydroxide-on-carbon (125 mg). The mixture was stirred under a hydrogen atmosphere (1 atm) at 23° C. for 7 h and then filtered through Celite. The filtrate was concentrated under reduced pressure and the residue was dissolved in 125 mL of anhydrous DCM. TEA (24 μL, 17 mg, 0.17 mmol) was added followed by PyBroP (238 mg, 0.51 mmol) and the reaction mixture was stirred at 23° C. for 24 h. The solution was filtered through a silica gel plug and the filtrated was concentrated under reduced pressure. The residue was separated by chromatography on a silica gel column. Elution with 1:4 ethyl acetate/hexanes gave 7a (silstatin 1) as a colorless solid: yield 28% (54 mg, 47 μmol); TLC $R_f$ 0.42 (1:4 ethyl acetate/hexanes); mp 137-138° C.; $[\alpha]^{24}_D$+30.9 (c 0.11, ethanol); $^1$H NMR (CDCl$_3$, 400 MHz) δ 7.78 (3H, d, J=7.6 Hz), 7.73 (3H, d, J=6.4 Hz), 5.21 (3H, m), 5.13 (3H, m), 4.06 (3H, dd, J=9.6 Hz, 8.0 Hz), 3.93 (3H, dd, J=9.6 Hz, 6.4 Hz), 2.23 (6H, m), 1.74 (9H, m), 1.44 (9H, d, J=7.2 Hz), 1.04 (18H, m) and 0.95 (36H, m); $^{13}$C NMR (CDCl$_3$, 101 MHz) δ 172.4, 172.0, 171.6, 170.4, 73.5, 70.6, 60.3, 59.1, 40.8, 28.7, 28.5, 24.6, 23.4, 21.4, 19.8, 19.6, 19.3, 19.2 and 17.2; HRMS (APCI), m/z 1153.685 [M+H]$^+$ (calcd for C$_{57}$H$_{97}$N$_6$O$_{18}$, 1153.686).

Cyclo-{Thr(tBu)-D-Hica-D-Val-Lac-[Val-D-Hica-D-Val-Lac]$_2$} (7b): By the method followed for the preparation and purification of 7a, depsipeptide 6b (300 mg, 0.20 mmol) was deprotected using 20% palladium hydroxide-on-carbon (300 mg) in 10 mL of 4:1 ethyl acetate/methanol and then cyclized with PyBroP (373 mg, 0.80 mmol) and TEA (111 µL, 81 mg, 0.80 mmol) in 200 mL of anhydrous DCM. After separation by column chromatography 7b was obtained as a colorless solid. Yield 33% (81 mg, 67 µmol); TLC $R_f$ 0.5 (1:3 ethyl acetate/hexanes); mp 75-78° C.; $[\alpha]^{24}_D$+23.3 (c 0.06, ethanol); $^1$H NMR (CDCl$_3$, 400 MHz) δ 7.83 (1H, d, J=8.0 Hz), 7.74 (1H, d, J=7.2 Hz), 7.66 (1H, d, J=8.4 Hz), 7.49 (1H, d, J=8.0 Hz), 7.45 (1H, d, J=5.6 Hz), 7.37 (1H, d, J=4.8 Hz), 5.20 (6H, m), 4.29 (1H, t, J=8.4 Hz), 4.17 (2H, m), 4.05 (3H, m), 3.85 (1H, dd, J=10 Hz, 6.0 Hz), 2.23 (5H, m), 1.74 (9H, m), 1.41 (9H, m), 1.20 (9H, s), 1.17 (3H, d, J=6.4 Hz), 1.10 (18H, m) and 0.90 (30H, m); $^{13}$C NMR (CDCl$_3$, 101 MHz) δ 172.33, 172.32, 172.14, 172.12, 171.81, 171.80, 171.13, 171.12, 170.35, 170.27, 170.19, 169.88, 74.76, 73.88, 73.37, 73.11, 70.91, 70.84, 70.64, 66.54, 60.82, 59.81, 59.12, 59.08, 58.53, 57.72, 40.96, 40.77, 40.71, 34.77, 29.64, 29.23, 28.78, 28.54, 28.53, 28.46, 25.38, 24.58, 24.55, 23.51, 23.50, 23.45, 21.47, 21.32, 21.20, 19.92, 19.86, 19.54, 19.53, 19.41, 19.38, 19.32, 19.04, 18.72, 18.45, 17.54, 17.13 and 17.05; HRMS (APCI), m/z 1211.723 [M+H]$^+$ (calcd for $C_{60}H_{103}N_6O_{19}$, 1211.728).

Cyclo-{Tyr(tBu)-D-Hica-D-Val-Lac-[Val-D-Hica-D-Val-Lac]$_2$} (7c): Using the strategy followed for the preparation and purification of 7a, depsipeptide 6c (700 mg, 0.44 mmol) was deprotected using 20% palladium hydroxide-on-carbon (300 mg) in 10 mL of 4:1 ethyl acetate/methanol and then cyclized with PyBroP (373 mg, 0.80 mmol) and TEA (111 µL, 81 mg, 0.80 mmol) in 200 mL of anhydrous DCM. After separation by column chromatography 7c was obtained as a colorless solid. Yield 11% (66 mg, 52 µmol); TLC $R_f$ 0.20 (1:4 ethyl acetate/hexanes); mp 64-67° C.; $[\alpha]^{24}_D$+25.7 (c 0.14, ethanol); $^1$H NMR (CDCl$_3$, 400 MHz) δ 7.94 (1H, d, J=7.2 Hz), 7.85 (2H, m), 7.76 (1H, d, J=8.0 Hz), 7.68 (1H, d, J=7.2 Hz), 7.65 (1H, d, J=6.0 Hz), 7.09 (2H, d, J=8.8 Hz), 6.86 (2H, d, J=8.4 Hz), 5.20 (4H, m), 5.05 (2H, m), 4.53 (q, J=7.6 Hz, 1H), 4.13 (1H, t, J=8.8 Hz), 4.02 (1H, dd, J=9.6 Hz, 7.6 Hz), 3.95 (1H, dd, J=9.6 Hz, 7.2 Hz), 3.89 (2H, dd, J=10 Hz, 6.0 Hz), 3.10 (2H, m), 2.23 (5H, m), 1.74 (7H, m), 1.55 (2H, t, J=6.8 Hz), 1.42 (6H, d, J=6.8 Hz), 1.36 (3H, d, J=6.8 Hz), 1.30 (9H, s), 1.05 (18H, m), 0.92 (24H, m), 0.75 (3H, d, J=6.8 Hz) and 0.71 (3H, d, J=6.4 Hz); $^{13}$C NMR (CDCl$_3$, 101 MHz) δ 172.49, 172.37, 172.10, 172.00, 171.71, 171.69, 171.53, 171.43, 170.59, 170.52, 170.27, 170.03, 154.31, 131.01, 129.66, 123.91, 78.11, 73.61, 73.18, 70.71, 70.50, 70.07, 60.41, 60.37, 59.39, 59.28, 58.39, 54.57, 40.73, 40.63, 40.61, 40.48, 35.27, 30.32, 29.65, 28.80, 28.58, 28.53, 28.46, 28.40, 24.45, 24.16, 23.71, 23.31, 22.88, 21.80, 21.24, 21.08, 19.73, 19.46, 19.35, 19.33, 19.17, 19.14, 19.11, 19.06, 19.04, 18.84, 17.19, 17.09 and 16.81; HRMS (APCI), m/z 1273.744 [M+H]$^+$ (calcd for $C_{65}H_{105}N_6O_{19}$, 1273.743).

Cyclo-{Thr-D-Hica-D-Val-Lac-[Val-D-Hica-D-Val-Lac]$_2$} (8a, Silstatin 2): To a stirred solution containing cyclodepsipeptide 7b (70 mg, 58 µmol) in 1 mL of anhydrous DCM was added TFA (250 µL). The reaction mixture was stirred at 23° C. for 2 h. The solution was concentrated under reduced pressure and the residue was separated by chromatography on a silica gel column. Elution with 1:3 ethyl acetate/hexanes gave 8a (silstatin 2) as a colorless solid: yield 94% (63 mg, 55 µmol); TLC $R_f$ 0.25 (1:3 ethyl acetate/hexanes); mp 75-78° C.; $[\alpha]^{24}_D$+25.9 (c 0.19, ethanol); $^1$H NMR (CDCl$_3$, 400 MHz) δ 7.99 (1H, d, J=7.2 Hz), 7.91 (1H, d, J=7.2 Hz), 7.81 (3H, m), 7.57 (1H, d, J=6.4 Hz), 5.28 (2H, m), 5.17 (3H, m), 5.05 (1H, m), 4.87 (1H, br s), 4.14 (1H, t, J=9.2 Hz), 3.95 (6H, m), 2.23 (4H, m), 2.12 (1H, m), 1.74 (9H, m), 1.41 (9H, m), 1.20 (3H, d, J=5.6 Hz), 1.10 (18H, m) and 0.90 (30H, m); $^{13}$C NMR (CDCl$_3$, 101 MHz) δ 173.51, 172.82, 172.39, 172.32, 172.20, 171.92, 171.53, 171.20, 171.00, 170.92, 170.29, 169.97, 74.49, 73.29, 73.16, 70.76, 70.70, 70.42, 66.19, 60.84, 60.47, 60.14, 59.89, 59.60, 58.52, 40.84, 40.70, 40.62, 28.72, 28.67, 28.55, 28.49, 28.21, 24.67, 24.57, 23.49, 23.37, 23.35, 23.33, 21.53, 21.36, 21.35, 19.70, 19.60, 19.53, 19.48, 19.47, 19.46, 19.45, 19.41, 19.37, 19.35, 18.98, 17.53, 17.10 and 17.03; HRMS (APCI), m/z 1155.664 [M+H]$^+$ (calcd for $C_{56}H_{95}N_6O_{19}$, 1155.665).

Cyclo-{Tyr-D-Hica-D-Val-Lac-[Val-D-Hica-D-Val-Lac]$_2$} (8b, Silstatin 3): Using the strategy followed for the preparation and purification of 8a, cyclodepsipeptide 7c (7 mg, 5.5 µmol) was deprotected with TFA (250 µL) in 1 mL of anhydrous DCM. After separation by column chromatography 8b (silstatin 3) was obtained as a colorless solid. Yield 75% (5 mg, 4.1 µmol); TLC $R_f$ 0.25 (1:3 ethyl acetate/hexanes); mp 65-68° C.; $[\alpha]^{24}_D$+35.0 (c 0.10, ethyl acetate); $^1$H NMR (CDCl$_3$, 400 MHz) δ 7.77 (6H, m), 7.04 (2H, d, J=8.4 Hz), 6.73 (2H, d, J=8.4 Hz), 5.20 (5H, m), 4.96 (1H, t, J=6.0 Hz), 4.43 (1H, q, J=7.6 Hz), 4.10 (3H, m), 3.95 (2H, m), 3.10 (2H, m), 2.23 (5H, m), 1.65 (9H, m), 1.42 (6H, d, J=6.8 Hz), 1.36 (3H, d, J=7.2 Hz), 1.04 (18H, m), 0.92 (24H, m), 0.71 (3H, d, J=6.4 Hz) and 0.71 (3H, d, J=6.8 Hz); $^{13}$C NMR (CDCl$_3$, 101 MHz) δ 172.50, 172.38, 172.23, 172.04, 171.98, 171.94, 171.81, 171.53, 171.43, 170.36, 170.28, 170.20, 155.19, 130.57, 127.82, 115.78, 73.90, 73.58, 73.43, 70.73, 70.64, 60.57, 60.22, 59.01, 58.81, 58.80, 55.29, 40.94, 40.80, 40.68, 35.44, 29.85, 29.81, 29.08, 28.79, 28.73, 28.63, 24.68, 24.64, 24.28, 23.49, 23.20, 22.84, 21.66, 21.41, 21.31, 19.83, 19.71, 19.59, 19.55, 19.47, 19.38, 19.37, 19.12, 18.98, 18.83, 17.42, 17.18 and 17.04; HRMS (APCI), m/z 1217.681 [M+H]$^+$ (calcd for $C_{61}H_{97}N_6O_{19}$, 1217.681).

Compounds 14a, 15a and 15b were synthesized according to the method depicted in Scheme 2.

Scheme 2.

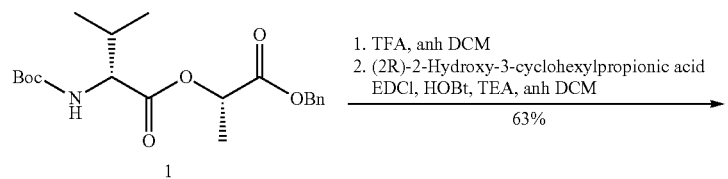

1. TFA, anh DCM
2. (2R)-2-Hydroxy-3-cyclohexylpropionic acid
   EDCI, HOBt, TEA, anh DCM
   63%

1

-continued
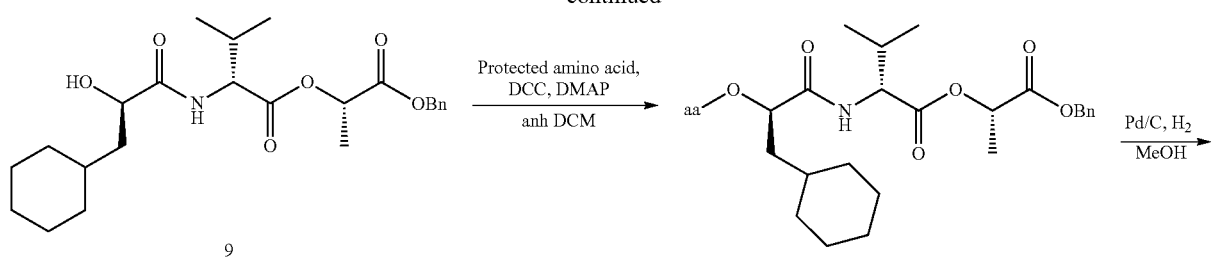
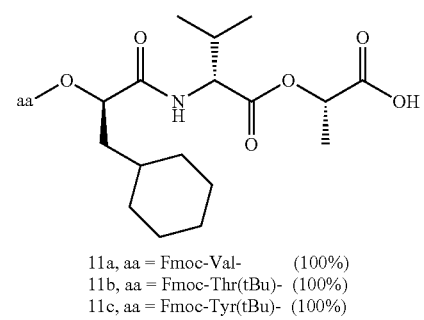
11a, aa = Fmoc-Val- (100%)
11b, aa = Fmoc-Thr(tBu)- (100%)
11c, aa = Fmoc-Tyr(tBu)- (100%)
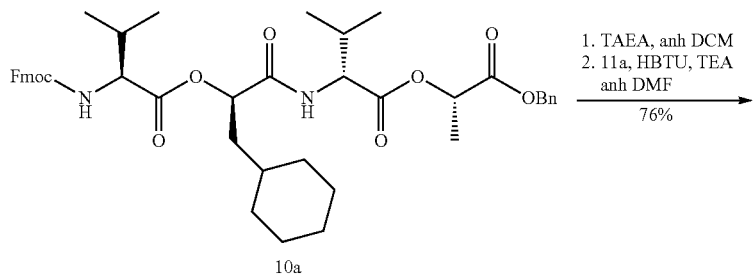
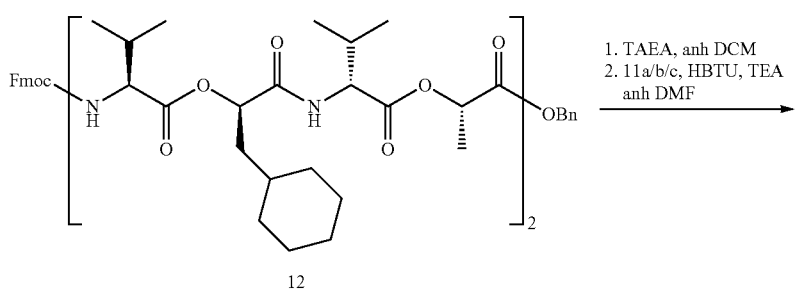
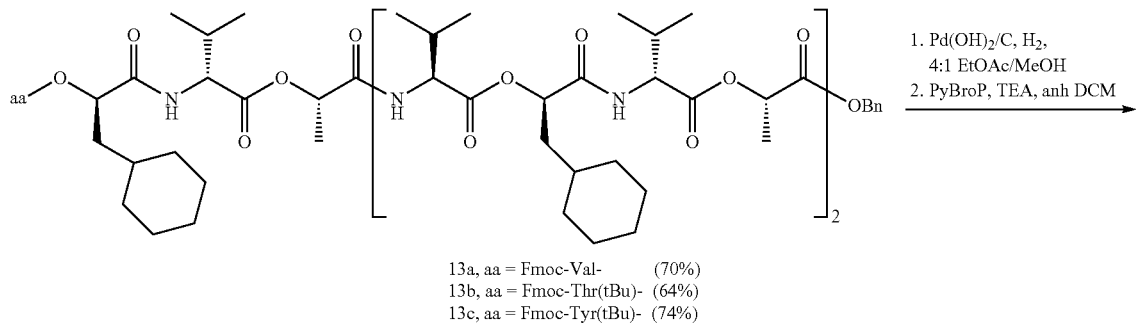
13a, aa = Fmoc-Val- (70%)
13b, aa = Fmoc-Thr(tBu)- (64%)
13c, aa = Fmoc-Tyr(tBu)- (74%)

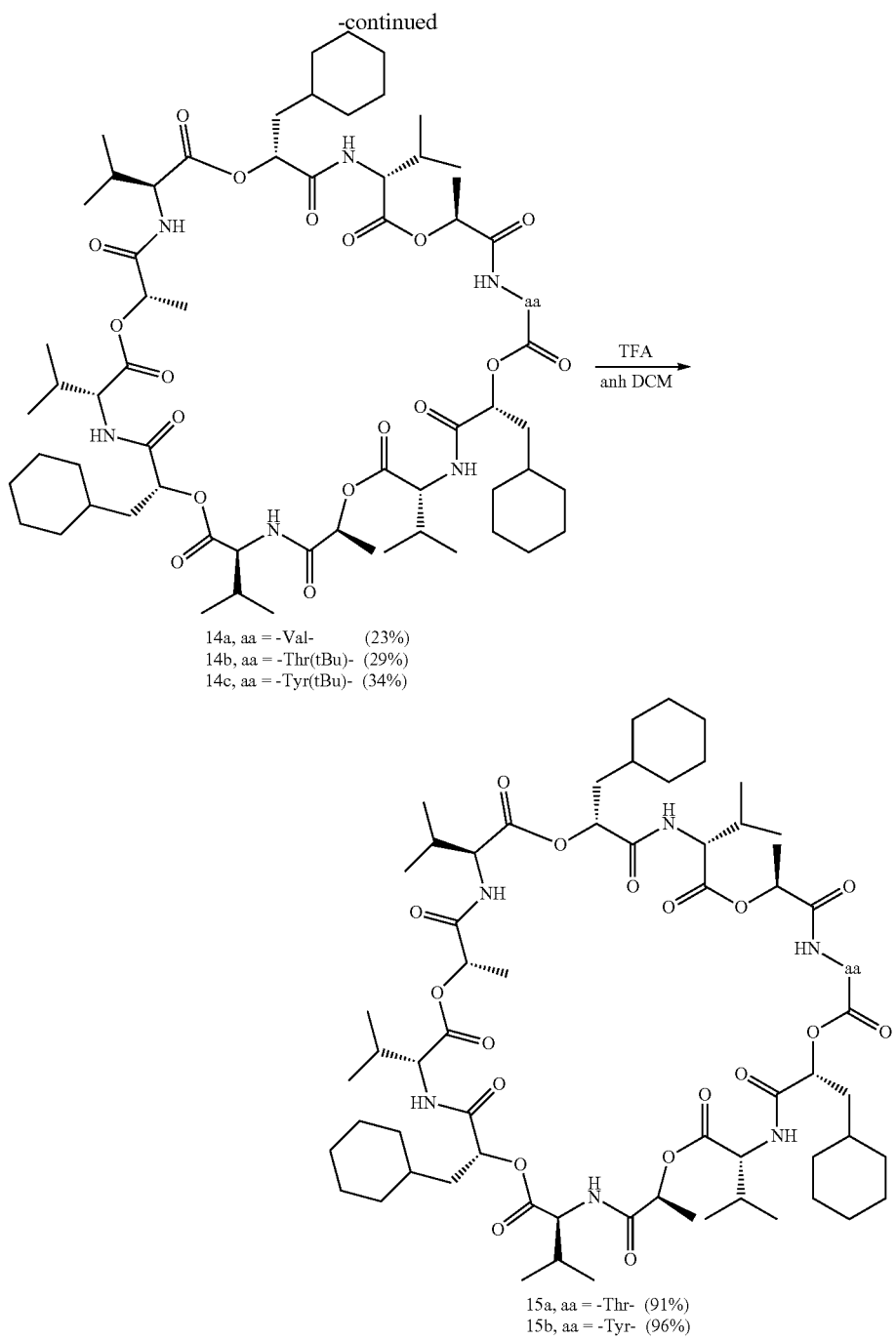

14a, aa = -Val- (23%)
14b, aa = -Thr(tBu)- (29%)
14c, aa = -Tyr(tBu)- (34%)

15a, aa = -Thr- (91%)
15b, aa = -Tyr- (96%)

D-Hcha-D-Val-Lac-OBn (9): Using the strategy followed for the preparation and purification of 2, unit 1 (2.52 g, 6.64 mmol) was deprotected with TFA (7.5 mL) in 30 mL of anhydrous DCM and then coupled to (2R)-2-hydroxy-3-cyclohexylpropionic acid (1.23 g, 7.14 mmol) using HOBt (1.35 g, 9.96 mmol), TEA (1.38 mL, 1.10 g, 9.96 mmol) and EDCI hydrochloride (1.91 g, 9.96 mmol) in 30 mL of anhydrous DCM. After separation by column chromatography 9 was obtained as a colorless oil (solidifies upon standing). Yield 63% (1.80 g, 4.15 mmol); TLC $R_f$ 0.30 (1:3 ethyl acetate/hexanes); mp 55-57° C.; $[\alpha]^{24}_D$+19.1 (c 0.32, ethanol); $^1$H NMR (CDCl$_3$, 400 MHz) δ 7.34 (5H, m), 6.90 (1H, d, J=9.2 Hz), 5.18 (2H, m), 4.64 (1H, dd, J=9.2 Hz, 4.8 Hz), 4.14 (1H, m), 2.62 (1H, br s), 2.21 (1H, m), 1.78 (1H, d, J=12.8 Hz), 1.66 (5H, m), 1.50 (5H, m), 1.20 (3H, m) and 0.93 (8H, m); $^{13}$C NMR (CDCl$_3$, 101 MHz) δ 174.5, 171.1, 170.1, 135.3, 128.8, 128.6, 128.3, 70.5, 69.5, 67.3, 56.7, 42.7, 34.3, 34.1, 32.3, 31.4, 26.6, 26.4, 26.2, 19.1, 17.7 and 17.1; HRMS (APCI), m/z 434.2542 [M+H]$^+$ (calcd for $C_{24}H_{36}NO_6$, 434.2543).

Fmoc-Val-D-Hcha-D-Val-Lac-OBn (10a): By the procedure followed for the preparation and purification of 3a, unit 9 (1.80 g, 4.15 mmol) was coupled to Fmoc-Val (1.55 g, 4.57 mmol) using DCC (943 mg, 4.57 mmol) and DMAP (152 mg, 1.25 mmol) in 50 mL of anhydrous DCM. After separation by column chromatography 10a was obtained as a colorless solid. Yield 82% (2.56 g, 3.39 mmol); TLC $R_f$ 0.25 (1:4 ethyl acetate/hexanes); mp 49-53° C.; $[\alpha]^{24}{}_D$+0.45 (c 0.22, chloroform); $^1$H NMR (CDCl$_3$, 400 MHz) δ 7.74 (2H, d, J=7.6 Hz), 7.57 (2H, d, J=7.6 Hz), 7.33 (7H, m), 6.74 (1H, d, J=8.8 Hz), 5.34 (1H, d, J=8.4 Hz), 5.28 (1H, m), 5.09 (3H, m), 4.55 (1H, m), 4.41 (1H, m), 4.25 (2H, m), 4.18 (1H, m), 2.28 (1H, m), 2.15 (1H, m), 1.74 (7H, m), 1.41 (4H, m), 1.16 (3H, m) and 0.95 (14H, m); $^{13}$C NMR (CDCl$_3$, 101 MHz) δ 171.63, 170.59, 170.13, 170.08, 156.50, 144.02, 143.81, 141.40, 135.29, 128.67, 128.49, 128.26, 127.84, 127.17, 125.20, 120.09, 73.02, 69.32, 67.44, 67.16, 59.84, 57.38, 47.21, 39.43, 33.94, 33.89, 32.16, 30.87, 30.82, 26.41, 26.34, 26.07, 19.22, 19.11, 18.09, 18.06 and 16.89; HRMS (APCI), m/z 755.3901 [M+H]$^+$ (calcd for C$_{44}$H$_{55}$N$_2$O$_9$, 755.3907).

Fmoc-Thr(tBu)-D-Hcha-D-Val-Lac-OBn (10b): With the method followed for the preparation and purification of 3a, unit 9 (1.80 g, 4.15 mmol) was coupled to Fmoc-Thr(OtBu) (381 mg, 0.96 mmol) using DCC (198 mg, 0.96 mmol) and DMAP (32 mg, 0.26 mmol) in 10 mL of anhydrous DCM. After separation by column chromatography 10b was obtained as a colorless solid. Yield 79% (561 mg, 0.69 mmol); TLC $R_f$ 0.27 (1:4 ethyl acetate/hexanes); mp 50-54° C.; $[\alpha]^{24}{}_D$+2.97 (c 0.37, chloroform); $^1$H NMR (CDCl$_3$, 400 MHz) δ 7.74 (2H, d, J=7.6 Hz), 7.57 (2H, t, J=7.6 Hz), 7.39 (2H, t, J=7.2 Hz), 7.33 (7H, m), 6.79 (1H, d, J=8.8 Hz), 5.70 (1H, d, J=8.0 Hz), 5.22 (1H, t, J=6.8 Hz), 5.09 (3H, m), 4.55 (1H, dd, J=8.4 Hz, 5.2 Hz), 4.35 (3H, m), 4.20 (3H, m), 2.28 (1H, m), 1.74 (7H, m), 1.41 (4H, m), 1.16 (15H, m) and 0.95 (8H, m); $^{13}$C NMR (CDCl$_3$, 101 MHz) δ 170.50, 170.48, 169.95, 169.78, 156.51, 143.99, 143.71, 141.28, 135.19, 128.56, 128.38, 128.13, 127.72, 127.06, 125.20, 119.97, 74.40, 73.37, 69.25, 67.39, 67.10, 67.02, 60.05, 57.21, 47.12, 39.43, 33.70, 33.49, 32.53, 30.91, 28.54, 26.33, 26.14, 25.96, 20.52, 18.94, 17.91 and 16.82; HRMS (APCI), m/z 813.4324 [M+H]$^+$ (calcd for C$_{47}$H$_{61}$N$_2$O$_{10}$, 813.4326).

Fmoc-Tyr(tBu)-D-Hcha-D-Val-Lac-OBn (10c): Using the strategy followed for the preparation and purification of 3a, unit 9 (376 mg, 0.87 mmol) was coupled to Fmoc-Tyr(OtBu) (441 mg, 0.96 mmol) using DCC (198 mg, 0.96 mmol) and DMAP (32 mg, 0.26 mmol) in 10 mL of anhydrous DCM. After separation by column chromatography 10b was obtained as a colorless solid. Yield 90% (688 mg, 0.79 mmol); TLC $R_f$ 0.25 (1:4 ethyl acetate/hexanes); mp 52-56° C.; $[\alpha]^{24}{}_D$+11.2 (c 0.17, chloroform); $^1$H NMR (CDCl$_3$, 400 MHz) δ 7.74 (2H, d, J=7.6 Hz), 7.57 (2H, t, J=7.6 Hz), 7.39 (2H, t, J=7.2 Hz), 7.33 (7H, m), 7.06 (2H, d, J=8.4 Hz), 6.90 (2H, d, J=8.4 Hz), 6.83 (1H, d, J=8.4 Hz), 5.45 (1H, d, J=7.6 Hz), 5.23 (1H, t, J=6.4 Hz), 5.09 (3H, m), 4.55 (2H, m), 4.35 (1H, m), 4.26 (1H, m), 4.15 (1H, m), 3.17 (1H, m), 3.02 (1H, m), 2.28 (1H, m), 1.74 (7H, m), 1.42 (4H, m), 1.31 (12H, m), 1.15 (3H, m) and 0.95 (8H, m); $^{13}$C NMR (CDCl$_3$, 101 MHz) δ 171.1, 170.6, 170.2, 170.1, 156.0, 154.7, 143.7, 141.3, 135.2, 130.3, 129.7, 128.6, 128.4, 128.2, 127.8, 127.1, 125.1, 124.2, 120.0, 78.5, 73.3, 69.3, 67.3, 67.1, 57.3, 55.5, 47.1, 39.4, 36.9, 33.8, 33.7, 32.4, 30.8, 28.9, 26.4, 26.1, 26.0, 19.1, 18.0 and 16.9; HRMS (APCI), m/z 875.4487 [M+H]$^+$ (calcd for C$_{52}$H$_{63}$N$_2$O$_{10}$, 875.4482).

Fmoc-[Val-D-Hcha-D-Val-Lac]$_2$-OBn (12): Application of the experimental strategy followed for the preparation and purification of 5, unit 10a (300 mg, 0.40 mmol) was deprotected with 2,2',2''-triaminotriethylamine (605 µL, 588 mg, 4.00 mmol) in 10 mL of DCM and then coupled to unit 11a (266 mg, 0.40 mmol) using HBTU (303 mg, 0.80 mmol) and TEA (55 µL, 40 mg, 0.40 mmol) in 5 mL of anhydrous DMF. After separation by column chromatography 12 was obtained as a colorless solid. Yield 76% (360 mg, 0.31 mmol); TLC $R_f$ 0.28 (1:4 ethyl acetate/hexanes); mp 60-65° C.; $[\alpha]^{24}{}_D$+17.1 (c 0.25, chloroform); $^1$H NMR (CDCl$_3$, 400 MHz) δ 7.74 (2H, d, J=7.2 Hz), 7.58 (2H, dd, J=14 Hz, 7.6 Hz), 7.39 (3H, m) 7.33 (7H, m), 7.21 (1H, d, J=7.2 Hz), 7.16 (1H, d, J=8.4 Hz), 5.50 (1H, d, J=7.6 Hz), 5.26 (3H, m), 5.09 (3H, m), 4.42 (2H, m), 4.33 (1H, m), 4.22 (2H, m), 4.11 (1H, t, J=7.6 Hz), 4.02 (1H, t, J=7.6 Hz), 2.27 (3H, m), 2.15 (1H, m), 1.74 (14H, m), 1.41 (8H, m), 1.16 (6H, m) and 0.95 (28H, m); $^{13}$C NMR (CDCl$_3$, 101 MHz) δ 172.17, 171.33, 171.06, 171.01, 170.66, 170.54, 170.52, 170.35, 157.04, 144.01, 143.75, 141.41, 135.44, 128.60, 128.36, 128.25, 127.85, 127.19, 125.16, 120.10, 72.65, 72.58, 70.52, 69.24, 67.61, 67.04, 60.58, 59.18, 57.98, 47.16, 39.32, 39.13, 34.77, 33.94, 33.83, 33.81, 32.18, 32.11, 31.69, 30.49, 30.22, 29.85, 29.49, 26.47, 26.42, 26.39, 26.34, 26.10, 26.05, 25.39, 19.21, 19.16, 19.03, 18.94, 18.74, 18.47, 17.56 and 16.88; HRMS (APCI): m/z 1179.645 [M+H]$^+$ (calcd for C$_{66}$H$_{91}$N$_4$O$_{15}$, 1179.648).

Fmoc-[Val-D-Hcha-D-Val-Lac]$_3$-OBn (13a): Again using the procedure followed for the preparation and purification of 5, unit 12 (320 mg, 0.27 mmol) was deprotected with 2,2',2''-triaminotriethylamine (281 µL, 273 mg, 2.16 mmol) in 6 mL of DCM and then coupled to unit 11a (179 mg, 0.27 mmol) using HBTU (205 mg, 0.54 mmol) and TEA (37 µL, 27 mg, 0.27 mmol) in 5 mL of anhydrous DMF. After separation by column chromatography 13a was obtained as a colorless solid. Yield 70% (304 mg, 0.19 mmol); TLC $R_f$ 0.30 (1:4 ethyl acetate/hexanes); mp 60-64° C.; $[\alpha]^{24}{}_D$+20.9 (c 0.11, chloroform); $^1$H NMR (CDCl$_3$, 400 MHz) δ 7.73 (2H, d, J=7.2 Hz), 7.66 (7.6 Hz, 2H, J=4.4 Hz, 2H), 7.58 (3H, d, J=15.6 Hz), 7.51 (1H, d, J=6.0 Hz), 7.36 (3H, m), 7.29 (8H, m), 5.79 (1H, d, J=7.2 Hz), 5.24 (5H, m), 5.10 (3H, m), 4.38 (3H, m), 4.21 (1H, t, J=7.2 Hz), 4.13 (2H, m), 4.02 (1H, m), 3.93 (2H, m), 2.27 (5H, m), 1.99 (1H, m), 1.74 (21H, m), 1.41 (12H, m) and 1.02 (51H, m); $^{13}$C NMR (CDCl$_3$, 101 MHz) δ 172.44, 171.71, 171.39, 171.38, 171.29, 170.88, 170.68, 170.52, 170.46, 170.42, 170.26, 170.18, 157.07, 144.03, 143.63, 141.27, 135.35, 128.43, 128.17, 128.13, 127.69, 127.02, 124.99, 119.94, 72.57, 72.29, 71.86, 70.35, 69.94, 69.04, 67.49, 66.86, 60.67, 59.95, 59.66, 59.64, 58.92, 58.08, 47.03, 39.31, 38.96, 34.63, 33.85, 33.81, 33.69, 33.66, 33.61, 32.15, 32.03, 31.94, 31.86, 30.20, 29.92, 29.54, 29.26, 29.15, 29.02, 28.97, 26.33, 26.31, 26.26, 26.21, 25.95, 25.92, 25.24, 20.67, 19.35, 19.19, 19.15, 19.14, 19.11, 19.06, 19.02, 18.96, 18.91, 18.79, 18.54, 17.42, 17.15 and 16.74; HRFTMS (ESI), m/z 1625.885 [M+Na]$^+$ (calcd for C$_{88}$H$_{126}$N$_6$O$_{21}$Na, 1625.887).

Fmoc-Thr(tBu)-D-Hcha-D-Val-Lac-[Val-D-Hcha-D-Val-Lac]$_2$-OBn (13b): By the procedure followed for the preparation and purification of 5, unit 12 (500 mg, 0.42 mmol) was deprotected with 2,2',2''-triaminotriethylamine (633 µL, 614 mg, 4.2 mmol) in 15 mL of DCM and then coupled to unit 11b (306 mg, 0.42 mmol) using HBTU (319 mg, 0.84 mmol) and TEA (58 µL, 42 mg, 0.42 mmol) in 7 mL of anhydrous DMF. After separation by column chromatography 13b was obtained as a colorless solid. Yield 64% (448 mg, 0.23 mmol); TLC $R_f$ 0.40 (1:2 ethyl acetate/hexanes); mp 62-66° C.; $[\alpha]^{24}{}_D$+10.6 (c 0.18, chloroform); $^1$H NMR (CDCl$_3$, 400 MHz) δ 7.73 (2H, d, J=7.2 Hz), 7.66 (4H, m), 7.36 (3H, m), 7.29 (8H, m), 7.14 (1H, d, J=6.4 Hz), 5.66 (1H, d, J=7.2 Hz), 5.24 (5H, m), 5.10 (3H, m), 4.38 (3H, m), 4.22 (1H, t, J=7.2 Hz), 4.13 (4H, m), 4.02 (1H, m), 3.93 (1H, m), 2.27 (4H, m), 2.08 (1H, m), 1.74 (21H, m), 1.41 (12H, m), 1.21 (21H, m) and 1.02 (36H, m); $^{13}$C NMR (CDCl$_3$, 101 MHz) δ 171.45, 171.44, 171.41, 171.01, 170.98, 170.84, 170.79, 170.56, 170.54, 170.42, 170.41, 156.89, 143.98, 143.73, 141.39, 135.51, 130.57, 128.59, 128.33, 127.86, 127.18, 125.20, 120.11, 74.76, 72.86, 72.48, 72.01, 70.30, 70.14, 69.19, 67.64, 66.99, 60.36, 60.08, 59.98, 59.69, 59.39, 58.25, 47.17, 39.42, 39.05, 39.00, 34.76, 33.97, 33.80, 33.77, 33.71, 33.55, 32.50, 32.16, 32.08, 31.68, 30.30, 29.79, 29.75, 29.69, 29.48, 29.43, 28.63, 26.47, 26.45, 26.40, 26.38, 26.35, 26.23, 26.07, 26.03, 26.00, 25.38, 20.73, 19.47, 19.37, 19.27, 19.24, 19.18, 19.08, 19.05, 18.69, 17.33, 17.23 and 16.87; HRFTMS (ESI), m/z 1683.927 [M+Na]$^+$ (calcd for $C_{91}H_{132}N_6O_{22}Na$, 1683.929).

Fmoc-Tyr(tBu)-D-Hcha-D-Val-Lac-[Val-D-Hcha-D-Val-Lac]$_2$-OBn (13c): By employing the procedure followed for the preparation and purification of 5, unit 12 (500 mg, 0.42 mmol) was deprotected with 2,2',2''-triaminotriethylamine (633 µL, 614 mg, 4.2 mmol) in 15 mL of DCM and then condensed to unit 11c (329 mg, 0.42 mmol) using HBTU (319 mg, 0.84 mmol) and TEA (58 µL, 42 mg, 0.42 mmol) in 7 mL of anhydrous DMF. Following separation by column chromatography 13c was obtained as a colorless solid. Yield 74% (534 mg, 0.31 mmol); TLC R$_f$ 0.40 (1:2 ethyl acetate/hexanes); mp 61-65° C.; $[\alpha]^{24}_D$+14.3 (c 0.30, chloroform); $^1$H NMR (CDCl$_3$, 400 MHz) δ 7.73 (2H, d, J=7.6 Hz), 7.69 (1H, d, J=6.0 Hz), 7.65 (1H, d, J=6.0 Hz), 7.53 (3H, m), 7.38 (4H, m), 7.29 (7H, m), 7.06 (2H, d, J=8.4 Hz), 6.90 (2H, d, J=8.4 Hz), 5.74 (1H, d, J=6.4 Hz), 5.26 (5H, m), 5.09 (3H, m), 4.38 (4H, m), 4.20 (1H, m), 4.11 (2H, m), 4.00 (1H, m), 3.94 (1H, m), 3.09 (2H, m), 2.28 (5H, m), 1.65 (21H, m), 1.41 (12H, m), 1.21 (18H, m) and 1.02 (36H, m); $^{13}$C NMR (CDCl$_3$, 101 MHz) δ 171.67, 171.54, 171.63, 171.52, 171.45, 171.02, 170.93, 170.82, 170.59, 170.47, 170.42, 170.40, 156.64, 154.77, 143.92, 143.69, 141.37, 135.47, 130.19, 129.69, 128.54, 128.25, 127.82, 127.17, 125.15, 124.22, 120.06, 78.42, 72.95, 72.45, 72.03, 70.36, 70.15, 69.20, 67.58, 66.98, 59.95, 59.93, 59.73, 59.21, 58.26, 56.03, 47.09, 39.39, 39.08, 39.04, 39.03, 36.46, 34.74, 33.96, 33.95, 33.75, 33.70, 33.67, 33.63, 32.46, 32.18, 32.05, 31.66, 30.27, 29.69, 29.36, 29.27, 29.13, 28.94, 26.45, 26.39, 26.36, 26.06, 25.92, 25.35, 20.78, 19.41, 19.33, 19.30, 19.25, 19.24, 19.18, 19.05, 18.69, 17.38, 17.34, 16.83, 14.19 and 11.51; HRFTMS (ESI): m/z 1745.941 [M+Na]$^+$ (calcd for $C_{96}H_{134}N_6O_{22}Na$, 1745.944).

Cyclo-[Val-D-Hcha-D-Val-Lac]$_3$ (14a, Silstatin 4): Using the strategy followed for the preparation and purification of 7a, depsipeptide 13a (193 mg, 0.12 mmol) was deprotected using 20% palladium hydroxide-on-carbon (100 mg) in 8 mL of 4:1 ethyl acetate/methanol and then cyclized with PyBroP (224 mg, 0.48 mmol) and TEA (35 µL, 24 mg, 0.24 mmol) in 120 mL of anhydrous DCM. After separation by column chromatography silstatin 4 (14a) was obtained as a colorless solid. Yield 23% (35 mg, 27 µmol); TLC R$_f$ 0.5 (1:4 ethyl acetate/hexanes); mp 52-56° C.; $[\alpha]^{24}_D$+35.0 (c 0.06, chloroform); $^1$H NMR (CDCl$_3$, 400 MHz) δ 7.79 (3H, d, J=8.0 Hz), 7.73 (3H, d, J=6.4 Hz), 5.23 (3H, m), 5.17 (8.0 Hz, dd), 3.93 (3H, dd, J=9.6 Hz, 6.0 Hz), 2.23 (6H, m), 1.74 (21H, m), 1.46 (12H, m) and 1.02 (51H, m); $^{13}$C NMR (CDCl$_3$, 101 MHz) δ 172.4, 172.1, 171.5, 170.4, 72.9, 70.6, 60.3, 59.1, 39.4, 34.0, 33.9, 32.1, 28.7, 28.6, 26.6, 26.4, 26.1, 19.8, 19.6, 19.4, 19.2 and 17.3; HRMS (APCI), m/z 1273.779 [M+H]$^+$ (calcd for $C_{66}H_{109}N_6O_{18}$, 1273.780).

Cyclo-{Thr(tBu)-D-Hcha-D-Val-Lac-[Val-D-Hcha-D-Val-Lac]$_2$} (14b): Using the strategy followed for the preparation and purification of 7a, depsipeptide 13b (530 mg, 0.26 mmol) was deprotected using 20% palladium hydroxide-on-carbon (200 mg) in 10 mL of 4:1 ethyl acetate/methanol and then cyclized with PyBroP (485 mg, 1.04 mmol) and TEA (144 µL, 105 mg, 1.04 mmol) in 260 mL of anhydrous DCM. After separation by column chromatography 14b was obtained as a colorless solid. Yield 29% (100 mg, 75 µmol); TLC R$_f$ 0.4 (1:4 ethyl acetate/hexanes); mp 61-65° C.; $[\alpha]^{24}_D$+27.1 (c 0.09, chloroform); $^1$H NMR (CDCl$_3$, 400 MHz) δ 7.77 (1H, d, J=8.4 Hz), 7.69 (1H, d, J=7.2 Hz), 7.62 (1H, d, J=8.4 Hz), 7.42 (1H, d, J=8.0 Hz), 7.40 (1H, d, J=6.0 Hz), 7.29 (1H, d, J=5.2 Hz), 5.23 (5H, m), 5.13 (1H, dd, J=9.2 Hz, 3.6 Hz), 4.29 (1H, t, J=8.0 Hz), 4.23 (1H, t, J=8.0 Hz), 4.05 (4H, m), 3.85 (1H, dd, J=10 Hz, 5.6 Hz), 2.23 (5H, m), 1.74 (21H, m), 1.41 (12H, m), 1.21 (21H, m) and 1.02 (36H, m); $^{13}$C NMR (CDCl$_3$, 101 MHz) δ 172.29, 172.16, 172.08, 172.01, 171.78, 171.65, 171.17, 171.02, 170.19, 170.13, 169.94, 169.93, 74.84, 73.29, 72.77, 72.47, 71.04, 70.81, 70.70, 66.64, 60.82, 59.76, 59.10, 58.94, 58.23, 57.81, 39.50, 39.47, 39.43, 39.21, 36.77, 34.79, 34.13, 34.09, 34.03, 33.90, 33.83, 33.80, 32.22, 31.93, 31.83, 29.91, 29.35, 28.98, 28.68, 28.64, 28.59, 28.57, 28.52, 26.52, 26.42, 26.35, 26.09, 24.82, 20.15, 19.91, 19.53, 19.51, 19.42, 19.36, 19.29, 18.95, 18.58, 18.46, 17.50, 17.21 and 17.13; HRFTMS (ESI), m/z 1353.805 [M+Na]$^+$ (calcd for $C_{69}H_{114}N_6O_{19}Na$, 1353.803).

Cyclo-{Tyr(tBu)-D-Hcha-D-Val-Lac-[Val-D-Hcha-D-Val-Lac]$_2$} (14c): By means of the strategy followed for the preparation and purification of 7a, depsipeptide 13c (502 mg, 0.29 mmol) was deprotected using 20% palladium hydroxide-on-carbon (200 mg) in 8 mL of 4:1 ethyl acetate/methanol and then cyclized with PyBroP (541 mg, 1.16 mmol) and TEA (160 µL, 118 mg, 1.17 mmol) in 290 mL of anhydrous DCM. After separation by column chromatography cyclodepsipeptide 14c was obtained as a colorless solid. Yield 34% (145 mg, 0.10 mmol); TLC R$_f$ 0.4 (1:4 ethyl acetate/hexanes); mp 68-72° C.; $[\alpha]^{24}_D$+31.3 (c 0.12, chloroform); $^1$H NMR (CDCl$_3$, 400 MHz) δ 7.97 (1H, d, J=7.2 Hz), 7.93 (1H, d, J=6.0 Hz), 7.85 (1H, d, J=6.8 Hz), 7.75 (1H, d, J=8.4 Hz), 7.63 (1H, d, J=6.8 Hz), 7.58 (1H, d, J=5.6 Hz), 7.11 (2H, d, J=8.4 Hz), 6.88 (2H, d, J=8.0 Hz), 5.23 (3H, m), 5.13 (3H, m), 4.57 (q, J=7.2 Hz, 1H, J=9.2 Hz, 4.0 Hz, dd), 4.07 (3H, dd, J=9.2 Hz), 4.16 (1H, t, J=8.8 Hz), 3.99 (1H, dd, J=9.6 Hz, 7.2 Hz), 3.88 (3H, m), 3.11 (2H, m), 2.23 (5H, m) and 1.90-0.80 (87H, m); $^{13}$C NMR (CDCl$_3$, 101 MHz) δ 172.79, 172.76, 172.42, 172.15, 171.92, 171.75, 171.62, 171.55, 170.77, 170.45, 170.34, 170.10, 154.34, 131.42, 129.84, 124.13, 78.28, 73.37, 73.20, 72.54, 70.98, 70.71, 70.03, 60.76, 60.63, 59.69, 59.64, 58.33, 54.29, 39.50, 39.44, 39.25, 39.24, 35.29, 34.06, 33.89, 33.85, 33.69, 33.46, 32.88, 31.95, 31.85, 29.80, 29.02, 28.96, 28.76, 28.69, 28.67, 28.64, 28.61, 28.50, 26.52, 26.45, 26.39, 26.10, 26.07, 26.02, 19.96, 19.64, 19.49, 19.47, 19.40, 19.35, 19.32, 19.25, 18.92, 17.41, 17.27, 16.86 and 14.22; HRFTMS (ESI), m/z 1415.822 [M+Na]$^+$ (calcd for $C_{74}H_{116}N_6O_{19}Na$, 1415.819).

Cyclo-{Thr-D-Hcha-D-Val-Lac-[Val-D-Hcha-D-Val-Lac]$_2$} (15a, Silstatin 5): By the experimental route followed for the preparation and isolation of 8a, cyclodepsipeptide 14b (80 mg, 60 µmol) was deprotected with TFA (250 µL) in 2 mL of anhydrous DCM. After isolation by column chromatography yielded cyclodepsipeptide 15a (silstatin 5) as a colorless solid. Yield 91% (70 mg, 55 µmol); TLC R$_f$ 0.27 (1:3 ethyl acetate/hexanes); mp 58-63° C.; $[\alpha]^{24}_D$+32.0 (c 0.10, chloroform); $^1$H NMR (CDCl$_3$, 400 MHz) δ 7.96 (1H, d, J=6.8 Hz), 7.88 (1H, d, J=7.2 Hz), 7.76 (3H, m), 7.57 (1H, d, J=6.0 Hz), 5.20 (5H, m), 5.05 (1H, dd, J=9.2 Hz, 4.4 Hz), 4.12 (1H, t, J=9.2 Hz), 4.03 (4H, m), 3.88 (2H, m), 2.23 (4H, m), 2.11 (1H, m), 1.70 (21H, m), 1.41 (12H, m) and 1.21-0.90 (48H, m); $^{13}$C NMR (CDCl$_3$, 101 MHz) δ 173.36, 172.42, 172.26, 172.01, 171.96, 171.56, 171.36, 170.91, 170.61, 170.60, 170.28, 169.84, 73.80, 72.45, 72.34, 70.65, 70.60, 70.23, 66.01, 60.45, 60.36, 60.11, 59.60, 59.24, 58.37, 39.33, 39.07, 39.02, 34.62, 33.86, 33.75, 33.70, 33.65, 32.02, 31.96, 31.79, 28.61, 28.56, 28.47, 28.35, 28.11, 26.37, 26.35, 26.27, 26.22, 26.15, 25.97, 25.95, 25.93, 25.23, 19.62, 19.41, 19.40, 19.36, 19.34, 19.31, 19.30, 19.28, 19.27, 19.17, 19.15, 18.83, 17.35, 16.92 and 16.85; HRMS (APCI), m/z 1275.757 [M+H]$^+$ (calcd for $C_{65}H_{107}N_6O_{19}$, 1275.759).

Cyclo-{Tyr-D-Hcha-D-Val-Lac-[Val-D-Hcha-D-Val-Lac]$_2$} (15b, Silstatin 6): Again by the procedure followed for the preparation and purification of 8a, cyclodepsipeptide 14c (130 mg, 93 μmol) was deprotected with TFA (250 μL) in 2 mL of anhydrous DCM. After separation by column chromatography cyclodepsipeptide 15b (silstatin 6) was obtained as a colorless solid. yield 96% (120 mg, 90 μmol); TLC $R_f$ 0.28 (1:3 ethyl acetate/hexanes); mp 76-80° C.; [a]$^{24}_D$+26.2 (c 0.21, chloroform); $^1$H NMR (CDCl$_3$, 400 MHz) δ 7.84 (1H, d, J=7.2 Hz), 7.81 (1H, d, J=5.6 Hz), 7.77 (1H, d, J=8.4 Hz), 7.69 (1H, d, J=6.4 Hz), 7.63 (1H, d, J=6.0 Hz), 7.59 (1H, d, J=7.2 Hz), 7.02 (2H, d, J=8.8 Hz), 6.73 (2H, d, J=8.4 Hz), 5.23 (3H, m), 5.10 (3H, m), 4.50 (q, J=8.0 Hz, 1H), 4.15 (1H, t, J=8.8 Hz), 3.99 (2H, m), 3.88 (2H, m), 3.11 (2H, m), 2.23 (5H, m) and 1.90-0.80 (78H, m); $^{13}$C NMR (CDCl$_3$, 101 MHz) δ 172.65, 172.62, 172.32, 172.15, 171.92, 171.79, 171.76, 171.43, 170.84, 170.53, 170.35, 170.09, 155.46, 130.45, 127.60, 115.75, 73.49, 73.10, 72.57, 70.90, 70.76, 70.28, 60.75, 60.36, 59.17, 59.15, 58.56, 54.59, 39.45, 39.42, 39.40, 39.25, 39.24, 35.30, 34.79, 34.07, 33.88, 33.63, 33.57, 32.57, 31.92, 31.84, 31.70, 28.95, 28.91, 28.75, 28.74, 28.69, 26.51, 26.41, 26.12, 26.07, 25.96, 25.40, 22.77, 19.91, 19.79, 19.60, 19.46, 19.40, 19.30, 19.28, 19.27, 19.11, 18.97, 18.94, 17.39, 17.06 and 16.99; HRFTMS (ESI), m/z 1359.755 [M+Na]$^+$ (calcd for $C_{70}H_{108}N_6O_{19}Na$, 1359.756).

Compounds 18a and 18b were synthesized according to the method depicted in Scheme 3.

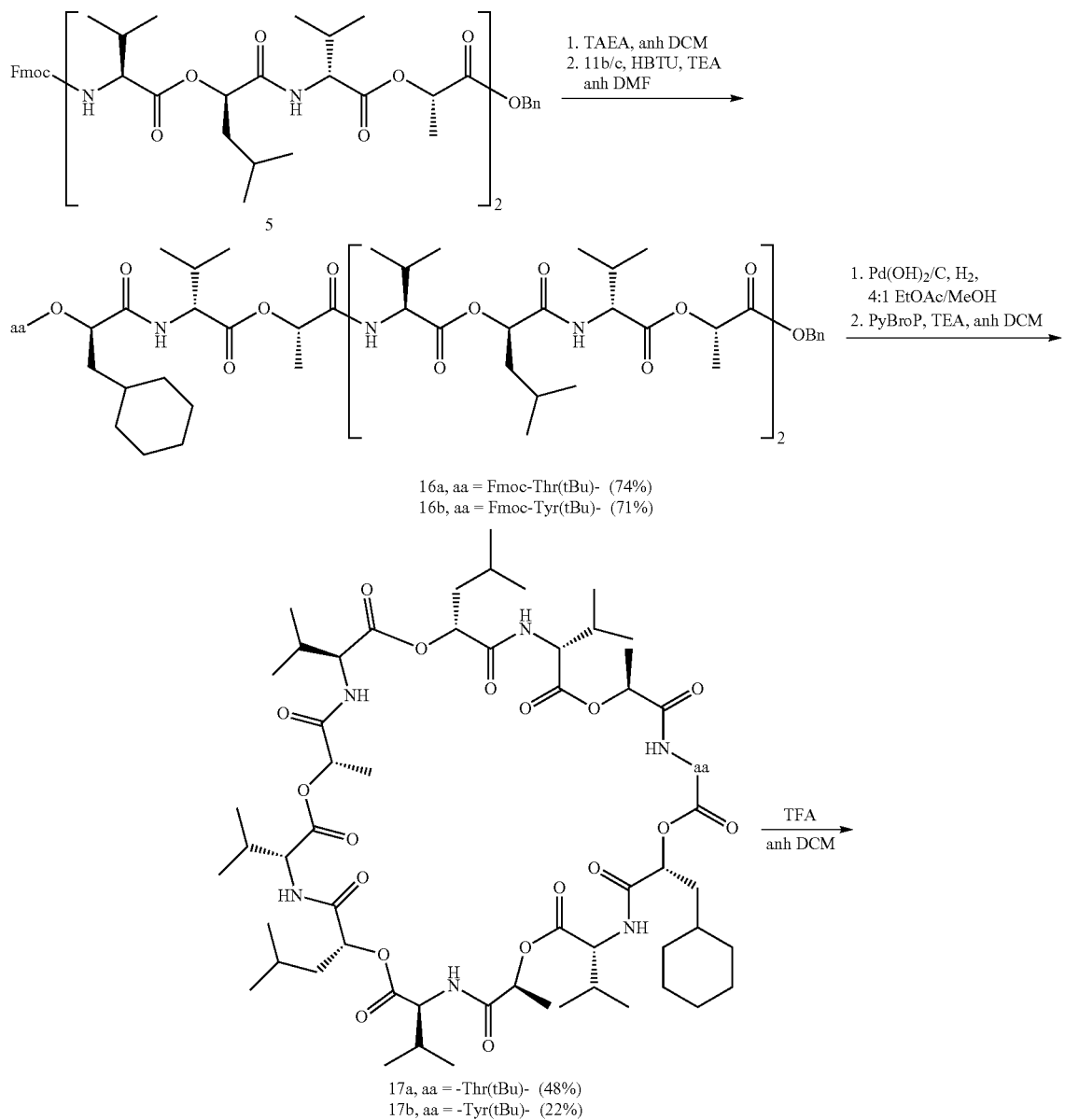

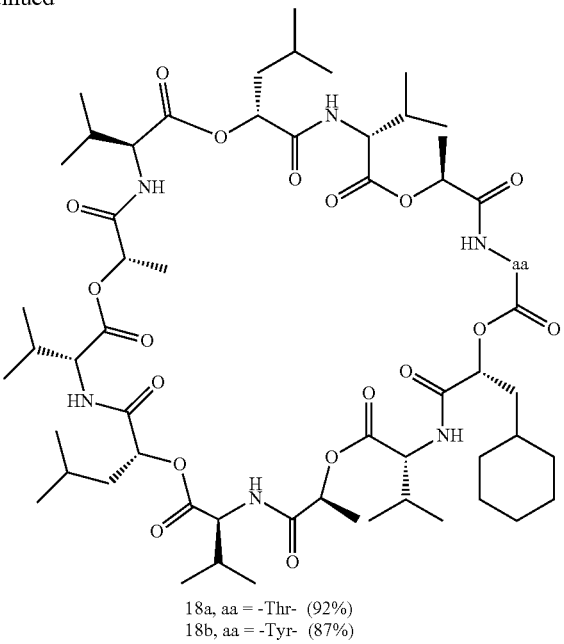

18a, aa = -Thr- (92%)
18b, aa = -Tyr- (87%)

Fmoc-Thr(tBu)-D-Hcha-D-Val-Lac-[Val-D-Hica-D-Val-Lac]$_2$-OBn (16a): Application of the method followed for the preparation and isolation of 5, unit 5 (264 mg, 0.24 mmol) was deprotected with 2,2',2''-triaminotriethylamine (362 µL, 351 mg, 2.4 mmol) in 15 mL of DCM and then coupled to unit 11b (170 mg, 0.24 mmol) using HBTU (182 mg, 0.48 mmol) and TEA (33 µL, 24 mg, 0.24 mmol) in 5 mL of anhydrous DMF. Separation by column chromatography provided 16a which was obtained as a colorless solid. Yield 74% (281 mg, 0.18 mmol); TLC $R_f$ 0.50 (1:2 ethyl acetate/hexanes); mp 56-60° C.; $[\alpha]^{24}_D$+7.62 (c 0.11, chloroform); $^1$H NMR (CDCl$_3$, 400 MHz) δ 7.74 (2H, d, J=7.2 Hz), 7.70 (1H, d, J=6.0 Hz), 7.55 (4H, m), 7.39 (2H, m) 7.29 (8H, m), 7.14 (1H, d, J=6.4 Hz), 5.65 (1H, d, J=7.2 Hz), 5.24 (5H, m), 5.10 (3H, m), 4.38 (3H, m), 4.22 (1H, t, J=7.2 Hz), 4.13 (4H, m), 3.98 (1H, m), 3.92 (1H, m), 2.27 (5H, m), 1.74 (13H, m), 1.41 (10H, m), 1.09 (15H, m) and 0.98 (44H, m); $^{13}$C NMR (CDCl$_3$, 101 MHz) δ 171.45, 171.38, 171.34, 171.03, 170.96, 170.91, 170.76, 170.69, 170.53, 170.48, 170.37, 170.36, 156.88, 143.95, 143.71, 141.38, 135.48, 128.58, 128.32, 128.26, 127.84, 127.16, 125.17, 120.09, 74.75, 73.10, 72.82, 72.62, 70.27, 70.18, 69.17, 67.63, 66.98, 66.94, 64.43, 60.35, 60.07, 59.97, 59.61, 59.42, 58.17, 47.15, 40.90, 40.43, 39.04, 33.80, 33.53, 32.47, 30.34, 29.76, 29.64, 29.44, 29.43, 28.61, 26.38, 26.21, 25.98, 24.48, 24.44, 23.33, 21.51, 21.44, 20.71, 19.47, 19.37, 19.31, 19.26, 19.23, 19.20, 19.15, 19.08, 19.06, 18.63, 17.36, 17.23 and 16.85; HRFTMS (ESI), m/z 1603.867 [M+Na]$^+$ (calcd for C$_{84}$H$_{124}$N$_6$O$_{22}$Na, 1603.866).

Fmoc-Tyr(tBu)-D-Hcha-D-Val-Lac-[Val-D-Hica-D-Val-Lac]$_2$-OBn (16b): By following the experimental used for the synthesis and purification of 5, that unit (5) (221 mg, 0.20 mmol) was deprotected with 2,2',2''-triaminotriethylamine (302 µL, 293 mg, 2.0 mmol) in 15 mL of DCM and then coupled to unit 11c (158 mg, 0.20 mmol) using HBTU (152 mg, 0.40 mmol) and TEA (28 µL, 20 mg, 0.20 mmol) in 5 mL of anhydrous DMF. After isolation by column chromatography afforded 16b as a colorless solid in a 71% yield (232 mg, 0.14 mmol); TLC $R_f$ 0.45 (1:2 ethyl acetate/hexanes); mp 58-62° C.; $[\alpha]^{24}_D$+15.3 (c 0.09, chloroform); $^1$H NMR (CDCl$_3$, 400 MHz) δ 7.74 (3H, m), 7.65 (1H, d, J=7.2 Hz), 7.55 (3H, m), 7.30 (11H, m), 7.06 (2H, d, J=8.0 Hz), 6.89 (2H, d, J=8.4 Hz), 5.79 (1H, d, J=6.8 Hz), 5.24 (5H, m), 5.08 (3H, m), 4.38 (3H, m), 4.05 (5H, m), 3.03 (2H, m), 2.25 (5H, m), 1.70 (13H, m), 1.41 (10H, m), 1.32 (9H, s), 1.09 (3H, m) and 0.98 (44H, m); $^{13}$C NMR (CDCl$_3$, 101 MHz) δ 171.68, 171.57, 171.54, 171.42, 171.38, 170.93, 170.72, 170.58, 170.45, 170.43, 170.42, 170.38, 156.64, 154.73, 143.89, 143.67, 141.35, 135.42, 129.67, 128.54, 128.29, 128.23, 127.81, 127.15, 125.13, 124.21, 120.05, 78.43, 73.08, 72.92, 72.66, 70.22, 69.21, 67.55, 66.99, 59.91, 59.89, 59.87, 59.86, 59.60, 59.21, 58.18, 56.01, 47.07, 40.86, 40.47, 39.07, 36.44, 34.72, 33.66, 33.61, 32.43, 31.64, 30.33, 29.73, 29.40, 29.36, 29.28, 29.11, 28.92, 26.37, 26.04, 25.90, 25.34, 24.46, 24.44, 23.32, 23.31, 21.52, 21.41, 19.39, 19.30, 19.26, 19.23, 19.19, 19.14, 19.05, 18.62, 17.37 and 16.83; HRFTMS (ESI), m/z 1665.877 [M+Na]$^+$ (calcd for C$_{90}$H$_{126}$N$_6$O$_{22}$Na, 1665.882).

Cyclo-{Thr(tBu)-D-Hcha-D-Val-Lac-[Val-D-Hica-D-Val-Lac]$_2$} (17a): By employing the route followed for obtaining 7a, depsipeptide 16a (269 mg, 0.17 mmol) was deprotected using 20% palladium hydroxide-on-carbon (200 mg) in 8 mL of 4:1 ethyl acetate/methanol and then cyclized employing PyBroP (317 mg, 0.68 mmol) and TEA (94 µL, 69 mg, 0.68 mmol) in 170 mL of anhydrous DCM. Separation by column chromatography provided 17a as a colorless solid in 48% yield (102 mg, 81 µmol); TLC $R_f$ 0.3 (1:4 ethyl acetate/hexanes); mp 58-62° C.; $[\alpha]^{24}_D$+17.3 (c 0.08, chloroform); $^1$H NMR (CDCl$_3$, 400 MHz) δ 7.78 (1H, d, J=8.0 Hz), 7.71 (1H, d, J=7.2 Hz), 7.62 (1H, d, J=8.4 Hz), 7.43 (2H, m), 7.33 (1H, d, J=4.8 Hz), 5.18 (6H, m), 4.28 (1H, t, J=8.0 Hz), 4.22 (1H, t, J=8.0 Hz), 4.05 (4H, m), 3.85 (1H, dd, J=10 Hz, 5.6 Hz), 2.23 (5H, m), 1.74 (13H, m), 1.43 (10H, m) and 1.25-0.9 (59H, m); $^{13}$C NMR (CDCl$_3$, 101 MHz) δ 172.31, 172.21, 172.06, 171.97, 171.69, 171.20, 171.09, 170.24, 170.22, 170.14, 169.99, 169.94, 74.80, 73.41, 73.28, 73.12, 70.99, 70.79, 70.68, 66.61, 60.79, 59.77, 59.12, 58.97, 58.27, 57.84, 40.94, 40.69, 39.46, 34.03, 33.77, 32.20, 29.83, 29.80, 29.29, 28.91, 28.65, 28.56, 28.49, 26.49, 26.33, 26.07, 24.60, 24.55, 23.50, 21.29, 21.18, 20.12, 19.87, 19.53, 19.51, 19.40, 19.37, 19.33, 19.29, 18.96, 18.60, 18.47, 17.48, 17.19 and 17.12; HRMS (APCI), m/z 1251.760 [M+H]$^+$ (calcd for $C_{63}H_{107}N_6O_{19}$, 1251.759).

Cyclo-{Tyr(tBu)-D-Hcha-D-Val-Lac-[Val-D-Hica-D-Val-Lac]$_2$} (17b): The preceding method followed for synthesis and isolation of 7a, depsipeptide 16b (220 mg, 0.13 mmol) was deprotected using 20% palladium hydroxide-on-carbon (200 mg) in 8 mL of 4:1 ethyl acetate/methanol and then cyclized with PyBroP (250 mg, 0.54 mmol) and TEA (74 µL, 54 mg, 0.54 mmol) in 134 mL of anhydrous DCM. Isolation by column chromatography yielded 17b as a colorless solid. Yield 22% (38 mg, 29 µmol); TLC $R_f$ 0.3 (1:4 ethyl acetate/hexanes); mp 55-59° C.; $[\alpha]^{24}_D$+24.3 (c 0.07, chloroform); $^1$H NMR (CDCl$_3$, 400 MHz) δ 7.98 (1H, d, J=7.2 Hz), 7.94 (1H, d, J=5.6 Hz), 7.85 (1H, d, J=7.2 Hz), 7.74 (1H, d, J=8.8 Hz), 7.63 (1H, d, J=6.8 Hz), 7.59 (1H, d, J=5.6 Hz), 7.12 (2H, d, J=8.4 Hz), 6.88 (2H, d, J=8.4 Hz), 5.23 (5H, m), 5.13 (1H, m), 4.58 (q, J=7.6 Hz, 1H), 4.18 (1H, t, J=8.8 Hz), 4.01 (1H, dd, J=10 Hz, 7.6 Hz), 3.88 (3H, m), 3.11 (2H, m), 2.23 (5H, m) and 1.90-0.80 (73H, m); $^{13}$C NMR (CDCl$_3$, 101 MHz) δ 172.64, 172.53, 172.29, 172.02, 171.78, 171.60, 171.52, 171.31, 170.57, 170.35, 170.10, 169.92, 154.19, 131.28, 129.68, 123.97, 78.15, 73.78, 73.18, 73.08, 70.81, 70.58, 69.86, 60.55, 59.58, 59.47, 58.13, 54.12, 40.73, 40.58, 39.29, 35.10, 35.09, 33.51, 33.33, 32.73, 29.66, 28.82, 28.62, 28.56, 28.49, 28.45, 28.33, 26.35, 25.91, 25.86, 24.46, 24.45, 23.35, 23.32, 21.15, 21.03, 19.82, 19.80, 19.50, 19.35, 19.31, 19.27, 19.18, 19.16, 18.75, 17.27, 17.15 and 16.68; HRMS (APCI), m/z 1313.777 [M+H]$^+$ (calcd for $C_{68}H_{109}N_6O_{19}$, 1313.775).

Cyclo-{Thr-D-Hcha-D-Val-Lac-[Val-D-Hica-D-Val-Lac]$_2$} (18a, Silstatin 7): By using the procedure used for the synthesis and isolation of 8a, cyclodepsipeptide 17a (80 mg, 64 µmol) was deprotected with TFA (250 µL) in 1 mL of anhydrous DCM. After separation by column chromatography 18a (silstatin 7) was obtained as a colorless solid. Yield 92% (70 mg, 59 µmol); TLC $R_f$ 0.27 (1:3 ethyl acetate/hexanes); mp 75-79° C.; $[\alpha]^{24}_D$+18.8 (c 0.09, chloroform); $^1$H NMR (CDCl$_3$, 400 MHz) δ 7.97 (1H, d, J=6.8 Hz), 7.88 (1H, d, J=7.2 Hz), 7.76 (3H, m), 7.57 (1H, d, J=6.0 Hz), 5.20 (5H, m), 5.05 (1H, dd, J=8.8 Hz, 4.0 Hz), 4.75 (1H, br s), 4.12 (1H, t, J=8.8 Hz), 3.95 (6H, m), 2.23 (4H, m), 2.11 (1H, m), 1.74 (13H, m), 1.43 (10H, m) and 1.25-0.9 (50H, m); $^{13}$C NMR (CDCl$_3$, 101 MHz) δ 173.4, 172.65, 172.30, 172.23, 172.13, 171.75, 171.57, 171.07, 170.94, 170.80, 170.40, 170.00, 73.91, 73.31, 73.19, 70.79, 70.72, 70.43, 66.16, 60.69, 60.48, 60.21, 59.86, 59.44, 58.59, 40.82, 40.73, 39.16, 34.00, 33.87, 32.12, 28.73, 28.68, 28.62, 28.52, 28.26, 26.50, 26.30, 26.10, 24.59, 24.58, 23.46, 23.34, 21.54, 21.34, 19.76, 19.58, 19.53, 19.49, 19.48, 19.47, 19.46, 19.45, 19.42, 19.32, 19.02, 17.50 and 17.05; HRMS (APCI), m/z 1195.696 [M+H]$^+$ (calcd for $C_{59}H_{99}N_6O_{19}$, 1195.697).

Cyclo-{Tyr-D-Hcha-D-Val-Lac-[Val-D-Hica-D-Val-Lac]$_2$} (18b, Silstatin 8): By using the general procedure for the preparation and isolation of 8a, cyclodepsipeptide 17b (30 mg, 23 µmol) was deprotected with TFA (250 µL) in 1 mL of anhydrous DCM. Separation by column chromatography led to 18b (silstatin 8) as a colorless solid. Yield 87% (25 mg, 20 µmol); TLC $R_f$ 0.27 (1:3 ethyl acetate/hexanes); mp 78-82° C.; $[\alpha]^{24}_D$+21.3 (c 0.08, chloroform); $^1$H NMR (CDCl$_3$, 400 MHz) δ 7.80 (3H, m), 7.67 (2H, m), 7.61 (1H, d, J=7.2 Hz), 7.05 (2H, d, J=8.0 Hz), 6.74 (2H, d, J=8.0 Hz), 6.03 (1H, br s), 5.23 (3H, m), 5.09 (3H, m), 4.48 (q, J=7.4 Hz, 1H), 4.14 (1H, t, J=8.8 Hz), 4.05 (2H, m), 3.93 (2H, m), 3.05 (2H, m), 2.23 (5H, m), 1.77 (7H, m), 1.60 (7H, m), 1.45 (6H, d, J=6.8 Hz), 1.36 (3H, d, J=6.8 Hz) and 1.11-0.80 (47H, m); $^{13}$C NMR (CDCl$_3$, 101 MHz) δ 172.60, 172.44, 172.34, 172.22, 171.88, 171.78, 171.69, 171.49, 170.99, 170.45, 170.36, 170.14, 155.25, 130.52, 127.80, 115.81, 73.75, 73.54, 73.26, 70.86, 70.72, 70.38, 60.75, 60.31, 59.04, 59.01, 58.69, 54.69, 40.91, 40.74, 39.41, 35.32, 33.64, 33.62, 32.54, 29.85, 29.04, 28.91, 28.75, 28.72, 28.67, 26.53, 26.09, 25.97, 24.66, 24.63, 23.50, 23.49, 21.33, 21.21, 19.91, 19.76, 19.62, 19.50, 19.42, 19.36, 19.35, 19.07, 18.99, 18.89, 17.44 and 17.06; HRMS (APCI), m/z 1257.713 [M+H]$^+$ (calcd for $C_{64}H_{101}N_6O_{19}$, 1257.712).

Methyl 1-(4-formyl-2-nitrophenyl)-2,3,4-tri-O-acetyl-β-D-glucuronate (19): Employing the strategy presented by Duimstra et al.,[11] 1-bromo-2,3,4-tri-O-acetyl-α-D-glucuronate (2.32 g, 5.84 mmol) was coupled to 4-hydroxy-3-nitrobenzaldehyde (1.66 g, 9.93 mmol) using Ag$_2$O (6.14 g, 26.5 mmol) in 20 ml of anhydrous acetonitrile. Yield 93% (2.62 g, 5.42 mmol); $^1$H NMR (CDCl$_3$, 400 MHz) δ 9.98 (1H, s), 8.32 (1H, d, J=1.6 Hz), 8.10 (1H, dd, J=8.0 Hz, 1.6 Hz), 7.52 (1H, d, J=8.8 Hz), 5.43 (2H, m), 5.31 (2H, m), 4.34 (1H, d, J=8.8 Hz), 3.71 (3H, s), 2.13 (3H, s), 2.09 (3H, s) and 2.08 (3H, s); $^{13}$C NMR (CDCl$_3$, 101 MHz) δ 188.7, 170.0, 169.4, 169.2, 166.8, 153.4, 141.2, 134.4, 131.6, 126.8, 118.9, 98.7, 72.8, 70.3, 69.9, 68.2, 53.2, 20.7 and 20.7.

Compound 28 was synthesized according to the method depicted in Scheme 4.

Scheme 4.

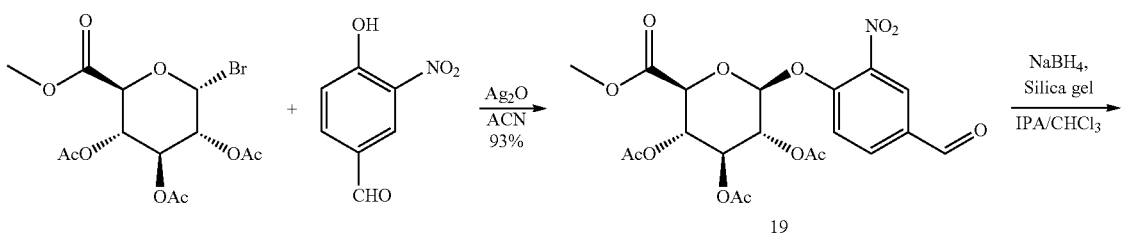

-continued
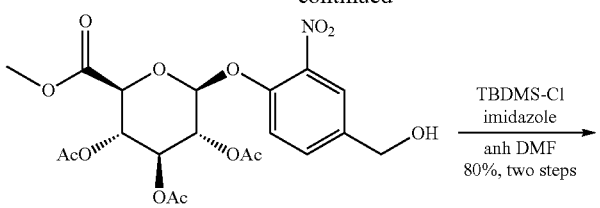
20
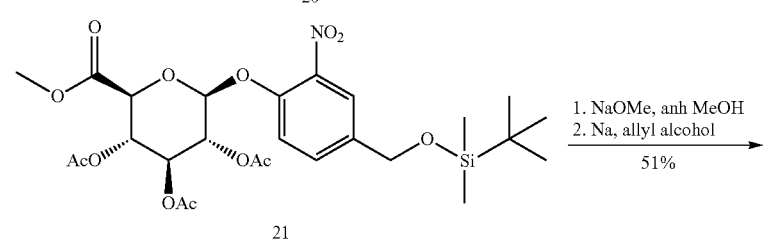
21
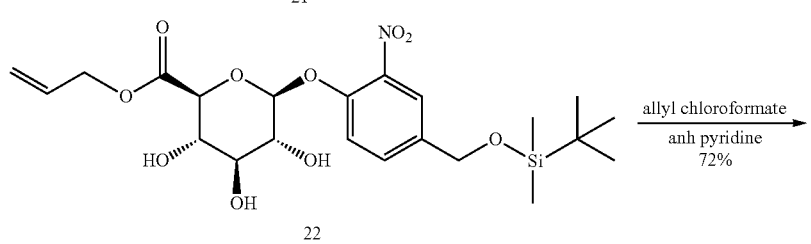
22
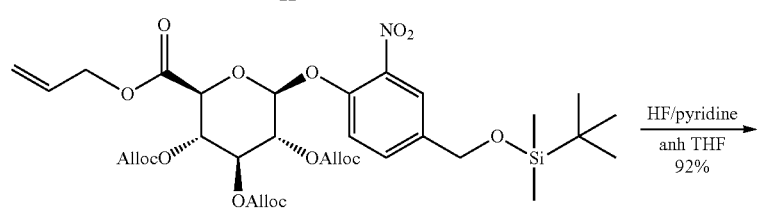
23
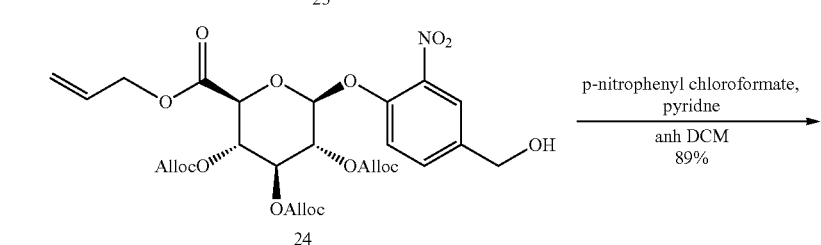
24
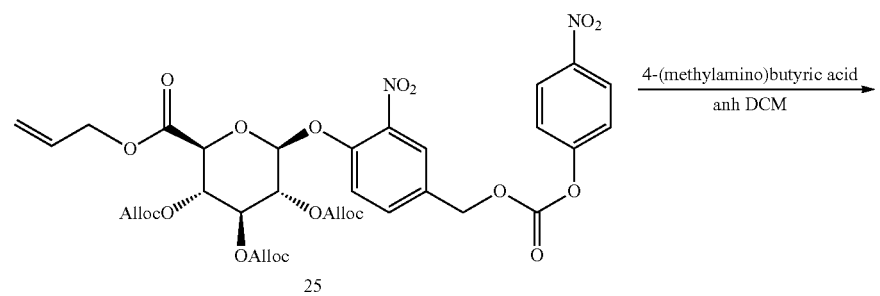
25
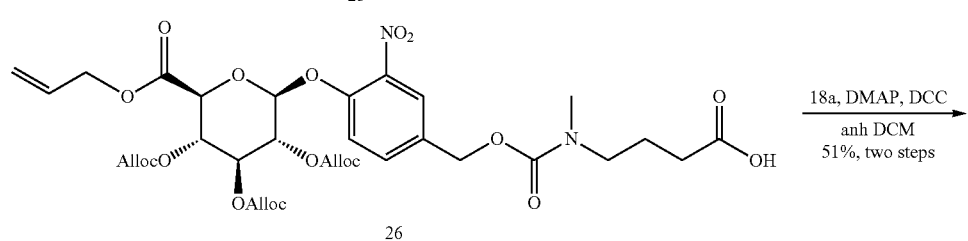
26

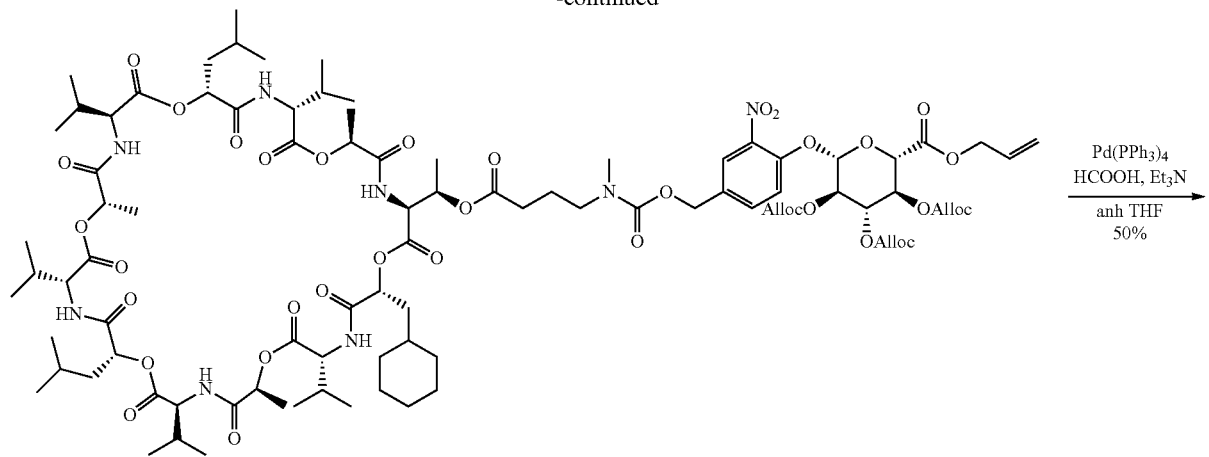

27

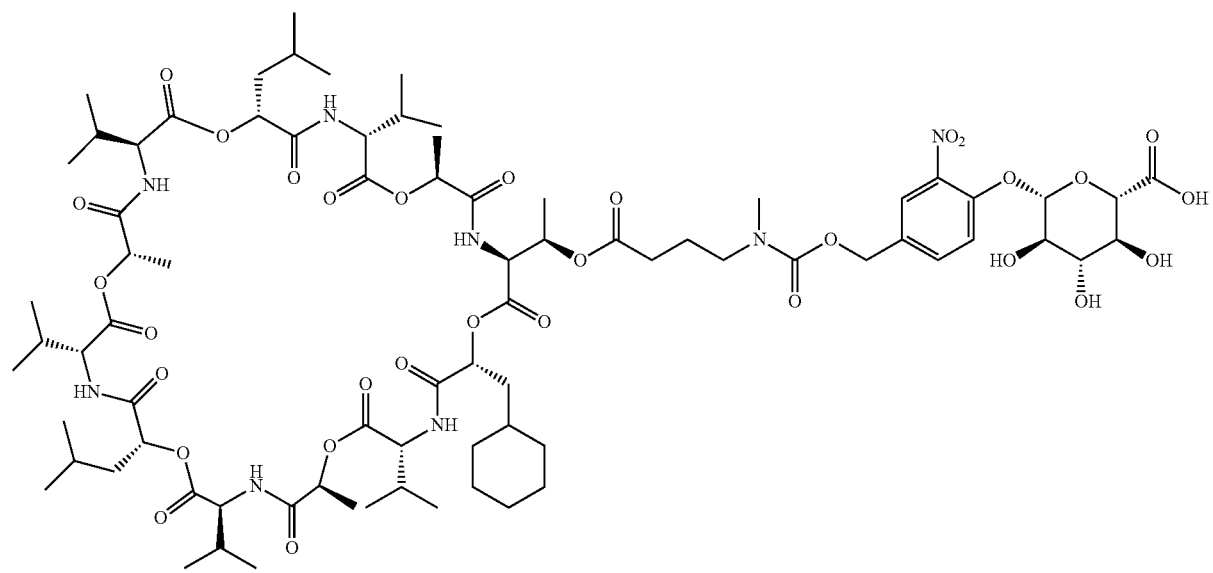

28

Methyl 1-(4-(tert-butyldimethylsilyloxy)methyl-2-nitrophenyl)-2,3,4-tri-O-acetyl-β-D-glucuronate (21): By means of the synthesis presented by Duimstra et al.,[11] glucuronate 19 (2.60 g, 5.38 mmol) was reduced with sodium borohydride (305 mg, 8.07 mmol) in the presence of silica (1.08 g) in 65 mL of 1:5 isopropanol/chloroform and then silyl protected using TBDMS-Cl (1.22 g, 8.07 mmol) and imidazole (549 mg, 8.07 mmol) in 30 mL of anhydrous DCM. After separation by column chromatography 21 was obtained as a colorless solid. Yield 80% (2.58 g, 4.30 mmol); TLC $R_f$ 0.25 (1:2 ethyl acetate/hexanes); $^1$H NMR (CDCl$_3$, 400 MHz) δ 7.75 (1H, d, J=2.4 Hz), 7.45 (1H, dd, J=8.8 Hz, 2.4 Hz), 7.32 (1H, d, J=8.4 Hz), 5.31 (3H, m), 5.17 (1H, d, J=7.2 Hz), 4.72 (2H, s), 4.19 (1H, d, J=9.2 Hz), 3.75 (3H, s), 2.13 (3H, s), 2.06 (3H, s), 2.05 (3H, s), 0.94 (9H, s) and 0.11 (6H, s); $^{13}$C NMR (CDCl$_3$, 101 MHz) δ 170.16, 169.44, 169.43, 166.87, 147.92, 141.45, 138.24, 131.19, 122.56, 120.35, 100.23, 72.75, 71.37, 70.39, 68.97, 63.53, 53.18, 26.01, 20.74, 20.71, 20.65 and −5.18.

Allyl 1-(4-(tert-butyldimethylsilyloxy)methyl-2-nitrophenyl)-β-D-glucuronate (22): By employing the procedure recorded by Grinda et al.,[12] glucuronate 21 (1.58 g, 2.63 mmol) was deacetylated with 0.5 N sodium methoxide in methanol (5.26 mL, 2.63 mmol) in 50 mL of anhydrous methanol and then transesterified with a sodium allylate solution (prepared by dissolving sodium (12 mg, 0.53 mmol) in 5 mL of allyl alcohol). By means of separation by column chromatography 22 was obtained as a colorless solid. Yield 51% (671 mg, 1.34 mmol); TLC $R_f$ 0.25 (1:1 acetone/hexanes); $^1$H NMR (CDCl$_3$, 400 MHz) δ 7.71 (1H, d, J=2.4 Hz), 7.42 (1H, dd, J=8.4 Hz, 2.0 Hz), 7.29 (1H, d, J=8.4 Hz), 5.87 (1H, m), 5.32 (1H, m), 5.20 (1H, m), 5.02 (1H, d, J=7.2 Hz), 4.81 (1H, br s), 4.66 (4H, m), 4.39 (1H, br s), 4.28 (1H, br s), 4.11 (1H, d, J=9.6 Hz), 3.92 (1H, m), 3.78 (1H, m), 0.91 (9H, s) and 0.07 (6H, s); $^{13}$C NMR (CDCl$_3$, 101 MHz) δ 168.4, 149.1, 140.3, 137.0, 131.8, 131.4, 122.9, 119.1, 118.8, 102.3, 75.1, 74.8, 72.9, 71.0, 66.6, 63.5, 26.0, 18.5 and −5.2.

Allyl 1-(4-(tert-butyldimethylsilyloxy)methyl-2-nitrophenyl)-2,3,4-tri-O-allyloxycarbonyl-β-D-glucuronate (23): Application of the experimental recommended by Grinda et al.,[12] the free hydroxyl groups of glucuronate 22 (200 mg, 0.40 mmol) were protected using allyl chloroformate (1.28 mL, 1.45 g, 12.0 mmol) in 2 mL of anhydrous pyridine and following separation by column chromatography 23 was obtained as a colorless oil. Yield 72% (216 mg, 0.29 mmol); TLC $R_f$ 0.4 (1:3 ethyl acetate/hexanes); $^1$H NMR (CDCl$_3$, 400 MHz) δ 7.72 (1H, d, J=2.4 Hz), 7.45 (1H, dd, J=8.8 Hz, 2.4 Hz), 7.29 (1H, d, J=8.4 Hz), 5.87 (4H, m), 5.33 (3H, m), 5.20 (7H, m), 4.68 (4H, m), 4.59 (6H, m), 4.31 (1H, m), 0.91 (9H, s) and 0.07 (6H, s); $^{13}$C NMR (CDCl$_3$, 101 MHz) δ 165.73, 154.03, 153.55, 153.54, 147.96, 140.99, 137.99, 131.31, 131.22, 131.15, 131.04, 130.97, 122.68, 119.38, 119.35, 119.32, 119.27, 119.05, 99.83, 75.15, 74.07, 72.49, 72.26, 69.54, 69.33, 69.18, 66.94, 63.42, 25.94, 18.41 and −5.24.

Allyl 1-(4-hydroxymethyl-2-nitrophenyl)-2,3,4-tri-O-allyloxycarbonyl-β-D-glucuronate (24): Again following the procedure presented by Grinda et al.,[12] compound 23 (409 mg, 0.54 mmol) was deprotected using a 7:3 HF/Pyridine solution (2.05 mL) in 10 mL of anhydrous tetrahydrofuran. Column chromatography using ethyl acetate/hexanes gave 24 as a colorless oil. Yield 92% (316 mg, 0.50 mmol); TLC $R_f$ 0.20 (1:3 ethyl acetate/hexanes); $^1$H NMR (CDCl$_3$, 400 MHz) δ 7.76 (1H, d, J=2.0 Hz), 7.45 (1H, dd, J=8.4 Hz, 2.0 Hz), 7.29 (1H, d, J=8.4 Hz), 5.87 (4H, m), 5.33 (4H, m), 5.20 (8H, m), 4.67 (10H, m) and 4.35 (1H, d, J=8.8 Hz); $^{13}$C NMR (CDCl$_3$, 101 MHz) δ 165.80, 154.04, 153.58, 153.56, 148.16, 140.75, 137.52, 132.11, 131.24, 131.10, 131.00, 130.92, 123.33, 119.44, 119.37, 119.34, 119.12, 119.09, 99.54, 75.15, 74.07, 72.45, 72.07, 69.61, 69.36, 69.22, 67.01 and 63.25.

Allyl 1-(4-(O-4-nitrophenyloxycarbonyl)methyl-2-nitrophenyl)-2,3,4-O-allyloxycarbonyl-β-D-glucuronate (25): Following the procedure presented by Grinda et al.,[12] compound 24 (316 mg, 0.50 mmol) was activated using 4-nitrophenyl chloroformate (202 mg, 1.00 mmol) and pyridine (101 μL, 99 mg, 1.25 mmol) in 10 mL of anhydrous dichloromethane. After separation by column chromatography 25 was obtained as a colorless oil. Yield 89% (356 mg, 0.44 mmol). TLC $R_f$ 0.4 (2:3 ethyl acetate/hexanes); $^1$H NMR (CDCl$_3$, 400 MHz) δ 8.27 (2H, d, J=8.8 Hz), 7.87 (1H, d, J=2.0 Hz), 7.58 (1H, dd, J=8.4 Hz, 2.0 Hz), 7.29 (3H, m), 5.84 (4H, m), 5.33 (14H, m), 4.65 (8H, m) and 4.35 (1H, d, J=9.2 Hz); $^{13}$C NMR (CDCl$_3$, 101 MHz) δ 165.70, 155.36, 154.04, 153.55, 153.51, 152.39, 149.50, 145.60, 140.87, 134.20, 131.20, 131.11, 130.99, 130.90, 130.36, 125.68, 125.44, 121.86, 119.52, 119.45, 119.42, 119.22, 119.13, 99.35, 74.89, 73.93, 72.31, 72.30, 69.65, 69.40, 69.27, 68.93 and 67.05.

Allyl protected glucuronide prodrug (27): To a stirred solution containing 4-(methylamino)butyric acid (38 mg, 0.32 mmol) in 1 mL of anhydrous DMF was added potassium carbonate (88 mg, 0.64 mmol) followed by compound 25 (256 mg, 0.32 mmol). The reaction mixture was stirred at 23° C. for 30 min, diluted with 60 mL of ethyl acetate, washed with 20 mL of 6% aq citric acid, 25 mL of brine, dried over MgSO$_4$ and concentrated under reduced pressure. The residue was partially separated using a short silica gel plug to remove the 4-nitrophenol and afford intermediate 26 as a colorless oil; crude yield 80% (200 mg). Next, intermediate 26 (130 mg, 0.17 mmol) was dissolved in 3 mL of anhydrous DCM and compound 18a (167 mg, 0.14 mmol) was added followed by DMAP (5 mg, 0.04 mmol) and DCC (31 mg, 0.15 mmol). The reaction mixture was stirred at 23° C. for 16 h. The solvent was separated by filtration and the filtrate was concentrated under reduced pressure. The crude product was separated by chromatography on a silica gel column. Elution with 3:2 hexanes/ethyl acetate gave the allyl protected prodrug 27 as a colorless solid: yield 51% over two steps (176 mg, 90 μmol). TLC $R_f$ 0.25 (2:3 ethyl acetate/hexanes); mp 76-79° C.; $[α]^{24}_D$ +12.0 (c 0.03, chloroform); $^1$H NMR (CDCl$_3$, 400 MHz) δ 7.93 (1H, m), 7.77 (6H, m), 7.53 (1H, dd, J=8.8 Hz, 2.0 Hz), 7.33 (1H, d, J=8.8 Hz), 5.84 (4H, m), 5.25 (16H, m), 5.09 (4H, m), 4.65 (8H, m), 4.69 (8H, m), 4.48 (1H, dd, J=8.4 Hz, 6.4 Hz), 4.33 (1H, d, J=8.8 Hz), 4.08 (5H, m), 3.90 (1H, m), 3.47 (2H, m), 3.32 (3H, m), 2.92 (3H, m), 2.26 (5H, m), 1.77 (15H, m), 1.36 (13H, m), 1.08 (20H, m) and 0.94 (27H, m); $^{13}$C NMR (CDCl$_3$, 101 MHz) δ 172.32, 172.26, 172.06, 172.03, 172.01, 171.84, 171.69, 171.57, 171.49, 170.46, 170.28, 170.08, 165.54, 156.71, 153.89, 153.41, 153.40, 148.68, 140.87, 133.38, 131.12, 131.00, 130.88, 130.79, 124.74, 119.89, 119.34, 119.26, 119.24, 119.21, 118.97, 99.54, 74.87, 73.83, 73.40, 73.27, 73.15, 72.27, 72.22, 70.47, 70.41, 70.37, 69.45, 69.22, 69.11, 68.50, 66.86, 65.17, 60.52, 59.88, 58.74, 58.63, 57.62, 49.10, 40.63, 40.57, 39.15, 34.62, 33.92, 33.73, 33.69, 32.12, 31.54, 28.62, 28.53, 28.49, 26.30, 26.16, 25.92, 25.58, 25.23, 24.90, 24.45, 24.41, 23.45, 23.23, 22.62, 22.61, 21.24, 20.95, 20.66, 19.71, 19.43, 19.39, 19.29, 19.24, 19.03, 18.92, 18.87, 17.21, 16.98, 16.88 and 14.07; HRFTMS (ESI), m/z 1979.8054 [M+Na]$^+$ (calcd for C$_{93}$H$_{136}$N$_8$O$_{37}$Na, 1979.8899).

Glucuronide prodrug (28): To a stirred solution containing protected prodrug 27 (24 mg, 12 μmol) in 1 mL of anhydrous tetrahydrofuran was added a solution containing formic acid (1.4 μL, 1.7 mg, 36 μmol) and TEA (8.3 μL, 6.1 mg, 60 μmol) of in 100 μL of anhydrous tetrahydrofuran. The reaction mixture was stirred at 23° C. for 10 min, then Pd(PPh$_3$)$_4$ (1.4 mg, 1.2 μmol) was added, the mixture was stirred at 23° C. for 2.5 h and then concentrated under reduced pressure. The crude product was separated by reverse phase HPLC. Column: Phenomenex Luna C8(2), 250×10 mm, 5 μm. Flow rate: 3.5 mL/min. Solvents: A) 50 mM NH$_4$OAc (pH=3.5); B) ACN. Isocratic elution with 20% A in B from 0 to 10 min; next, gradient elution from 20% A in B to 1% A in B from min 10 to min 12; finally, isocratic elution with 1% A in B from min 12 to min 18. Retention time: 15.5 min. To provide a colorless solid: yield 50% (10 mg, 6 μmol); mp 133-136° C.; $[α]^{24}_D$ +8.57 (c 0.04, chloroform); $^1$H NMR (CD$_3$OD, 400 MHz) δ 7.84 (1H, m), 7.61 (1H, dd, J=8.4 Hz, 1.6 Hz), 7.48 (1H, d, J=8.8 Hz), 5.44 (1H, m), 5.12 (9H, m), 4.99 (1H, m), 4.39 (2H, d, J=6.8 Hz), 4.25 (3H, m), 3.85 (1H, d, J=9.6 Hz), 3.52 (3H, m), 3.36 (2H, m), 2.94 (3H, s), 2.30 (7H, m), 1.74 (15H, m), 1.41 (10H, m) 1.29 (6H, m) and 0.95 (44H, m); $^{13}$C NMR (CD$_3$OD, 101 MHz) δ 175.10, 173.42, 173.40, 173.29, 173.16, 172.82, 172.77, 172.74, 172.12, 172.10, 172.01, 171.99, 171.97, 170.56, 157.75, 151.12, 141.73, 134.57, 132.65, 125.51, 119.06, 102.39, 77.66, 76.57, 74.87, 74.49, 74.44, 73.18, 71.95, 71.86, 71.79, 66.75, 60.00, 59.86, 59.80, 59.72, 57.24, 49.28, 41.97, 40.85, 40.83, 35.67, 34.99, 34.94, 34.90, 34.46, 33.37, 32.15, 32.12, 31.50, 31.40, 31.22, 31.07, 31.02, 27.43, 27.24, 27.04, 26.19, 25.70, 24.20, 23.75, 23.68, 23.61, 21.71, 21.60, 19.68, 19.63, 19.62, 19.61, 19.60, 19.28, 19.16, 18.93, 18.85, 18.78, 18.08, 18.03 and 17.19; HRFTMS (ESI), m/z 1687.7934 [M+Na]$^+$ (calcd for C$_{78}$H$_{120}$N$_8$O$_{31}$Na, 1687.7952).

Cancer Cell Line Procedures.

Inhibition of human cancer cell growth was assessed using the National Cancer Institute's standard sulforhodamine B assay as previously described.[19] In summary, cells in a 5% fetal bovine serum/RPMI1640 medium were inoculated in 96-well plates and incubated for 24 hrs. Next, serial dilutions of the compounds were added. After 48 h, the plates were fixed with trichloroacetic acid, stained with sulforhodamine B, and read with an automated microplate reader. A growth inhibition of 50% ($GI_{50}$ or the drug concentration causing a 50% reduction in the net protein increase) was calcd from optical density data with Immunosoft software. Normal cells were treated in identical conditions. Normal human prostate CRL-2221 (PZ—HPV-7) was grown in MEM 10% FBS and normal human breast MCF-10A in MEGM kit.

The growth inhibition property of the silstatins and some intermediates were evaluated against a mini panel of cancer cell lines (Table 1). An overall observation pointed to small modifications on the structure of the bacillistatin, while keeping the overall lipophilicity as shown for silstatin 1 (7a), did not affect its high potency. However, the introduction of polar groups (hydroxyl) somewhat decreased activity as shown for silstatins 2 and 3 (8a and 8b). Introduction of an α-hydroxy acid with a more lipophilic side chain in place of the three (R)-2-hydroxyisocaproic acid units caused a marked reduction of cancer cell growth inhibition capability as seen in silstatins 4 and 6 (14a and 15b). In contrast, silstatin 5 (15a) showed very high inhibitory activity.

In order to maximize the activity displayed versus lipophilicity, only one (R)-2-hydroxyisocaproic acid residue was interchanged with (2R)-2-hydroxy-3-cyclohexylpropionic acid thereby rescuing the activity as cancer cell growth inhibitors of the structures containing a hydroxyl group as shown by silstatins 7 and 8 (18a and 18b); although, without reaching the activity shown by silstatins 1 (7a) or the bacillistatins.

decreased 16-52 times with respect to the parent silstatin 7. Also, prodrug 28 was tested against two normal cell lines and compared to the parent drug (18a) (Table 2) and, as presumed, the prodrug 28 normal cell growth inhibition activity was decreased 62.5 and 12.5 times with respect to the parent silstatin 7 drug (18a) in MCF-10A and CRL-2221 cell lines, respectively.

TABLE 2

Growth inhibition of human normal cell lines (GI50 μg/mL)

| | Cell line[a] | |
|---|---|---|
| | MCF-10A | CRL-2221 |
| Silstatin 7 (18a) | 0.004 | 0.004 |
| 28 | 0.25 | 0.05 |

[a]Normal cell lines in order: breast (MCF-10A); prostate (CRL-2221).

The quite high activity of prodrug 28 displayed in cancer and normal cell lines might be attributed to the fact that the prodrug could be crossing the cell membrane and releasing the drug (18a). The difference in cell growth inhibition activity of prodrug 28, as shown in Table 2, could be due to the level of β-glucuronidase expression in each cell line. Recently, a doxorubicin glucuronide prodrug capable of binding albumin through a maleamide moiety was synthesized. The effects of this capability lead to a relatively non-toxic prodrug with higher accumulation in the tumor

TABLE 1

Growth inhibition of human cancer cell lines ($GI_{50}$ μg/mL).

| | Cell line[a] | | | | | |
|---|---|---|---|---|---|---|
| | BXPC3 | MCF-7 | SF268 | NCI-H460 | KM20L2 | DU145 |
| Bacillistatin 1[1] | 0.00095 | 0.00061 | 0.00045 | 0.0023 | 0.00087 | 0.0015 |
| Bacillistatin 2[1] | 0.00034 | 0.00031 | 0.0018 | 0.00045 | 0.00026 | 0.00086 |
| Silstatin 1 (7a) | 0.0008 | 0.00011 | 0.00021 | 0.0007 | 0.00016 | 0.00042 |
| 7c | 0.03 | 0.0042 | 0.0025 | 0.029 | 0.0048 | 0.011 |
| Silstatin 2 (8a) | 0.004 | 0.0022 | 0.0031 | 0.0032 | 0.0033 | 0.006 |
| Silstatin 3 (8b) | 0.005 | 0.0016 | 0.004 | 0.0037 | 0.0011 | 0.0051 |
| Silstatin 4 (14a) | 0.5 | 0.18 | 0.081 | 0.4 | 0.18 | 0.22 |
| 14b | 0.18 | 0.075 | 0.075 | 0.32 | 0.08 | 0.12 |
| 14c | >1 | >1 | >1 | >1 | >1 | >1 |
| Silstatin 5 (15a) | 0.03 | 0.0031 | 0.0044 | 0.021 | 0.0044 | 0.005 |
| Silstatin 6 (15b) | 0.53 | 0.12 | 0.05 | 0.32 | 0.09 | 0.22 |
| 17a | 0.023 | 0.001 | 0.004 | 0.009 | 0.0024 | 0.007 |
| 17b | 0.09 | 0.032 | 0.06 | 0.12 | 0.052 | 0.04 |
| Silstatin 7 (18a) | 0.0038 | 0.0014 | 0.0031 | 0.0032 | 0.0015 | 0.003 |
| Silstatin 8 (18b) | 0.006 | 0.0011 | 0.003 | 0.004 | 0.0021 | 0.0054 |
| 28 | 0.20 | 0.031 | 0.05 | 0.07 | 0.04 | 0.13 |

[a]Cancer cell lines in order: pancreas (BXPC-3); breast (MCF-7); CNS (SF268); lung (NCI-H460); colon (KM20L2); prostate (DU-145).

To demonstrate the utility of the new silstatins feasibility for forming prodrugs and linkers to monoclonals, prodrug 28 was synthesized and evaluated against the same mini panel of cancer cell lines (Table 1). The use of glucuronide prodrugs has been validated by in vivo studies showing superior therapeutic efficacy compared to the parent drug.[17]

In turn, that proved to be a prodrug that should have greatly reduced toxicity during transport to the tumor where a glucuronidase would release silstatin 7. Evidence of that expected result was obtained as follows. The cancer cell growth inhibition activity for prodrug 28 was found to be (more selective) as compared to the glucuronide prodrug without the maleamide moiety.[18]

Minimum Inhibitory Concentration Testing.

Compounds of the present disclosure are tested for antimicrobial activity in NCCLS broth microdilution assays following the protocol similar to that described in Pettit, G. R. et al., J. Nat. Prod. 2009, 72, 366-371.[20, 21]

Briefly, test compounds are reconstituted in a small volume of sterile DMSO and diluted in the appropriate media immediately prior to susceptibility experiments.[1] The MIC is defined as the lowest concentration inhibiting visible growth of the microorganism.

REFERENCES

The following references are hereby incorporated by reference in their entireties:

1. Pettit, G. R.; Knight, J. C.; Herald, D. L.; Pettit, R. K.; Hogan, F.; Mukku, V. J. R. V.; Hamblin, J. S.; Dodson II, M. J.; Chapuis, J-C. J. Nat. Prod. 2009, 72, 366-371.

2. Pettit, G. R.; Hu, S.; Knight, J. C.; Chapuis, J-C. J. Nat. Prod. 2009, 72, 372-379.

3. a) Fu, P; Johnson, M.; Chen, H.; Posner, B. A.; MacMillan, J. B. J. Nat. Prod. 2014, 77, 1245-1248. b) Bouhired, S. M.; Crüsemann, M.; Almeida, C.; Weber, T.; Piel, J.; Schäberle, T. F.; Köning, G. M. Chem Bio Chem 2014, 15, 757-765. c) Myobatake, Y.; Takemoto, K.; Kamisuki, S.; Inoue, N.; Takasaki, A.; Takeuchi, T.; Mizushina, Y.; Sugawara, F. J. Nat. Prod. 2014, 77, 1236-1240. d) Kong, F.; Wang, Y.; Liu, P.; Dong, T.; Zhu, W. J. Nat. Prod. 2014, 77, 132-137. e) Sun, Y-L.; Bao, J.; Liu, K-S.; Zhang, X-Y.; He, F.; Wang, Y-F.; Nong, X-H.; Qi, S-H. Planta Med 2013, 79, 1474-1479. f) Um, S.; Choi, T. J.; Kim, H.; Kim, B. Y.; Kim, S-H.; Lee, S. K.; Oh, K-B.; Shin, J.; Oh, D-C. J. Org. Chem. 2013, 78, 12321-12329. g) Meng, L-H.; Li, X-M.; Lv, C-T.; Li, C-S.; Xu, G-M, Huang, C-G.; Wang, B-G. J. Nat. Prod. 2013, 76, 2145-2149. h) Kuramochi, K.; Tsubaki, K.; Kuriyama, I.; Mizuchina, Y.; Yoshida, H.; Takeuchi, T.; Kamisuki, S.; Sugawara, F.; Kobayashi, S. J. Nat. Prod. 2013, 76, 1737-1745.

4. a) Skellam, E. J.; Steward, A. K.; Strangman, W. K.; Wright, J. L. C. J. Antibiot. 2013, 66, 431-441. b) Lin, Z.; Koch, M.; Pond, C. D.; Mabeza, G.; Seronay, R. A.; Concepcion, G. P.; Barrows, L. R.; Oliveira, B. M.; Schmidt, E. W. J. Antibiot. 2013, 67, 121-126. c) Jang, K. H.; Nam, S-J.; Locke, J. B.; Kauffman, C. A.; Beatty, D. S.; Paul, L. A.; Fenical, W. Angew. Chem. Int. Ed. 2013, 52, 7822-7824. d) Lu, Z.; Koch, M.; Harper, M. K.; Matainaho, T. K.; Barrows, L. R.; Van Wagoner, R. M.; Ireland, C. M. J. Nat. Prod. 2013, 76, 2150-2152. e) Wu, C.; Tan, Y.; Gan, M.; Wang, Y.; Guan, Y.; Hu, x.; Zhou, H.; Shang, X.; You, X.; Yang, Z.; Xiao, C. J. Nat. Prod. 2013, 76, 2153-2157. f) Felder, S.; Kehraus, S.; Neu, E.; Bierbaum, G.; Schäberle, T. F.; Köning, G. M. Chem Bio Chem 2013, 14, 1363-1371.

5. a) Xu, D-X.; Sun, P.; Kutan, T.; Mandi, A.; Tang, H.; Liu, B.; Gerwick, W. H.; Wang, Z-W.; Zhang, W. J. Nat. Prod. 2014, 77, 1179-1184. b) Du, F-Y.; Zhang, P.; Li, X-M.; Li, C-S.; Cui, C-M.; Wang, B-G. J. Nat. Prod. 2014, 77, 1164-1169. c) Wu, G.; Sun, X.; Yu, G.; Wang, W.; Zhu, T.; Gu, Q.; Li, D. J. Nat. Prod. 2014, 77, 270-275. d) Haga, A.; Tamoto, H.; Ishino, M.; Kimura, E. Sugita, T.; Kinoshita, K.; Takahashi, K.; Shiro, M.; Koyama, K. J. Nat. Prod. 2013, 76, 750-754. e) Bao, J.; Sun, Y-L.; Zhang, X-Y.; Han, Z.; Gao, H-C.; He, F.; Qian, P-Y.; Qi, S-H. J. Antibiot. 2013, 66, 219-223. f) He, F.; Bao, J.; Zhang, X-Y.; Tu, Z-C.; Shi, Y-M.; Qi, S-H. J. Nat. Prod. 2013, 76, 1182-1186.

6. a) Pavlik, C. M.; Wong, C. Y. B.; Ononye, S.; Lopez, D. D.; Engene, N.; McPhail, K. L. Gerwick, W. H.; Balunas, M. J. J. Nat. Prod. 2013, 76, 2026-2033. b) Thornburg, C. C.; Cowley, E. S.; Sikorska, J.; Shaala, L. A.; Ishmael, J. E.; Youssef, D. T. A.; McPhail, K. L. J. Nat. Prod. 2013, 76, 1781-1788. c) Tan, L. T. Drug Discov. Today 2013, 18, 863-871.

7. a) Guo, W.; Peng, J.; Zhu, T.; Gu, Q.; Keyzers, R. A.; Li. D. J. Nat. Prod. 2013, 76, 2106-2112. b) Um, S.; Kim, Y-J.; Kwon, H.; Wen, H.; Kim, S-H.; Kwon, H-C.; Park, S.; Shin, J.; Oh, D-C. J. Nat. Prod. 2013, 76, 873-879. c) Peng, J.; Zhang, X-Y.; Tu, Z-C.; Xu, X-Y.; Qi, S-H. J. Nat. Prod. 2013, 76, 983-987. d) Pettit, R. K. Mar. Biotechnol. 2011, 13, 1-11.

8. Suwan, S.; Isobe, M.; Ohtani, I.; Agata, N.; Mori, M.; Ohta, M. J. Chem. Soc. Perkin Trans. 1 1995, 765-775.

9. Glueck, S. M.; Pirker, M.; Nestl, B. M.; Ueberbacher, B. T.; Larissegger-Schnell, B.; Csar, K.; Hauer, B.; Stuermer, R.; Kroutil, W.; Faber, K. J. Org. Chem. 2005, 70, 4028-4032

10. Bollenback, G. N.; Long, J. W.; Benjamin, D. G.; Lindquist, J. A. J. Am. Chem. Soc. 1955, 77, 3310-3315.

11. Duimstra, J. A.; Femia, F. J.; Meade, T. J. J. Am. Chem. Soc. 2005, 127, 12847-12855.

12. Grinda, M.; Clarhaut, J.; Tranoy-Opalinski, I.; Renoux B.; Monvoisin, A.; Cronier, L.; Papot, S. Chem Med Chem 2011, 6, 2137-2141.

13. Alaoui, A. E.; Schmidt, F.; Monneret, C.; Florent, J-C. J. Org. Chem. 2006, 71, 9628-9636.

14. a) Bouvier, E.; Thirot, S.; Schmedt, F.; Monneret, C. Org. Biomol. Chem. 2003, 1, 3343-3352. b) de Bond, D. B. A.; Leenders, R. G. G.; Haisma, H. J.; Van Der Meulen-Muileman, I. H.; Scheeren, H. W. Bioorg. Med. Chem. 1997, 5, 405-414. c) DeWit, M. A.; Gillies, E. R. Org. Biomol. Chem. 2011, 9, 1846-1854.

15. Iacobazzi, R. M.; Annese, C.; Azzariti, A.; D'Accolti, L.; Franco, M.; Fusco, C.; Gianluigi, L. P.; Laquintana, V.; Denora, N. ACS Med. Chem. Lett. 2013, 4, 1189-1192.

16. Halsey, C. M.; Benham, D. A.; JiJi, R. D.; Cooley, J. W. Spectrochim. Acta Mol. Biomol. Spectros. 2012, 96, 200-206.

17. a) Houba, P. H. J.; Boven, E.; Van Der Meulen-Muileman, I. H.; Lenders, R. G. G.; Scheeren, J. W.; Pinedo, H. M.; Haisima, H. J. Br. J. Cancer 2001, 84, 550-557. b) Bosslet, K.; Straub, R.; Blumrich, M.; Czech, J.; Gerken, M.; Sperker, B.; Kroemer, H. K.; Gesson, J-P.; Koch, M.; Monneret, C. Cancer Res. 1998, 58, 1195-1201. c) Woessner, R.; An, Z.; Li, X.; Hoffman, R. M.; Dix, R.; Bitonti, A. Anticancer Res. 2000, 20, 2289-2296. d) Legigan, T.; Clarhaut, J.; Renoux, B.; Tranoy-Opalinski, I.; Monvoisin, A.; Jayle, C.; Alsarraf, J.; Thomas, M.; Papot, S Eu. J. Med. Chem. 2013, 67, 75-80.

18. Legigan, T.; Clarhaut, J.; Renoux, B.; Tranoy-Opalinski, I.; Monvoisin, A.; Berjeaud, J-M.; Guilhot, F.; Papot, S J. Med. Chem. 2012, 55, 4516-4520.

19. Monks, A.; Scudiero, D.; Skehan, P.; Shoemaker, R.; Paull, K.; Vistica, D.; Hose, C.; Langley, J.; Cronise, P.; Viagro-Wolff, A.; Gray-Goodrich, M.; Campbell, H.; Mayo, J.; Boyd, M. J. Natl. Cancer Inst. 1991, 83, 757-766.

20. NCCLS. Methods for Dilution Antimicrobial Susceptibility Tests for Bacteria That Grow Aerobically; Approved Standard—Fifth Edition. NCCLS document M7-A5 [ISBN 1-56238-394-9]. NCCLS, 940 West Valley Road, Suite 1400, Wayne, Pa. 19087-1898 USA, 2000.

21. NCCLS. Reference Method for Broth Dilution Antifungal Susceptibility Testing of Yeasts; Approved Standard—Second Edition. NCCLS document M27-A2 [ISBN 1-56238-469-4]. NCCLS, 940 West Valley Road, Suite 1400, Wayne, Pa. 19087-1898 USA, 2002.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present

What is claimed is:

1. A compound of formula (Ia):

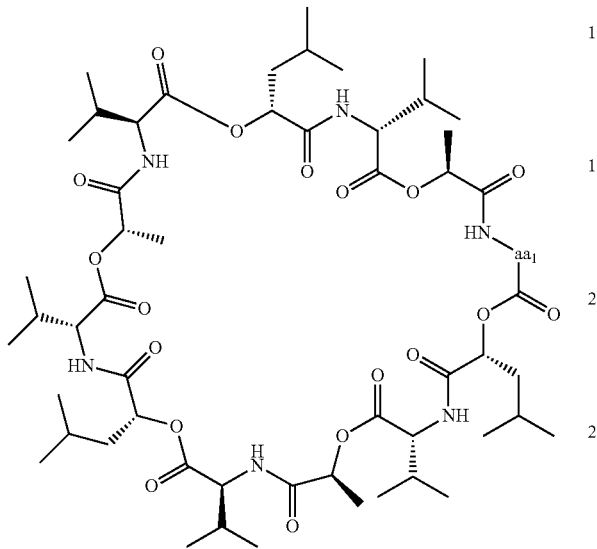

(Ia)

or a pharmaceutically acceptable salt thereof, wherein aa₁ is threonine optionally substituted with a protecting group or a bifunctional moiety.

2. The compound of claim 1, wherein the bifunctional moiety comprises a cleavable linker.

3. The compound of claim 2, wherein the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage.

4. The compound of claim 2, wherein the cleavable linker comprises a glycosidic bond, a hydrazone, a cathepsin-B-cleavable peptide, a disulfide or an ester bond.

5. The compound of claim 2, wherein the cleavable linker comprises glucuronide.

6. The compound of claim 1, wherein the bifunctional moiety comprises a monoclonal antibody.

7. A pharmaceutical composition comprising a compound of claim 1 or a pharmaceutically acceptable salt thereof and a pharmaceutically acceptable carrier.

8. A pharmaceutical composition comprising a combination of compounds of claim 1 or pharmaceutically acceptable salts thereof and a pharmaceutically acceptable carrier.

9. The pharmaceutical composition of claim 7, further comprising a therapeutically effective amount of chemotherapeutic agent selected from the group consisting of a tubulin-forming inhibitor, a topoisomerase inhibitor, and a DNA binder.

10. A compound of formula (Ia):

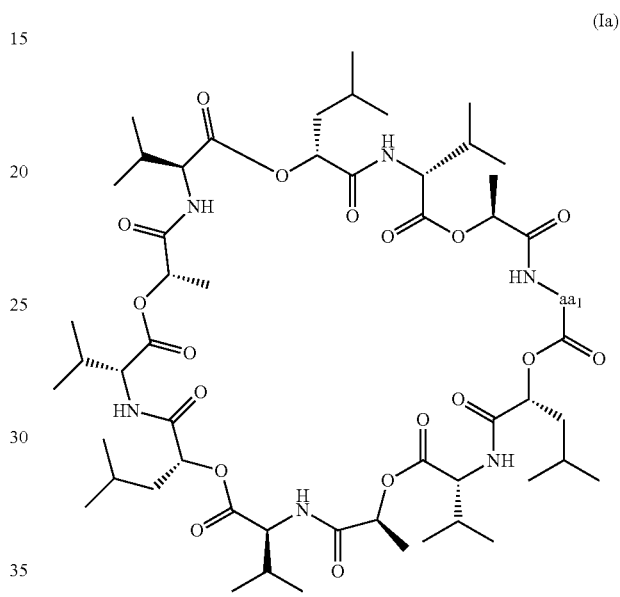

(Ia)

or a pharmaceutically acceptable salt thereof, wherein aa₁ is threonine.

11. The compound of claim 1, wherein the bifunctional moiety is represented by formula (III):

$$A_a\text{-}W_w\text{-}Y_y \quad \text{(III)},$$

wherein:
$A_a$ is maleimidocaproyl,
$W_w$ is Valine-Citrulline, and
$Y_y$ is para-aminobenzyloxycarbonyl.

* * * * *